(12) United States Patent
Small et al.

(10) Patent No.: US 9,944,661 B2
(45) Date of Patent: Apr. 17, 2018

(54) OLEFIN HYDROBORATION

(71) Applicant: Chevron Phillips Chemical Company LP, The Woodlands, TX (US)

(72) Inventors: Brooke L. Small, Kingwood, TX (US); Brian A. Schaefer, Hillsborough, NJ (US); Paul J. Chirik, Princeton, NJ (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/232,442

(22) Filed: Aug. 9, 2016

(65) Prior Publication Data
US 2018/0044354 A1 Feb. 15, 2018

(51) Int. Cl.
C07F 5/02 (2006.01)
B01J 31/22 (2006.01)
C07C 1/32 (2006.01)

(52) U.S. Cl.
CPC ........... *C07F 5/027* (2013.01); *B01J 31/2295* (2013.01); *C07C 1/321* (2013.01)

(58) Field of Classification Search
CPC .......... C07F 5/02; C07F 5/027; B01J 31/2295
See application file for complete search history.

(56) References Cited

U.S. PATENT DOCUMENTS

| | | | |
|---|---|---|---|
| 4,971,986 A | 11/1990 | Stanek et al. | |
| 5,714,556 A | 2/1998 | Johnson et al. | |
| 5,811,618 A | 9/1998 | Wu | |
| 5,880,241 A | 3/1999 | Brookhart et al. | |
| 5,955,555 A | 9/1999 | Bennett | |
| 6,063,881 A | 5/2000 | Bennett | |
| 6,103,658 A | 8/2000 | Mackenzie et al. | |
| 6,103,946 A | 8/2000 | Brookhart, III et al. | |
| 6,150,482 A | 11/2000 | Brookhart et al. | |
| 6,184,428 B1 | 2/2001 | Zahoor et al. | |
| 6,200,920 B1 | 3/2001 | Debras et al. | |
| 6,214,761 B1 | 4/2001 | Bennett | |
| 6,239,237 B1 | 5/2001 | Xu et al. | |
| 6,281,303 B1 | 8/2001 | Lavoie et al. | |
| 6,291,733 B1 | 9/2001 | Small et al. | |
| 6,369,177 B1 | 4/2002 | Tohi et al. | |
| 6,399,535 B1 | 6/2002 | Shih et al. | |
| 6,407,188 B1 | 6/2002 | Guan et al. | |
| 6,414,098 B1 | 7/2002 | Engehausen et al. | |
| 6,417,305 B2 | 7/2002 | Bennett | |
| 6,417,364 B1 | 7/2002 | Lenges | |
| 6,423,848 B2 | 7/2002 | Bennett | |
| 6,432,862 B1 | 8/2002 | Bennett | |
| 6,451,939 B1 | 9/2002 | Britovsek et al. | |
| 6,458,739 B1 | 10/2002 | Kimberley et al. | |
| 6,458,905 B1 | 10/2002 | Schmidt et al. | |
| 6,461,994 B1 | 10/2002 | Gibson et al. | |
| 6,465,386 B1 | 10/2002 | Maddox et al. | |
| 6,489,428 B1 | 12/2002 | Debras et al. | |
| 6,489,497 B1 | 12/2002 | Brookhart, III et al. | |
| 6,534,691 B2 | 3/2003 | Culver et al. | |
| 6,545,108 B1 | 4/2003 | Moody et al. | |
| 6,548,672 B1 | 4/2003 | Gibson et al. | |
| 6,555,633 B1 | 4/2003 | Tanaka et al. | |
| 6,562,973 B1 | 5/2003 | Liu | |
| 6,683,141 B1 | 1/2004 | Gibson et al. | |
| 6,683,187 B2 | 1/2004 | De Boer et al. | |
| 6,710,006 B2 | 3/2004 | De Boer et al. | |
| 6,713,566 B1 | 3/2004 | Marcuccio et al. | |
| 6,720,468 B2 | 4/2004 | Elomari et al. | |
| 6,740,715 B2 | 5/2004 | Brookhart, III et al. | |
| 6,777,584 B2 | 8/2004 | Patil et al. | |
| 6,787,499 B2 | 9/2004 | Tanaka et al. | |
| 6,818,715 B1 | 11/2004 | Kristen et al. | |
| 6,825,297 B1 | 11/2004 | Devore et al. | |
| 6,841,693 B1 | 1/2005 | Watanabe et al. | |
| 6,894,134 B2 | 5/2005 | Brookhart et al. | |
| 6,911,505 B2 | 6/2005 | Small | |
| 6,911,506 B2 | 6/2005 | Small et al. | |
| 6,927,313 B2 | 8/2005 | Bianchini et al. | |
| 7,001,964 B2 | 2/2006 | Small | |
| 7,037,988 B2 | 5/2006 | De Boer et al. | |
| 7,045,632 B2 | 5/2006 | Small | |
| 7,049,442 B2 | 5/2006 | De Boer et al. | |
| 7,053,020 B2 | 5/2006 | De Boer et al. | |
| 7,053,259 B2 | 5/2006 | Culver et al. | |

(Continued)

FOREIGN PATENT DOCUMENTS

| | | |
|---|---|---|
| CN | 1306014 A | 8/2001 |
| CN | 1358772 A | 7/2002 |
| CN | 1374281 A | 10/2002 |
| CN | 1850339 A | 10/2006 |
| DE | 19812066 A1 | 1/1999 |

(Continued)

OTHER PUBLICATIONS

Gilbert-Wilson et al. ("Phosphine-Iminopyridines as Platforms for Catalytic Hydrofunctionalization of Alkenes", Inorganic Chemistry, American Chemical Society, vol. 54, Issue 11, May 2015, pp. 5596-5603).*

(Continued)

*Primary Examiner* — Rosalynd A Keys
(74) *Attorney, Agent, or Firm* — Conley Rose, P.C.; Rodney B. Carroll; Monte R. Rhodes

(57) ABSTRACT

A process comprising contacting a) an alkene, b) a hydrogen-boron bond containing compound, c) an α-diimine metal salt complex comprising an α-diimine iron salt complex or an α-diimine cobalt salt complex, and d) a group 1 metal borohydride under conditions suitable to form an alkylboron compound. A process comprising contacting a) an alkene, b) a hydrogen-boron bond containing compound, and c) an α-diimine metal salt complex comprising an α-diimine iron methylenetrihydrocarbylsilyl complex or an α-diimine cobalt methylenetrihydrocarbylsilyl complex, to form an alkyl-boron compound under conditions suitable to form an alkylboron compound. A process comprising contacting an alkene, a hydrogen-boron bond containing compound, and an α-diimine metal salt complex to form an alkyl-boron compound under conditions suitable to form an alkylboron compound.

17 Claims, 1 Drawing Sheet

(56) References Cited

U.S. PATENT DOCUMENTS

| | | |
|---|---|---|
| 7,129,304 B1 | 10/2006 | Small et al. |
| 7,176,266 B2 | 2/2007 | Haruhito et al. |
| 7,179,871 B2 | 2/2007 | De Boer et al. |
| 7,223,893 B2 | 5/2007 | Small et al. |
| 7,238,764 B2 | 7/2007 | De Boer et al. |
| 7,268,096 B2 | 9/2007 | Small et al. |
| 7,271,121 B2 | 9/2007 | Small et al. |
| 7,297,806 B2 | 11/2007 | Brookhart, III et al. |
| 7,442,819 B2 | 10/2008 | Ionkin et al. |
| 7,456,284 B2 | 11/2008 | Small |
| 7,589,245 B2 | 9/2009 | De Boer et al. |
| 7,727,926 B2 | 6/2010 | Small et al. |
| 7,728,160 B2 | 6/2010 | Small et al. |
| 7,728,161 B2 | 6/2010 | Small et al. |
| 7,977,269 B2 | 7/2011 | Small et al. |
| 9,120,826 B1 | 9/2015 | Sydora et al. |
| 2002/0058584 A1 | 5/2002 | Bennett et al. |
| 2003/0050494 A1 | 3/2003 | Brookhart, III et al. |
| 2004/0122269 A1 | 6/2004 | Van Zon et al. |
| 2004/0122271 A1 | 6/2004 | Van Zon et al. |
| 2004/0143147 A1 | 7/2004 | Ittel et al. |
| 2012/0309965 A1 | 12/2012 | Sydora et al. |
| 2013/0331629 A1 | 12/2013 | Sydora et al. |
| 2014/0221645 A1 | 8/2014 | Sydora et al. |
| 2017/0182486 A1* | 6/2017 | Lin .................. B01J 31/1691 |

FOREIGN PATENT DOCUMENTS

| | | |
|---|---|---|
| EP | 1188762 A1 | 3/2002 |
| EP | 1325924 A1 | 7/2003 |
| JP | 2002371062 A | 12/2002 |
| JP | 2003147009 A | 5/2003 |
| WO | 9611193 A1 | 4/1996 |
| WO | 9827124 A1 | 6/1998 |
| WO | 9950318 A1 | 10/1999 |
| WO | 9962963 A1 | 12/1999 |
| WO | 9962967 A2 | 12/1999 |
| WO | 0020427 A1 | 4/2000 |
| WO | 0021966 A1 | 4/2000 |
| WO | 0058320 A1 | 10/2000 |
| WO | 0066638 A1 | 11/2000 |
| WO | 0068280 A1 | 11/2000 |
| WO | 0069923 A1 | 11/2000 |
| WO | 0110875 A1 | 2/2001 |
| WO | 0123443 A1 | 4/2001 |
| WO | 0136503 A1 | 5/2001 |
| WO | 0158874 A1 | 8/2001 |
| WO | 0174830 A1 | 10/2001 |
| WO | 0200339 A2 | 1/2002 |
| WO | 0210133 A1 | 2/2002 |
| WO | 0228805 A2 | 4/2002 |
| WO | 0234701 A1 | 5/2002 |
| WO | 0234746 A2 | 5/2002 |
| WO | 02079276 A2 | 10/2002 |
| WO | 02090365 A1 | 11/2002 |
| WO | 0296919 A1 | 12/2002 |
| WO | 03010207 A1 | 2/2003 |
| WO | 03011876 A1 | 2/2003 |
| WO | 03022889 A1 | 3/2003 |
| WO | 03053890 A1 | 7/2003 |
| WO | 03053891 A1 | 7/2003 |
| WO | 03059511 A1 | 7/2003 |
| WO | 2004026795 A2 | 4/2004 |
| WO | 2004029012 A1 | 4/2004 |
| WO | 2004033398 A1 | 4/2004 |
| WO | 2004043887 A2 | 5/2004 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005092821 A1 | 10/2005 |
| WO | 2005111099 A1 | 11/2005 |
| WO | 2006008438 A1 | 1/2006 |
| WO | 2006016101 A1 | 2/2006 |
| WO | 2007013931 A2 | 2/2007 |
| WO | 2007013931 A3 | 2/2007 |
| WO | 2007059015 A1 | 5/2007 |
| WO | 2007080081 A2 | 7/2007 |
| WO | 2008038173 A2 | 4/2008 |

OTHER PUBLICATIONS

Bennett, Alison M. A., "Novel, highly active iron and cobalt catalysts for olefin polymerization," Chemtech, Jul. 1999, pp. 24-28, vol. 29, No. 7, American Chemical Society.

Britovsek, George J. P., et al., "Iron and Cobalt Ethylene Polymerization Catalysts Bearing 2,6-Bis(Imino) Pyridyl Ligands: Synthesis, Structures, and Polymerization Studies," J. Am. Chem. Soc., 1999, pp. 8728-8740, vol. 121, No. 38, American Chemical Society.

Britovsek, George J. P., et al., "Novel olefin polymerization catalysts based on iron and cobalt," Chem. Comm., 1998, pp. 849-850.

Britovsek, George J. P., et al., "Oligomerisation of Ethylene by Bis(imino)pyridyliron and -cobalt Complexes," Chem. Eur. J., 2000, pp. 2221-2231, vol. 6, No. 12, Wiley-VCH Verlag GmbH, Weinheim.

Caballero, Ana, et al., "Ruthenium-Catalyzed Hydroboration and Dehydrogenative Borylation of Linear and Cyclic Alkenes with Pinacolborane," Organometallics, 2007, pp. 1191-1195, vol. 26, No. 5, American Chemical Society.

Carter, Anthea et al., "High activity ethylene trimerisation catalysts based on diphosphine ligands," Chem. Commun., 2002, pp. 858-859 plus 2 pages Supplementary Information, The Royal Society of Chemistry.

Chang, Sechin, et al., "Model Complexes of the Active Site in Peptide Deformylase: A New Family of Mononuclear $N_2$S-M(II) Complexes," Inorganic Chemistry, 2001, vol. 40, No. 2, pp. 194-195, American Chemical Society.

Chen, Yaofeng, et al., "Fluoro-Substituted 2,6-Bis(imino)pyridyl Iron and Cobalt Complexes: High-Activity Ethylene Oligomerization Catalysts," Organometallics, 2003, pp. 1231-1236, vol. 22, No. 6, American Chemical Society.

Cipot, Judy, et al., "Catalytic Alkene Hydroboration Mediated by Cationic and Formally Zwitterionic Rhodium(I) and Iridium(I) Derivatives of a P,N-Substituted Indene," Organometallics, 2006, pp. 5965-5968, vol. 25, No. 25, American Chemical Society.

De Klerk, Arno, et al., "Linear α-Olefins from Linear Internal Olefins by a Boron-Based Continuous Double-Bond Isomerization Process," Ind. Eng. Chem. Res., 2007, pp. 400-410, vol. 46, No. 2, American Chemical Society.

Dubois, Thomas D., "Four- and Five-Coordinate Nickel(II) Complexes of 2,3-Butanedionebis(2-diphenylphosphinoethylamine)," Inorganic Chemistry, 1972, vol. 11, No. 4, pp. 718-722.

Esteruelas, Miguel A., et al., "Preparation, Structure and Ethylene Polymerization Behavior of Bis(imino)pyridyl Chromium(III) Complexes," Organometallics, 2003, pp. 395-406, vol. 22, No. 3, American Chemical Society.

Evans, David A., et al., "Mechanistic Study of the Rhodium(I)-Catalyzed Hydroboration Reaction," J. Am. Chem. Soc., 1992, pp. 6679-6685, vol. 114, No. 17, American Chemical Society.

Evans, David A., et al., "Rhodium(I)- and Iridium(I)-Catalyzed Hydroboration Reactions: Scope and Synthetic Applications," J. Am. Chem. Soc., 1992, pp. 6671-6679, vol. 114, No. 17, American Chemical Society.

Foreign communication from a counterpart application—Invitation to Pay Additional Fees and Partial Search Report, PCT/US2006/028068, dated Jan. 5, 2007, 6 pages.

Foreign communication from a counterpart application—International Search Report and Written Opinion, PCT/US2006/028068, dated Jun. 20, 2007, 15 pages.

Foreign communication from a counterpart application—International Preliminary Report on Patentability, PCT/US2006/028068, dated Jan. 22, 2008, 9 pages.

Foreign communication from a counterpart application—Office Action, CN200680033897.1, dated Dec. 31, 2010, 6 pages.

Ghebreyessus, Kesete Y., et al. "Isomerizing-Hydroboration of the Monounsaturated Fatty Acid Ester Methyl Oleate," Organometallics, 2006, pp. 3040-3044, vol. 25, No. 12, American Chemical Society.

(56) References Cited

OTHER PUBLICATIONS

"Group notation revised in periodic table," Feb. 4, 1985, pp. 26-27, C&EN.

Katritzky, Alan R., et al., "Syntheses of 1,4-Benzothiazepines and 1,4-Benzoxazepines via Cyclizations of 1-[2Arylthio(oxy)ethyl]-5-benzotriazolyl-2-pyrrolidinones and 3-Benzotriazolyl-2[2-arylthio(oxy)ethyl]-1-isoindolinones," J. Org.Chem., 2001, pp. 5590-5594, vol. 66, No. 16, American Chemical Society.

Kumar, R. N., et al., "Mononuclear and Binuclear Complexes of Fe(II) and Cu(II) with 2,6-Diacetyl Pyridine Monoxime and Phenylene Diamine," Asian Journal of Chemistry, 1999, pp. 964-969, vol. 11, No. 3.

Lata, Christopher J., et al., "Dramatic Effect of Lewis Acids on the Rhodium-Catalyzed Hydroboration of Olefins," J. Am. Chem. Soc., 2010, pp. 131-137, vol. 132, No. 1, American Chemical Society.

McGuinness, David S., et al., "First Cr(III)-SNS Complexes and Their Use as Highly Efficient Catalysts for the Trimerization of Ethylene to 1-Hexene," J. Am. Chem. Soc., 2003, pp. 5272-5273, vol. 125, No. 18, American Chemical Society.

McGuinness, David S., et al., "Novel Cr-PNP complexes as catalysts for the trimerisation of ethylene," Chem. Comm., 2003, pp. 334-335.

McNaught, Alan D., et al., "Compendium of Chemical Terminology," International Union of Pure and Applied Chemistry, Second edition, 1997, 5 pages of cover, publishing information, and contents, Wiley-Blackwell.

Nielson, S. Martin, et al., "Metal-ion Controlled Reactions of 2, 6 Diacetylpyridine with 1,2-Di-aminoethane and 2,6-Diformylpyridine with o-Phenylenediamine and the Crystal and Molecular Structure of a Pentagonal Pyramidal Cadmium (II) Complex containing Unidentate o-Phenylenediamine," 1982, pp. 407-415, J.C.S. Dalton.

Obligacion, Jennifer V., et al., "Bis(imino)pyridine Cobalt-Catalyzed Alkene Isomerization-Hydroboration: A Strategy for Remote Hydrofunctionalization with Terminal Selectivity," Journal of the American Chemical Society, 2013, pp. 19107-19110, vol. 135, American Chemical Society.

Obligacion, Jennifer V., et al., "Highly Selective Bis(imino)pyridine Iron-Catalyzed Alkene Hydroboration," Organic Letters, 2013, pp. 2680-2683, vol. 15, No. 11, American Chemical Society.

Palmer, W. Neil, et al., "High-Activity Cobalt Catalysts for Alkene Hydroboration with Electronically Responsive Terpyridine and α-Diimine Ligands," ACS Catalysis, 2015, pp. 622-626, vol. 5, American Chemical Society.

Pereira, Schubert, et al., "Transition Metal-Catalyzed Hydroboration of and $CCl_4$ Addition to Alkenes," J. Am. Chem. Soc., 1996, pp. 909-910, vol. 118, No. 4, American Chemical Society.

Rosenberger, Volker, et al.; "Diazadien-Komplexe des Rutheniums, XIII. Bis(diazadien)ruthenium: Isomerisierung, Hydrierung, Metaillierung; Struktur eines Kalium(tmeda)$_2$-ruthenats(0)," XP-002410474, Journal of Organometallic Chemistry, 1991, pp. 445-456, vol. 411, Elsevier Sequoia, S.A.

Ruddy, Adam J., et al, "(N-Phosphinoamidinate)cobalt-Catalyzed Hydroboration: Alkene Isomerization Affords Terminal Selectivity," Chem. Eur. J., 2014, pp. 13918-13922, vol. 20, Wiley-VCH Verlag GmbH & Co. KGaA, Weinheim.

Ruddy, Adam J., et al, "(N-Phosphinoamidinate)Iron Pre-Catalysts for the Room Temperature Hydrosilylation of Carbonyl Compounds with Broad Substrate Scope at Low Loadings," Organometallics, 2013, pp. 5581-5588, vol. 32, American Chemical Society.

Small, Brooke L., et al., "Comparative Dimerization of 1-Butene with a Variety of Metal Catalysts, and the Investigation of a New Catalyst for C-H Bond Activation," Chem. Eur. J., 2004, pp. 1014-1020 plus 4 pages Supporting Information, vol. 10, Wiley-VCH Verlag GmbH & Co. KGaA, Weinheim.

Small, Brooke L., et al. "Highly Active Iron and Cobalt Catalysts for the Polymerization of Ethylene," J. Am. Chem. Soc., 1998, vol. 120, No. 16, pp. 4049-4050, American Chemical Society.

Small, Brooke L., et al., "Iron-Based Catalysts with Exceptionally High Activities and Selectivities for Oligomerization of Ethylene to Linear α-Olefins," J. Am. Chem. Soc., 1998, pp. 7143-7144, vol. 120, No. 28, American Chemical Society.

Small, Brooke L., et al., "Iron Catalysts for the Head-to-Head Dimerization of α-Olefins and Mechanistic Implications for the Production of Linear α-Olefins," Organometallics, 2001, pp. 5738-5744, vol. 20, No. 26, American Chemical Society.

Small, Brooke L, at al., "New Chromium Complexes for Ethylene Oligomerization: Extended Use of Tridentate Ligands in Metal-Catalyzed Olefin Polymerization," Macromolecules, 2004, pp. 4375-4386, vol. 37, No. 12, American Chemical Society.

Small, Brooke L., et al., "New Iron and Cobalt Catalysts for the Polymerization of Olefins," Dallas ACS, 1998, p. 213, vol. 39.

Small, Brooke L., et al., "Polymerization of Propylene by a New Generation of Iron Catalysts: Mechanisms of Chain Initiation, Propagation, and Termination," XP-000823810, Macromolecules, 1999, pp. 2120-2130, vol. 32, No. 7, American Chemical Society.

Stojcevic, Goran, et al., "Coordination insertion reactions of acrylonitrile into Pd-H and Pd-methyl bonds in a diimine-palladium(II) system," XP-002410475, Journal of Organometallic Chemistry, 2005, pp. 4349-4355, vol. 690, Elsevier B.V.

Stollenz, Michael, et al., "Complexes of Nickel(II) with Oxalic Amidines and Oxalic Amidinates with Additional $R_2P$-Donor Groups," Z. Anorg. Allg. Chem., 2004, pp. 2701-2708, vol. 630, Wiley-VCH Verlag GmbH & Co. KGaA, Weinheim.

Tempel, Daniel J., et al., "Mechanistic Studies of Pd(II)—α-Diimine-Catalyzed Olefin Polymerizations," XP-002410476, J. Am. Chem. Soc., 2000, pp. 6686-6700, vol. 122, No. 28, American Chemical Society.

Wang, Sheena Hallin, et al. "Catalytic Sulfoxidation and Epoxidation with a Mn(III) Triazacorrole: Evidence for a "Third Oxidant" in High-Valent Porphyrinoid Oxidations," J. Am. Chem. Soc., 2004, pp. 18-19, vol. 126, No. 28, American Chemical Society.

Yamamoto, Yasunori, et al., "Iridium-catalyzed hydroboration of alkenes with pinacolborane," Tetrahedron, 2004, pp. 10695-10700, vol. 60, Elsevier, Ltd.

Zhang, Lei, et al., "Iron-Catalyzed, Atom-Economical, Chemo- and Regioselective Alkene Hydroboration with Pinacolborane," Angewandte Chemie International Edition, 2013, pp. 3676-3680, vol. 52, Wiley-VCH Verlag GmbH & Co. KGaA, Weinheim.

* cited by examiner

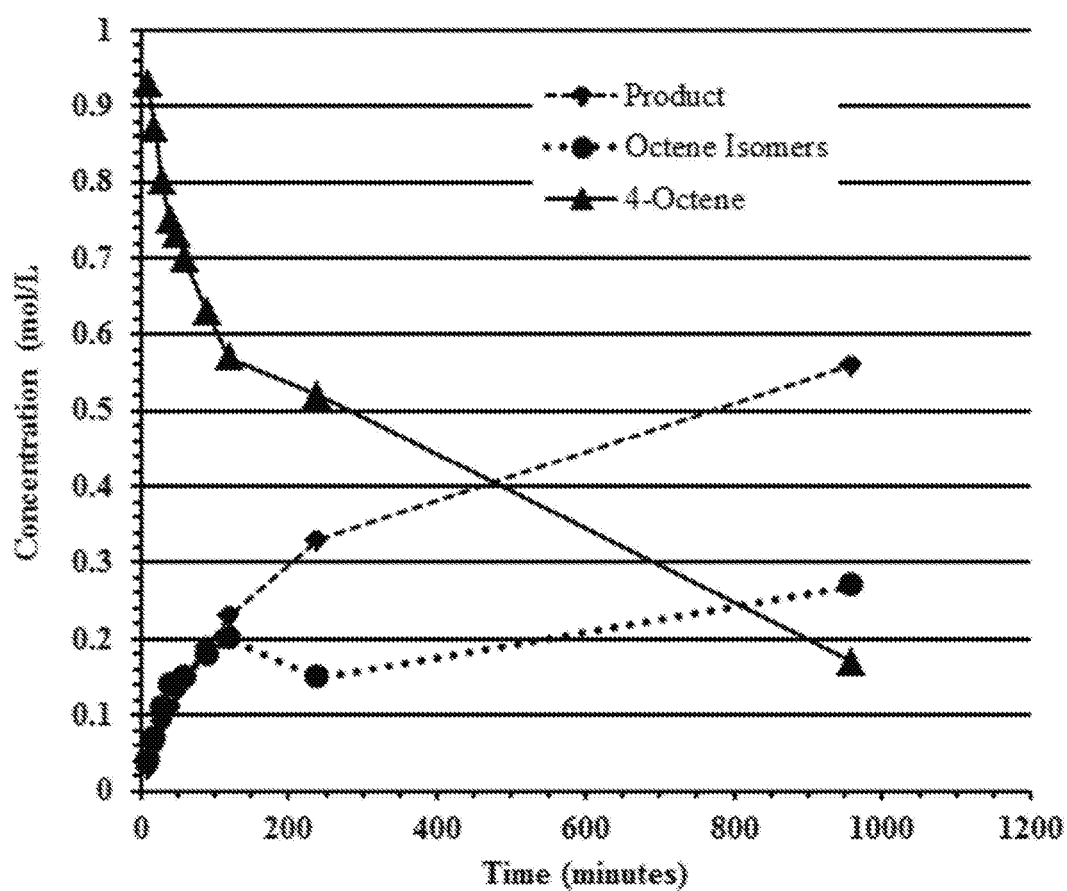

OLEFIN HYDROBORATION

TECHNICAL FIELD

The present disclosure relates to the transition metal-catalyzed hydroboration of olefins (e.g., alkenes). Particularly, the present disclosure relates to the use of α-diimine metal complexes as hydroboration catalysts.

BACKGROUND

Hydroboration is the addition of a borane compound to an olefin to form an organoborane. The hydroboration of olefins such as alkenes thermodynamically favors the formation of terminal organoboranes. However, hydroboration of internal olefins typically requires utilization of expensive catalysts or harsh conditions (e.g., high temperatures) while typically suffering from poor yield and selectivity. Thus, an ongoing need exists for catalysts that provide improved hydroboration of internal olefins.

SUMMARY

Disclosed herein is a process comprising contacting a) an alkene, b) a hydrogen-boron bond containing compound, c) an α-diimine metal salt complex comprising an α-diimine iron salt complex or an α-diimine cobalt salt complex, and d) a group 1 metal borohydride under conditions suitable to form an alkylboron compound.

Also disclosed herein is a process comprising contacting a) an alkene, b) a hydrogen-boron bond containing compound, and c) an α-diimine metal salt complex comprising an α-diimine iron methylenetrihydrocarbylsilyl complex or an α-diimine cobalt methylenetrihydrocarbylsilyl complex to form an alkyl-boron compound under conditions suitable to form an alkylboron compound.

Also disclosed herein is a process comprising contacting an alkene, a hydrogen-boron bond containing compound, and an α-diimine metal salt complex to form an alkyl-boron compound under conditions suitable to form an alkylboron compound.

DESCRIPTION OF THE DRAWINGS

FIG. 1 is plot of the product distribution as a function of time for a hydroboration reaction of the type disclosed herein.

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements are indicated using the numbering scheme indicated in the version of the periodic table of elements published in *Chemical and Engineering News*, 63(5), 27, 1985. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition (i.e., Material A). When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting essentially of specific or alternatively consists of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogens atoms, as necessary for the situation, removed from the alkane. Throughout the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the processes described herein in which the material having an inert functional group takes part and/or does not complex with the metal compound of the metal complex. The term "does not complex with the metal compound" can include groups that could complex with a metal compound but in particular molecules. The inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group can be derived by removal of a hydrogen atom from a terminal carbon atom of a linear alkane.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

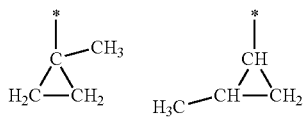

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or aromatic ring system. The term "olefin" includes aliphatic and aromatic, cyclic and acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched, and/or acyclic or cyclic, hydrocarbon olefin that has one or more carbon-carbon double bonds. Alkenes having only one, only two, only three, etc. . . . of such multiple bonds can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group is generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An "arene" is an aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and/or contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

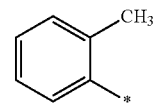 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran)

and a heteroarene group if the removed hydrogen carbon came from a heteroaromatic ring or ring system carbon atom (e.g. the 2 or 7 carbon atom of the benzofuran group or 6-phenylbenzofuran). It should be noted that according to the definitions provided herein, general arene groups (including an aryl group and an arylene group) include those having zero, one, or more than one hydrocarbyl substituent groups located on an aromatic hydrocarbon ring or ring system carbon atom (e.g. a toluene group or a xylene group, among others) and is a member of the hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according to the definitions provided herein, general aralkane groups include those having zero, one, or more than one hydrocarbyl substituent groups located on an aralkane aromatic hydrocarbon ring or ring system carbon atom is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Unless specified otherwise, the terms "contacted," "combined," and "in the presence of" refer to any addition sequence, order, or concentration for contacting or combining two or more components of the oligomerization process. Combining or contacting of the metal complex, hydrogen-boron bond containing compound and alkene, according to the various methods described herein can occur in one or more contact zones under suitable contact conditions such as temperature, pressure, contact time, flow rates, etc. . . . . The contact zone can be disposed in a vessel (e.g. a storage tank, tote, container, mixing vessel, reactor, etc.), a length of pipe (e.g. a tee, inlet, injection port, or header for combining component feed lines into a common line), or any other suitable apparatus for bringing the components into contact. The processes can be carried out in a batch or continuous process as is suitable for a given embodiment, with physical parameters of the contact zone being specified accordingly.

Generally, the present application is directed to processes for and/or including the hydroboration of an olefin (or and alkene) using a metal complex. In an aspect the present application is directed to using α-diimine metal complexes for hydroborating an alkene. In an aspect the present application is directed to a process comprising contacting an olefin (or alkene), a hydrogen-boron bond containing compound, and an α-diimine metal complex under conditions suitable to form an alkylboron compound. In another aspect, the present application is directed to a process comprising: contacting a linear internal alkene, a hydrogen-boron bond containing compound, and an α-diimine metal complex under conditions suitable to form a terminal alkylboron compound. The α-diimine metal complexes, olefin and/or olefins (or alkenes), hydrogen-boron bond containing compounds, alkylboron compounds, conditions capable of forming alkylboron compounds, conditions capable of forming terminal alkylboron compounds, and other process features are independently described herein. These independently described features can be utilized in any combination and without limitation to further describe the processes described herein. It should be noted that while these features can be disclosed under headings within this application, a heading does not limit the disclosure found therein. Additionally the various aspects and embodiments disclosed herein can be combined in any manner.

One aspect of the present disclosure involves α-diimine metal salt complexes. Generally, the α-diimine metal salt complexes can comprise an α-diimine and a metal salt. The α-diimine and the metal salt are independent elements of the α-diimine metal salt complexes. The α-diimine and the metal salt elements of the α-diimine metal salt complexes are independently disclosed herein and any aspect and/or any embodiment of these elements can be combined without limitation to further describe the α-diimine metal salt complexes contemplated by the present disclosure. It should be noted that the α-diimine metal salt complex can also be referred to as a metal salt complexed to an α-diimine.

Generally, the metal salt of the α-diimine metal salt complex can have the formula $MX_p$. Within the formula of the metal salt having the formula $MX_p$, X represents a monoanionic species and p represents the number of monoanionic species (or the metal oxidation state). Generally, the monoanionic species, X, and the number of anionic species (or the metal oxidation state), p, are independent elements of the metal salt and are independently described herein. The metal salt having the formula $MX_p$ can be described utilizing any aspect or embodiment of the monoanionic species described herein, and any aspect or embodiment of the number of monoanionic species (or metal oxidation states) described herein. In an embodiment, the metal salt can be an iron salt ($FeX_p$) or a cobalt salt ($CoX_p$). As such, in an embodiment, the α-diimine metal salt complex can be an α-diimine iron salt complex or an α-diimine cobalt salt complex.

Generally, the number of monoanionic species (or the metal oxidation state) of the iron salt or the cobalt salt of α-diimine metal salt complex can be any positive value that corresponds to an oxidation state available to the iron or cobalt atom. In an embodiment, the number of monoanionic species, p, of the iron salt or the cobalt salt of α-diimine metal salt complex can be 1, 2 or 3; alternatively, 2 or 3; alternatively, 1; alternatively, 2; or alternatively, 3.

The monoanionic species, X, of the iron salt or the cobalt salt of α-diimine metal salt complex can be any anion. In some embodiments, the monoanionic species can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanionic species, X, of the iron salt or the cobalt salt of α-diimine metal salt complex can be a halide, a carboxylate, a β-diketonate, or an alkoxide; or alternatively, a halide or a β-diketonate. In other embodiments, the monoanionic species, X, of the iron salt or the cobalt salt of α-diimine metal salt complex can be a halide; alternatively, a carboxylate; alternatively, a β-diketonate; alternatively, a hydrocarboxide; alternatively, an alkoxide; alternatively an aralkoxide, or alternatively, an aryloxide. In some embodiments, the monoanionic species, X, of the metal salt of the iron salt or the cobalt salt of α-diimine metal salt complex can be a methylenetrihydrocarbylsilyl anion.

Generally, each halide monoanionic species, X, of the iron salt or the cobalt salt of an α-diimine metal salt complex independently can be fluorine, chlorine, bromine, or iodine; or alternatively, chlorine, bromine, or iodine. In an embodiment, each halide monoanionic species, X, of the iron salt or the cobalt salt of the α-diimine metal salt complex independently can be chloride, bromide, or iodide; alternatively, chloride; or alternatively, bromide. In an embodiment, each carboxylate of the iron salt or the cobalt salt of α-diimine metal salt complex can be a $C_1$ to $C_{20}$ carboxylate; alternatively, a $C_1$ to $C_{10}$ carboxylate; alternatively, acetate; alternatively, 2-ethylhexanoate; or alternatively, triflate. In an embodiment, each β-diketonate of the iron salt or the cobalt salt of α-diimine metal salt complex can be a $C_1$ to $C_{20}$ β-diketonate; alternatively, a $C_1$ to $C_{10}$ β-diketonate; or alternatively, acetylacetonate. In an embodiment, each hydrocarboxide of the iron salt or the cobalt salt of α-diimine metal salt complex can be a $C_1$ to $C_{20}$ hydrocarboxide; or alternatively, a $C_1$ to $C_{10}$ hydrocarboxide. In an embodiment, the methylenetrihydrocarbylsilyl anion can be a $C_1$ to $C_{20}$ methylenetrihydrocarbylsilyl anion; or alternatively, a $C_1$ to $C_{10}$ methylenetrihydrocarbylsilyl anion. In some embodiments, each hydrocarbyl group of the methylenetrihydrocarbylsilyl anion independently can be a methyl group, an ethyl group, a propyl group, or a phenyl group; alternatively, a methyl group; alternatively, an ethyl group; alternatively, a propyl group; or alternatively, a phenyl group. In an embodiment, the methylenetrihydrocarbylsilyl anion can be a methylenetrimethylsilyl anion.

In an embodiment, the iron salt of the α-diimine iron salt complex can be iron(II) chloride, iron(III) chloride, iron (II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(II) triflate, or iron(I) methylenetrimethylsilyl; alternatively, be iron(II) chloride, iron(III) chloride, iron(II) acetate, iron (III) acetate, iron(II) acetylacetonate, or iron(III) acetylacetonate; alternatively, iron(II) chloride or iron(II) acetylacetonate; alternatively, iron(II) chloride; alternatively, iron(II) acetylacetonate; or alternatively, iron(I) methylenetrimethylsilyl. In an embodiment, the cobalt salt of the α-diimine cobalt salt complex can be cobalt(II) chloride, cobalt(III) chloride, cobalt(II) fluoride, cobalt(III) fluoride, cobalt (II) bromide, cobalt(III) bromide, cobalt(II) iodide, cobalt(III) iodide, cobalt(II) acetate, cobalt (III) acetate, cobalt(II) acetylacetonate, cobalt(II) benzoylacetonate, cobalt(III) acetylacetonate, cobalt(II) 2-ethylhexanoate, cobalt (II) triflate, or cobalt(I) methylenetrimethylsilyl; alternatively, cobalt(II) chloride, cobalt(III) chloride, cobalt(II) acetate, cobalt (III) acetate, or cobalt(II) acetylacetonate; alternatively, cobalt (II) chloride; alternatively, cobalt(II) acetylacetonate; or alternatively, cobalt(I) methylenetrimethylsilyl.

Generally, the α-diimine can be described as comprising i) an α-diimine group, ii) a first imine nitrogen group attached to a first imine nitrogen atom of the α-diimine group, and iii) a second imine nitrogen group attached to a second imine nitrogen atom of the α-diimine group. The α-diimine group, first imine nitrogen group, and second imine nitrogen group are independent elements of the α-diimine and each of these elements are independently described herein. The independent elements of the α-diimine can used without limitation, and in any combination, to further describe the α-diimine and the α-diimine element of the α-diimine metal salt complex.

In an embodiment, the first imine nitrogen group attached to a first imine nitrogen atom of the α-diimine group and the second imine nitrogen group attached to a second imine nitrogen atom of the α-diimine group independently can be an organyl group; an organyl group consisting of inert functional groups; or a hydrocarbyl group. In an embodiment, the first imine nitrogen group comprising an organyl group attached to a first imine nitrogen atom of the α-diimine group and the second imine nitrogen group comprising an organyl group attached to a second imine nitrogen atom of the α-diimine group independently can be an organyl group; alternatively, an organyl group consisting essentially of inert functional groups; or alternatively, a hydrocarbyl group. Generally, the first imine group and the second imine group independently can be saturated, unsaturated, linear, branched, acyclic, cyclic, aromatic, and/or heteroaromatic. In an embodiment, the organyl group(s) attached to the first imine nitrogen atom and/or the second imine nitrogen atom of the α-diimine group of any α-diimine having organyl groups independently can be a $C_1$ to $C_{30}$, a $C_1$ to $C_{20}$, a $C_1$ to $C_{15}$, or a $C_1$ to $C_{10}$ organyl group. In an embodiment, the organyl group(s) consisting essentially of inert functional groups attached to the first imine nitrogen atom and/or the second imine nitrogen atom of the α-diimine group of any α-diimine having organyl groups consisting essentially of inert functional groups independently can be a $C_1$ to $C_{30}$, a $C_1$ to $C_{20}$, a $C_1$ to $C_{15}$, or a $C_1$ to $C_{10}$ organyl group consisting essentially of inert functional groups. In an embodiment, the hydrocarbyl group(s) attached to the first imine nitrogen atom and/or the second imine nitrogen atom of the α-diimine group of any α-diimine having hydrocarbyl groups independently can be a $C_1$ to $C_{30}$, a $C_1$ to $C_{20}$, a $C_1$ to $C_{15}$, or a $C_1$ to $C_{10}$ hydrocarbyl group.

In some embodiments, the organyl group consisting essentially of inert functional groups can be an aromatic ring or aromatic ring system having one or more inert functional group substituent(s). In these embodiments, the aromatic ring or aromatic ring system can be a substituted benzene ring (a substituted phenyl group); or alternatively, a substituted naphthalene ring (a substituted naphthyl group). The substituents of the aromatic ring or aromatic ring system having one or more inert functional group substituent(s) can be a halogen atom, an ether group (alkoxy group or etheryl group), or a sulfide group (sulfidyl group). In some embodiments, the aromatic ring having one or more inert functional group substituent(s) can be a trifluoromethyl group, a $C_1$ to $C_5$ ether group, a $C_1$ to $C_5$ sulfide group, or a halogen atom. In some embodiments, the halogen atom can be fluorine, chlorine, bromine or iodine; alternatively, chlorine; or alternatively, fluorine. In some embodiments, the alkoxy group can be a methoxy group; alternatively, an ethoxy group; alternatively, an isopropoxy group; or alternatively, a tert-butoxy group.

In some embodiments, the aromatic hydrocarbyl group can be a phenyl group, a substituted phenyl group, a naphthyl group, a substituted naphthyl group, a benzyl group, or a substituted benzyl group. In other embodiments, the aromatic hydrocarbyl group can be a phenyl group, a naphthyl group, or a benzyl group. In yet other embodiments, the aromatic hydrocarbyl group can be a phenyl group; alternatively, a naphthyl group; or alternatively, a benzyl group. In further embodiments, the aromatic hydrocarbyl group can be a substituted phenyl group; alternatively, a substituted naphthyl group; or alternatively, a substituted benzyl group.

In an aspect, the α-diimine of the α-diimine metal complex can be a bidentate α-diimine or a tridentate α-diimine; alternatively, a bidentate α-diimine; or alternatively, a tridentate α-diimine. It should be noted that the tridentate α-diimine description does not necessarily imply that all of the ligating elements of the tridentate α-diimine are complexed to the metal salt. Generally, a bidentate α-diimine will have a first imine group and a second imine group which are independently selected from an organyl group consisting essentially of inert functional groups and a hydrocarbyl group. Thus, when the α-diimine is a bidentate α-diimine, the bidentate α-diimine can comprise i) an α-diimine group, ii) a first imine nitrogen group comprising an organyl group consisting essentially of inert functional groups (or a hydrocarbyl group) attached to a first imine nitrogen atom of the α-diimine group and iii) a second imine nitrogen group comprising an organyl group consisting essentially of inert functional groups (or a hydrocarbyl group) attached to a second imine nitrogen atom of the α-diimine group.

Generally, a tridentate α-diimine will have a first imine group selected from an organyl group consisting essentially of inert functional groups and a hydrocarbyl group while the second imine group is an organyl group. When the α-diimine is a tridentate α-diimine, the organyl group which is the second imine group can be described as a second imine group comprising (1) a metal complexing group and (2) a linking group linking the metal complexing group to a second imine nitrogen atom of the α-diimine group. Thus, in some embodiments, the tridentate α-diimine can comprise i) an α-diimine group, ii) a first imine nitrogen group comprising an organyl group consisting essentially of inert functional groups (or a hydrocarbyl group) attached to a first imine nitrogen atom of the α-diimine group, and iii) a second imine nitrogen group comprising (1) a metal complexing group and (2) a linking group linking the metal complexing group to a second imine nitrogen atom of the α-diimine group.

In an embodiment, the first imine nitrogen group and/or the second imine nitrogen group independently can be an acyclic group having any number of carbon atoms disclosed herein for imine nitrogen groups. The first imine nitrogen group and/or the second imine nitrogen group can be a linear acyclic group or a branched acyclic group; alternatively, a linear acyclic group; or alternatively, a branched acyclic group. In an embodiment, the first imine nitrogen group and/or the second imine nitrogen group independently can be a methyl group, an ethyl group, a propyl group, a butyl group, or a pentyl group. In some embodiments, the first imine nitrogen group and/or the second imine nitrogen group independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group.

In an embodiment, the first imine nitrogen group and/or the second imine nitrogen group independently can be cyclic. In some embodiments, the cyclic group which can be the first imine nitrogen group and/or the second imine nitrogen group can be aliphatic or aromatic; alternatively, aliphatic; or alternatively, aromatic. In an embodiment, the aliphatic cyclic group which can be the first imine nitrogen group and/or the second imine nitrogen group can be a $C_4$ to $C_{30}$, a $C_4$ to $C_{20}$, or a $C_4$ to $C_{10}$ aliphatic cyclic group.

In an embodiment, the aliphatic cyclic group which can be the first imine nitrogen group and/or the second imine nitrogen group can be a $C_4$ to $C_{30}$ cyclic hydrocarbyl group or a substituted $C_4$ to $C_{30}$ cyclic hydrocarbyl group; alternatively, a $C_4$ to $C_{20}$ cyclic hydrocarbyl group or a substituted $C_4$ to $C_{20}$ cyclic hydrocarbyl group; alternatively, a $C_4$ to $C_{10}$ cyclic hydrocarbyl group or a substituted $C_4$ to $C_{10}$ cyclic hydrocarbyl group; alternatively, a $C_4$ to $C_{30}$ cyclic hydrocarbyl group; alternatively, a $C_4$ to $C_{20}$ cyclic aliphatic cyclic group hydrocarbyl group; or alternatively, a $C_4$ to $C_{10}$ cyclic hydrocarbyl group. In some embodiments, the aliphatic cyclic group which can be the first imine nitrogen group and/or the second imine nitrogen group can be a cyclopentyl group, a substituted cyclopentyl group, a cyclohexyl group, a substituted cyclohexyl group, an adamantyl group, or a substituted adamantyl group; or alternatively, a cyclopentyl group, a substituted cyclopentyl group, a cyclohexyl group, or a substituted cyclohexyl group. In other embodiments, the aliphatic cyclic group which can be the first imine nitrogen group and/or the second imine nitrogen group can be a cyclopentyl group or a substituted cyclopentyl group; alternatively, a cyclohexyl group or a substituted cyclohexyl group; alternatively, a cyclopentyl group or a cyclohexyl group; alternatively, a cyclopentyl group; or alternatively, a cyclohexyl group. Each substituent of any substituted aliphatic cyclic group which can be the first imine nitrogen group and/or the second imine nitrogen group described herein can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups, and hydrocarboxy groups that can be utilized as substituents are independently disclosed herein and can be utilized without limitation, and in any combination, to further describe a substituted aliphatic cyclic group which can be utilized as the first imine nitrogen group and/or the second imine nitrogen group of an α-diimine.

In an embodiment, the cyclic group which can be the first imine nitrogen group and/or the second imine nitrogen group can be an aromatic group. The aromatic group can be a $C_6$ to $C_{30}$, a $C_6$ to $C_{20}$, or a $C_6$ to $C_{10}$ aromatic group. In some embodiments, the aromatic group which can be the first imine nitrogen group and/or the second imine nitrogen group can be a phenyl group or a substituted phenyl group, a naphthyl group, or a substituted naphthyl group; alternatively, a phenyl group, a substituted phenyl group; alternatively, a phenyl group; or alternatively, a substituted phenyl group. Each substituent of any substituted aromatic group which can be the first imine nitrogen group and/or the second imine nitrogen group described herein can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups, and hydrocarboxy groups that can be utilized as substituents are independently disclosed herein and can be utilized without limitation, and in any combination, to further describe a substituted aromatic group which can be utilized as the first imine nitrogen group and/or the second imine nitrogen group of an α-diimine.

In an embodiment, each substituted phenyl group which can be the first imine nitrogen group and/or the second imine nitrogen group can be a phenyl group, a substituted phenyl group comprising a substituent at the 2-position, a substituted phenyl group comprising a substituent at the 3-position, a substituted phenyl group comprising a substituent at the 4-position, a substituted phenyl group comprising substituents at the 2- and 3-positions, a substituted phenyl group comprising substituents at the 2- and 4-positions, a substituted phenyl group comprising substituents at the 2- and 5-positions, a substituted phenyl group comprising substituents at the 3- and 5-positions, a substituted phenyl group comprising substituents at the 2- and 6-positions, or a substituted phenyl group comprising substituents at the 2-, 4-, and 6-positions; alternatively, a substituted phenyl group comprising a substituent at the 2-position, a substituted phenyl group comprising a substituent at the 4-position, a substituted phenyl group comprising substituents at the 2- and 4-positions, a substituted phenyl group comprising substituents at the 2- and 6-positions, or a substituted phenyl group comprising substituents at the 2-, 4-, and 6-position; alternatively, a substituted phenyl group comprising substituents at the 2- and 6-positions or a substituted phenyl group comprising substituents at the 2-, a 4-, and 6-positions; alternatively, a substituted phenyl group comprising a substituent at the 2-position; alternatively, a substituted phenyl group comprising a substituent at the 3-position; alternatively, a substituted phenyl group comprising a substituent at the 4-position; alternatively, a substituted phenyl group comprising substituents at the 2- and 3-positions; alternatively, a substituted phenyl group comprising substituents at the 2- and 4-positions; alternatively, a substituted phenyl group comprising substituents at the 2- and 5-positions; alternatively, a substituted phenyl group comprising substituents at the 3- and 5-positions; alternatively, a substituted phenyl group comprising substituents at the 2- and a 6-position; or alternatively, a substituted phenyl group comprising substituents at the 2-, 4-, and 6-positions. In some embodiments, each substituted phenyl group which can be the first imine nitrogen group and/or the second imine nitrogen group can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubsituted phenyl group; alternatively, a 2-substituted phenyl group, a 4-substituted phenyl group, a 2,4-disubstituted phenyl group, a 2,6-disubstituted phenyl group, or a 2,4,6-trisubsituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubsituted phenyl group. Each substituent of any substituted phenyl group which can be the first imine nitrogen group and/or the second imine nitrogen group described herein can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups, and hydrocarboxy groups that can be utilized as substituents are independently disclosed herein and can be utilized without limitation, and in any combination, to further describe a substituted phenyl group which can be utilized as the first imine nitrogen group and/or the second imine nitrogen group of an α-diimine.

In a particular embodiment, the substituted phenyl groups which can be the first imine nitrogen group and/or the second imine nitrogen group can be a 2,6-dimethyl, a 2,6-diethyl group, a 2,6-diisopropyl group, or a 2,6-di-tert-butyl group, a 2-isopropyl-6-methyl group, or a 2,4,6-trimethyl group. In some particular embodiments, the substituted phenyl groups which can be the first imine nitrogen group and/or the second imine nitrogen group can be a 2,6-dimethyl group, a 2,6-diethyl group, or a 2,6-diisopropyl group; alternatively, a 2,6-dimethyl group; alternatively, a 2,6-diethyl group; alternatively, a 2,6-diisopropyl group; alternatively, a 2,6-di-tert-butyl group; alternatively, a 2,5-di-tert-butyl group; alternatively, a 2-isopropyl-6-methyl group; or alternatively, a 2,4,6-trimethyl group.

In a tridentate α-diimine embodiment, the second imine nitrogen group can comprise (1) a metal complexing group and (2) a linking group linking the metal complexing group to a second imine nitrogen atom of the α-diimine group. Generally, the metal complexing group and the linking group linking the metal complexing group to the second imine nitrogen atom of the α-diimine group are independent elements of the second imine nitrogen group comprising a metal complexing group and a linking group linking the metal complexing group to the second imine nitrogen atom of the α-diimine group. As such, the metal complexing group and the linking group are independently described herein and these independent descriptions can used without limitation, and in any combination, to further describe the second imine nitrogen group comprising (1) a metal complexing group and (2) a linking group linking the metal complexing group to the second imine nitrogen atom of the α-diimine group of the α-diimine.

Generally, the metal salt complexing group can be any group comprising a heteroatom capable of complexing with the metal salt and the linking group can be any group capable of linking the metal salt complexing group to the second imine nitrogen atom of the α-diimine group. The linking group includes all atoms between the second imine nitrogen atom and the metal salt complexing group. If the metal salt complexing group is acyclic, the linking group includes all atoms between the second imine nitrogen atom and the heteroatom of the metal salt complexing functional group. For example, in an N,N-dimethylethylene group, the linking group is —$CH_2CH_2$— and the metal salt complexing group is the N,N-dimethylaminyl group, while in a 2-phenoxyethyl group the linking group is —$CH_2CH_2$— and the metal salt complexing group is the phenoxy group. However, if the heteroatom of the metal salt complexing group is contained within a ring, the linking group includes all the atoms between the second imine nitrogen atom and the first atom contained within the ring containing the metal salt complexing heteroatom of the metal salt complexing group. For example, in a 2-ethylpyridinyl group the linking group is —$CH_2CH_2$— and the metal salt complexing group is the 2-pyridinyl group, while in 1-ethylpiperidinyl group the linking group is —$CH_2CH_2$— and the metal salt complexing group is the 1-piperidinyl group.

The metal salt complexing group can be any group comprising a heteroatom capable of complexing with the metal salt. In an embodiment, the metal salt complexing group can be a $C_2$ to $C_{30}$, a $C_2$ to $C_{20}$, a $C_2$ to $C_{10}$, or a $C_2$ to $C_5$ group comprising a heteroatom capable of complexing with the metal salt. In some embodiments, the metal salt complexing heteroatom of the metal salt complexing group can be an oxygen, sulfur, nitrogen, or phosphorus; alternatively, oxygen or sulfur; or alternatively, nitrogen or phosphorus. In other embodiments, the metal salt complexing heteroatom of the metal salt complexing group can be oxygen; alternatively, sulfur; alternatively, nitrogen; or alternatively, phosphorus. Optionally, the metal salt complexing group can contain additional heteroatoms which do not complex the metal salt in α-diimine metal complex such as inert heteroatoms (e.g. halides, and silicon) and/or additional metal salt complexing heteroatom(s) which do not complex with the metal salt.

In particular embodiments, the metal salt complexing group can be a dialkyl aminyl group, a diphenyl aminyl group, a di(substituted phenyl) aminyl group, an (alkyl)(phenyl) aminyl group, an (alkyl)(substituted phenyl) aminyl group, a dialkyl phosphinyl group, a diphenyl phosphinyl group, a di(substituted phenyl) phosphinyl group, an (alkyl)(phenyl) phosphinyl group, an (alkyl)(substituted phenyl) phosphinyl group, an alkyl etheryl group, a phenyl etheryl group, a substituted phenyl etheryl group, an alkyl sulfidyl group, a phenyl sulfidyl group, a substituted phenyl sulfidyl group, a furanyl group, a substituted furanyl group, a thiophenyl group, a substituted thiophenyl group, a tetrahydrofuranyl group, a substituted tetrahydrofuranyl group, a thiophanyl group, a substituted thiophanyl group, a pyridinyl group, a substituted pyridinyl group, a morphilinyl group, a substituted morphilinyl group, a pyranyl group, a substituted pyranyl group, a tetrahydropyranyl group, a substituted tetrahydropyranyl group, a quinolinyl group, a substituted quinolinyl group, a pyrrolyl group, a substituted pyrrolyl group, a pyrrolidinyl group, a substituted pyrrolidinyl group, a piperidinyl group, or a substituted piperidinyl group. In embodiments, the metal salt complexing group can be a dialkyl aminyl group, a diphenyl aminyl group, a dialkyl phosphinyl group, a diphenyl phosphinyl group, an alkyl etheryl group, a phenyl etheryl group, an alkyl sulfidyl group, a phenyl sulfidyl group, a furanyl group, a thiophenyl group, a tetrahydrofuranyl group, a thiophanyl group, a pyridinyl group, a morphilinyl group, a pyranyl group, a tetrahydropyranyl group, a quinolinyl group, a pyrrolyl group, a pyrrolidinyl group, or a piperidinyl group. In some embodiments, the metal salt complexing group can be a dialkyl aminyl group, a diphenyl aminyl group, a di(substituted phenyl) aminyl group, a dialkyl phosphinyl group, a diphenyl phosphinyl group, a di(substituted phenyl) phosphinyl group, an alkyl etheryl group, a phenyl etheryl group, a substituted phenyl etheryl group, an alkyl sulfidyl group, a phenyl sulfidyl group, a substituted phenyl sulfidyl group, a pyridinyl group, a substituted pyridinyl group, a morphilinyl group, or a substituted morphilinyl group; alternatively, a dialkyl aminyl group, a diphenyl aminyl group, a dialkyl phosphinyl group, a diphenyl phosphinyl group, an alkyl etheryl group, a phenyl etheryl group, an alkyl sulfidyl group, a phenyl sulfidyl group, a pyridinyl group, or a morphilinyl group; alternatively, a dialkyl aminyl group, a diphenyl aminyl group, a di(substituted phenyl) aminyl group, a dialkyl phosphinyl group, a diphenyl phosphinyl group, or a di(substituted phenyl) phosphinyl group; alternatively, a dialkyl aminyl group, a diphenyl aminyl group, a dialkyl phosphinyl group, a diphenyl phosphinyl group; or alternatively, a diphenyl aminyl group, a di(substituted phenyl) aminyl group, a diphenyl phosphinyl group, a di(substituted phenyl) phosphinyl group; alternatively, a diphenyl aminyl group, a di(substituted phenyl) aminyl group, a diphenyl phosphinyl group, a di(substituted phenyl) phosphinyl group, a phenyl sulfidyl group, a substituted phenyl sulfidyl group, a pyridinyl group, or a substituted pyridinyl group; or alternatively, a diphenyl aminyl group, a diphenyl phosphinyl group, a phenyl sulfidyl group, or a pyridinyl group. In other embodiments, the metal salt complexing group can be a dialkyl aminyl group or a dialkyl phosphinyl group; alternatively, a diphenyl aminyl group or a diphenyl phosphinyl group; alternatively, a di(substituted phenyl) aminyl group or a di(substituted phenyl) phosphinyl group; alternatively, a 2-pyridinyl group or a substituted 2-pyridinyl group; alternatively, an alkyl etheryl group, a phenyl etheryl group, a substituted phenyl etheryl group, an alkyl sulfidyl group, a phenyl sulfidyl group, or a substituted sulfidyl group; alternatively, an alkyl etheryl group or an alkyl sulfidyl group; alternatively, a phenyl etheryl group, a substituted phenyl etheryl group, a phenyl sulfidyl group, or a substituted sulfidyl group; alternatively, a phenyl etheryl group or a substituted phenyl etheryl group; alternatively, a phenyl sulfidyl group or a substituted phenyl sulfidyl group;

alternatively, a phenyl sulfidyl group; alternatively, a substituted phenyl sulfidyl group; alternatively, a furanyl group, a substituted furanyl group, a thiophenyl group or a substituted thiophenyl group; alternatively, a 1-morphilinyl group or a substituted 1-morphilinyl group; alternatively, a 2-morphilinyl group or a substituted 2-morphilinyl group; alternatively, a 2-pyranyl group or a substituted 2-pyranyl group; alternatively, a 2-tetrahydropyranyl group or a substituted 2-tetrahydropyranyl group; alternatively, a 1-piperidinyl group, or a substituted 1-piperidinyl group; alternatively, a 1-pyrrolidinyl group or a substituted 1-pyrrolidinyl group; alternatively, a 2-pyrrolidinyl group, a substituted 2-pyrrolidinyl group; alternatively, a 2-piperidinyl group, or a substituted 2-piperidinyl group; alternatively, a 2-quinolinyl group or a substituted 2-quiolinyl group; alternatively, a 1-pyrrolyl group or a substituted 1-pyrrolyl group; alternatively, a 2-pyrrolyl group or a substituted 2-pyrrolyl group; alternatively, a 2-tetrahydrofuranyl group or a substituted 2-tetrahydrofuranyl group; or alternatively, a 2-thiophanyl group or a substituted 2-thiophanyl group. In yet other embodiments, the metal salt complexing group can be a diphenyl aminyl group; alternatively, a di(substituted phenyl) aminyl group; alternatively, a diphenyl phosphinyl group; or alternatively, a di(substituted phenyl) phosphinyl group.

Each alkyl group of any aminyl, phosphinyl, ethyl, or sulfidyl metal salt complexing group having an alkyl group independently can be a $C_1$ to $C_{20}$, a $C_1$ to $C_{10}$, or a $C_1$ to $C_5$ alkyl group. In an embodiment, each alkyl group of any aminyl, phosphinyl, ethyl, or sulfidyl metal salt complexing group having an alkyl group independently can be a methyl group, an ethyl group, a propyl group, a butyl group, or a pentyl group; alternatively, a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group.

Each substituted phenyl group of any aminyl, phosphinyl, ethyl, or sulfidyl metal salt complexing group having a substituted phenyl group independently can be a $C_6$ to $C_{20}$, or a $C_6$ to $C_{15}$ substituted phenyl group. Additionally, each substituent of any substituted phenyl group or any substituted metal salt complexing group independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups, and hydrocarboxy groups that can be utilized as substituents are independently disclosed herein and can be utilized without limitation, and in any combination, to further describe a substituted phenyl group or substituted metal complexing group.

The linking group linking the metal salt complexing group to the second imine nitrogen atom of the α-diimine group can be a bond or an organyl group; alternatively, a bond or an organyl group consisting essentially of inert functional groups; alternatively, a bond or a hydrocarbyl group; alternatively, an organyl group; alternatively, an organyl group consisting essentially of inert functional groups; alternatively, a hydrocarbyl group; or alternatively, a bond. In an embodiment, the organyl groups which can be utilized as the linking group linking the metal salt complexing group to the second imine nitrogen atom of the α-diimine group can be a $C_1$ to $C_{15}$, a $C_1$ to $C_{10}$, or a $C_1$ to $C_5$ organyl group. In an embodiment, the organyl groups consisting essentially of inert functional groups which can be utilized as the linking group linking the metal salt complexing group to the second imine nitrogen atom of the α-diimine group can be a $C_1$ to $C_{15}$, a $C_1$ to $C_{10}$, or a $C_1$ to $C_5$ organyl group consisting essentially of inert functional groups. In an embodiment, the hydrocarbyl groups which can be utilized as the linking group linking the metal salt complexing group to the second imine nitrogen atom of the α-diimine group can be a $C_1$ to $C_{15}$, a $C_1$ to $C_{10}$, or a $C_1$ to $C_5$ hydrocarbyl group. In some other embodiments, the linking group which can be utilized as the linking group linking the metal salt complexing group to the second imine nitrogen atom of the α-diimine group can be a $C_1$ to $C_{15}$, a $C_1$ to $C_{10}$, or a $C_1$ to $C_5$ alkyl group.

In an embodiment, the linking group linking group linking the metal salt complexing group to the second imine nitrogen atom of the α-diimine group can be $-(CR^L)_m-$ or a phenyl-1,2-ene group. Within the structure $-(CR^L)_m-$, each $R^L$ independently can be hydrogen, methyl, ethyl, propyl, isopropyl, or butyl groups and m can be an integer from 1 to 5. In some embodiments, the linking group can be a methylene group, an eth-1,2-ylene group, a prop-1,3-ylene group, a butyl-1,3-ene group, a dimethylmethylene group, a butyl-1,4-ene group or a phen-1,2-ylene group. In some non-limiting embodiments, the linking group can be a methylene group, an eth-1,2-ylene group, a prop-1,3-ylene group, or a phen-1,2-ylene group; alternatively, an eth-1,2-ylene group, or a prop-1,3-ylene group; alternatively, a methylene group; alternatively, an eth-1,2-ylene group; alternatively, a prop-1,3-ylene group; or alternatively, a phen-1,2-ylene group.

In a non-limiting embodiment, a second imine group comprising (1) a metal complexing group and (2) a linking group linking the metal complexing group to a second imine nitrogen atom of the α-diimine group can be a 2-(1-pyrrolidinyl)ethyl group, a 2-(2-piperdinyl)ethyl group, a 1-(2-piperidinyl)ethyl group, a 2-(2-pyrrolidinyl)ethyl group, a 2-(N,N-dimethylaminyl)ethyl group, a 2-(N,N-diethylaminyl)ethyl group, a 2-(N,N-diphenylaminyl)ethyl group, a (2-pyridinyl)methyl group, a 2-(2-pyridinyl)ethyl group, a 2-(diphenylphosphinyl)ethyl group, a 3-(diphenylphosphinyl)propyl group, a 2-(2-furanyl)ethyl group, a (2-furanyl)methyl group, a 2-(2-thiophenyl)ethyl group, a (2-thiophenyl)methyl group, a 2-(phenylsulfidyl)ethyl group, a 2-((4-chlorophenyl)sulfidyl group, a 2-phenoxyethyl group, a 2-methoxyethyl group, a 2-ethoxyethyl group, and a 2-isopropoxyethyl group. In some non-limiting embodiments, the second imine group comprising (1) a metal complexing group and (2) a linking group linking the metal complexing group to a second imine nitrogen atom of the α-diimine group can be a 2-(N,N-dimethylaminyl)ethyl group, a 2-(N,N-diethylaminyl)ethyl group, a 2-(N,N-diphenylaminyl) ethyl group, a (2-pyridinyl)methyl group, a 2-(2-pyridinyl) ethyl group, a 2-(diphenylphosphinyl)ethyl group, a 3-(diphenylphosphinyl)propyl group, a 2-(phenylsulfidyl) ethyl group), a 2-((4-chlorophenyl)sulfidyl group, a 2-phenoxyethyl group, a 2-methoxyethyl group, a 2-ethoxyethyl group, or a 2-isopropoxyethyl group; alternatively, a 2-(N, N-dimethylaminyl)ethyl group, a 2-(N,N-diethylaminyl) ethyl group, or a 2-(N,N-diphenylaminyl)ethyl group; alternatively, a 2-(diphenylphosphinyl)ethyl group or a 3-(diphenylphosphinyl)propyl group; alternatively, a (2-pyridinyl)methyl group or a 2-(2-pyridinyl)ethyl group; alternatively, a 2-(phenylsulfidyl)ethyl group or a 2-((4-chlorophenyl)sulfidyl group; or alternatively, a 2-phenoxyethyl group, a 2-methoxyethyl group, a 2-ethoxyethyl group, or a 2-isopropoxyethyl group. In other non-limiting embodiments, the second imine group comprising (1) a metal complexing group and (2) a linking group linking the metal complexing group to a second imine nitrogen atom of the α-diimine group can be a 2-(N,N-dimethylaminyl)ethyl group; alternatively, a 2-(N,N-diethylaminyl)ethyl group; alternatively, a 2-(N,N-diphenylaminyl)ethyl group; alternatively, a (2-pyridinyl)methyl group; alternatively, a 2-(2-pyridinyl)ethyl group; alternatively, a 2-(diphenylphosphinyl)ethyl group; alternatively, a 3-(diphenylphosphinyl)propyl group; alternatively, a 2-(phenylsulfidyl)ethyl group; or alternatively, a 2-((4-chlorophenyl)sulfidyl group.

Generally, the α-diimine can be derived from α-diacyl compounds; or alternatively, an α-dione (a compound wherein two ketone oxygen atoms are bonded to adjacent carbon atoms). The α-diacyl compounds (or α-diones) can be any α-diacyl compounds (or α-dione) capable of forming an α-diimine. Consequently, in some embodiments, the α-diimine of the α-diimine metal salt complex can be described as comprising i) an α-diimine group derived from an α-diacyl compound, ii) a first imine nitrogen group attached to a first imine nitrogen atom of the α-diimine group, and iii) a second imine nitrogen group attached to a second imine nitrogen atom of the α-diimine group; or alternatively, the α-diimine of the α-diimine metal salt complex can be described as comprising i) an α-diimine group derived from an α-dione, ii) a first imine nitrogen group attached to a first imine nitrogen atom of the α-diimine group, and iii) a second imine nitrogen group attached to a second imine nitrogen atom of the α-diimine group. The α-diacyl compound (or α-dione) can be saturated, unsaturated, acyclic, cyclic, linear, branched, aromatic, and/or heteroaromatic. In an embodiment, the α-diacyl compound (or α-dione), whether it is aliphatic or aromatic and/or cyclic or acyclic, can be a $C_4$ to $C_{60}$ α-diacyl compound (or $C_4$ to $C_{60}$ α-dione), a $C_4$ to $C_{45}$ α-diacyl compound (or $C_4$ to $C_{45}$ α-dione), a $C_4$ to $C_{30}$ α-diacyl compound (or $C_4$ to $C_{30}$ α-dione), or $C_4$ to $C_{20}$ α-diacyl compound (or $C_4$ to $C_{20}$ α-dione).

Generally, the α-dione will have the structure $R^{k1}$—C(=O)—C(=O)—$R^{k2}$. In an embodiment, $R^{k1}$ and $R^{k2}$ independently can be an organyl group; alternatively, an organyl group consisting of inert functional groups; or alternatively, a hydrocarbyl group. In an embodiment, the organyl groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ organyl group. In an embodiment, the organyl groups consisting of inert functional groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ hydrocarbyl group. In yet other embodiments, the hydrocarbyl groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ alkyl group.

In an embodiment, the α-dione can be an acyclic α-dione, a semicyclic α-dione, or a cyclic α-dione; alternatively, an acyclic α-dione; alternatively, a semicyclic α-dione; or alternatively, a cyclic α-dione. When the α-dione is an acyclic α-dione, both $R^{k1}$ and $R^{k2}$ are acyclic. When the α-dione is a semi-cyclic α-dione, $R^{k1}$ and/or $R^{k2}$ are or can comprise a cyclic structure wherein $R^{k1}$ and/or $R^{k2}$ are not connected to form a ring or ring system containing both ketone carbon atoms of the α-dione group. When the α-dione is a cyclic α-dione, $R^{k1}$ and $R^{k2}$ are connected to form a ring or ring system containing both ketone carbon atoms of the α-dione group. In some semi-cyclic and/or cyclic α-dione embodiments, the ring or ring system can be saturated. In other semi-cyclic and/or cyclic α-dione embodiments, the ring or ring system can contain carbon-carbon double (and/or triple) bonds. In further semi-cyclic and/or cyclic α-dione embodiments, the ring system can be a bicyclic ring system. In yet other semi-cyclic and/or cyclic α-dione embodiments, the ring or ring system can comprise an aromatic ring or an aromatic ring structure.

In an acyclic α-dione embodiment, the α-dione can be 2,3-butanedione, a substituted 2,3-butanedione, 2,3-pentanedione, a substituted 2,3-pentanedione, 2,3-hexanedione, a substituted 2,3-hexanedione, 3,4-hexanedione, or a substituted 3,4-hexanedione. In some embodiments, the α-dione can be 2,3-butanedione, 2,3-pentanedione, 2,3-hexanedione, or 3,4-hexanedione. In further embodiments, the α-dione can be 2,3-butanedione; alternatively, 2,3-pentanedione; alternatively, 2,3-hexanedione; or alternatively, 3,4-hexanedione.

In an aromatic semi-cyclic α-dione embodiment, the α-dione can be benzyl or a substituted benzyl. In other embodiments, the α-dione can be benzyl.

In a saturated cyclic α-dione embodiment, the α-dione can be 1,2-cyclobutanedione, a substituted 1,2-cyclobutanedione, 1,2-cyclopentanedione, a substituted 1,2-cyclopentanedione, 1,2-cyclohexanedione, a substituted 1,2-cyclohexanedione, 1,2-cycloheptanedione, or a substituted 1,2-cycloheptanedione. In some saturated cyclic α-dione embodiments, the α-dione can be 1,2-cyclopentanedione, a substituted 1,2-cyclopentanedione, 1,2-cyclohexanedione, or a substituted 1,2-cyclohexanedione. In some saturated cyclic α-dione embodiments, the α-dione can be 1,2-cyclopentanedione, or 1,2-cyclohexanedione. In yet other embodiments, the α-dione can be 1,2-cyclopentanedione; or alternatively, 1,2-cyclohexanedione.

In saturated ring system α-dione embodiments, the α-dione can be bicyclo[2.2.1]hepta-1,2-dione, a substituted bicyclo[2.2.1]hepta-1,2-dione, bicyclo[2.2.2]octa-1,2-dione, or a substituted bicyclo[2.2.2]octa-1,2-dione, or camphorquinone. In some saturated ring system embodiments, the α-dione can be bicyclo[2.2.1]hepta-1,2-dione, bicyclo[2.2.2]octa-1,2-dione, or camphorquinone. In yet other saturated ring system α-dione embodiments, the α-dione can be camphorquinone.

In unsaturated cyclic α-dione embodiments, the α-dione can be 1,2-benzoquinone, a substituted 1,2-benzoquinone, cyclohex-3-ene-1,2-dione, a substituted cyclohex-3-ene-1,2-dione, cyclopent-3-ene-1,2-dione, a substituted cyclopent-3-ene-1,2-dione, a cyclohex-4-ene-1,2-dione, a substituted cyclohex-4-ene-1,2-dione, 3,4-dihydro-1,2-naphthoquinone, a substituted 3,4-dihydro-1,2-naphthaquinone, 1,4-dihydronaphthoquinone, or a substituted 1,4-dihydronaphthoquinone. In some unsaturated cyclic α-dione embodiments, the α-dione can be 1,2-benzoquinone, cyclohex-3-ene-1,2-dione, cyclopent-3-ene-1,2-dione, cyclohex-4-ene-1,2-dione, 3,4-dihydronaphthoquinone, or 1,4-dihydronaphthoquinone. In other unsaturated ring α-dione embodiments, the α-dione can be 1,2-benzoquinone; alternatively, 3,4-dihydronaphthoquinone; or alternatively, 1,4-dihydronaphthanoquinone.

In aromatic ring system α-dione embodiments, the α-dione can be a 1,2-naphthoquinone, a substituted 1,2-naphthoquinone, 2,3-naphthoquinone, a substituted 2,3-naphthoquinone, acenaphthenequinone, a substituted acenaphthenequinone, phenanthrenequinone, a substituted phenanthrenequinone, pyrenequinone, or a substituted pyrenequinone. In some aromatic ring system α-dione embodiments, the α-dione can be 1,2-naphthoquinone, 2,3-naphthoquinone, acenaphthenequinone, phenanthrenequinone, or pyrenequinone. In other aromatic ring system α-dione embodiments, the α-dione can be acenaphthenequinone, phenanthrenequinone, or pyrenequinone. In yet other aromatic ring system α-dione embodiments, the α-dione can be 1,2-naphthoquinone; alternatively, 2,3-naphthoquinone; alternatively, acenaphthenequinone; alternatively, phenanthrenequinone; or alternatively, pyrenequinone.

Within any substituted α-dione embodiment, each substituent independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups, and hydrocarboxy substituent groups that can be utilized as substituents are independently disclosed herein and can be utilized without limitation, and in any combination, to further describe the substituent of any substituted α-dione described herein.

In some particular non-limiting embodiments, the α-diimine metal complex can have one of Structures I-XXXIX wherein the metal salt $X_p$ can be any metal salt disclosed herein.

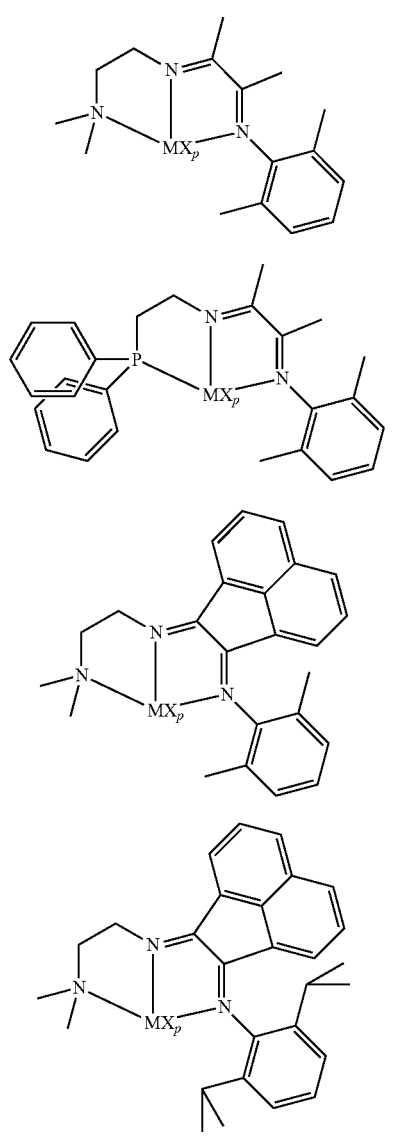

Structure I

Structure II

Structure III

Structure IV

-continued

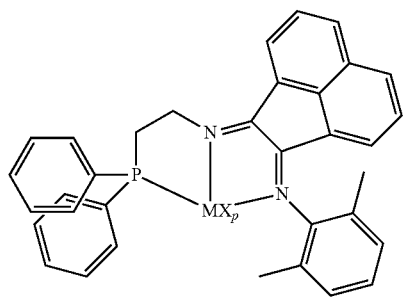

Structure V

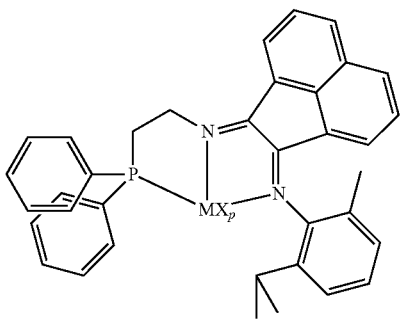

Structure VI

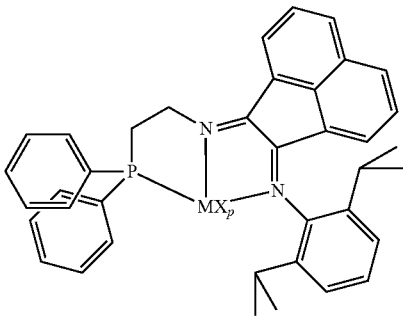

Structure VII

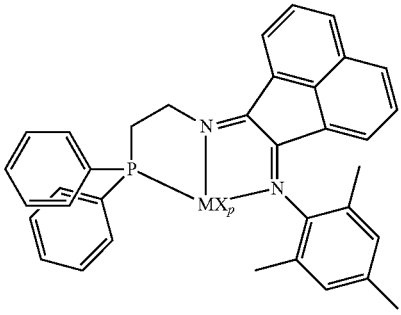

Structure VIII

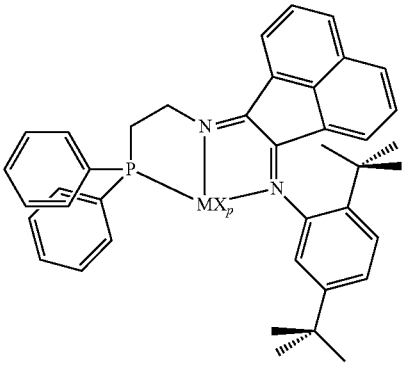

Structure IX

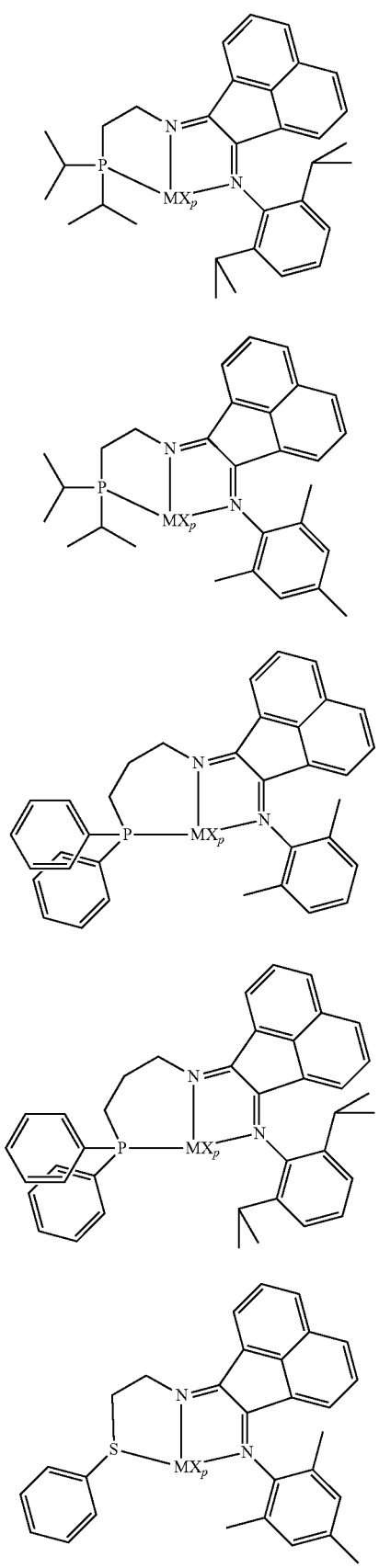
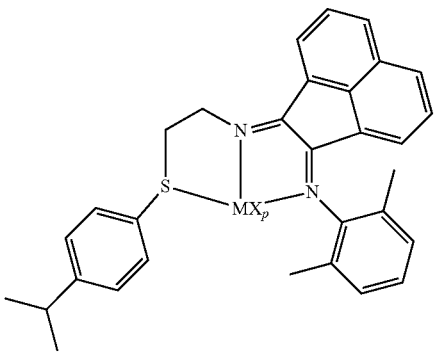

Structure XIX
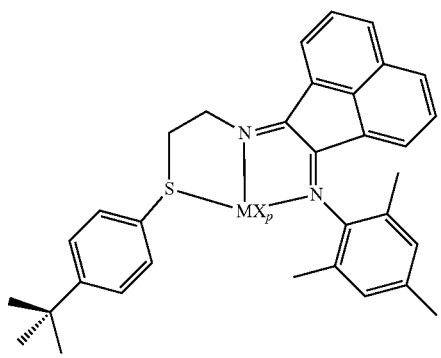
Structure XX
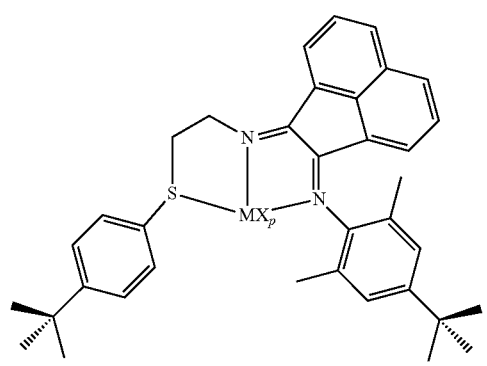
Structure XXI
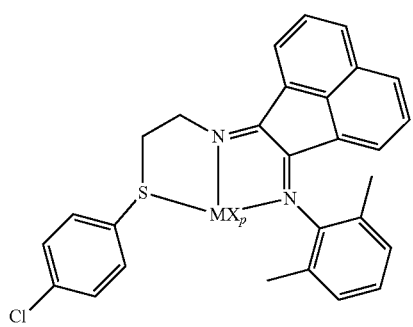
Structure XXII
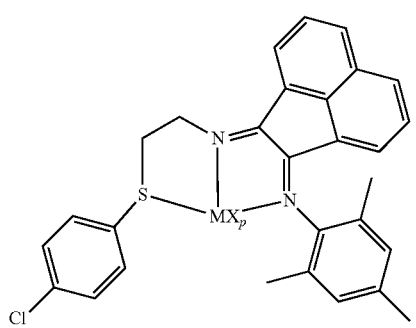
Structure XXIII
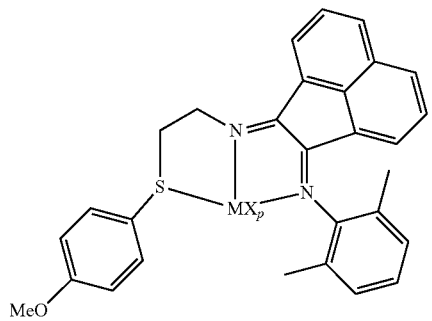
Structure XXIV
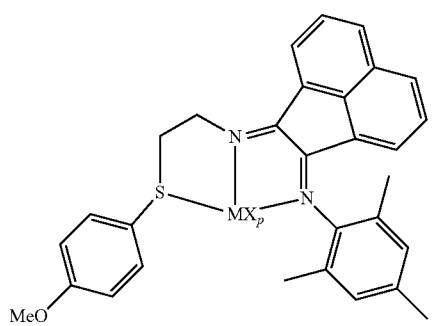
Structure XXV
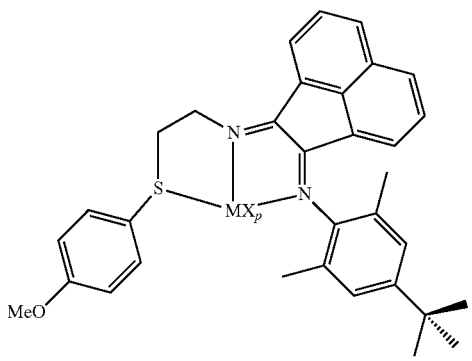
Structure XXVI
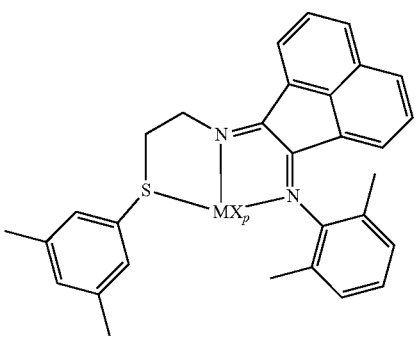

Structure XXVII
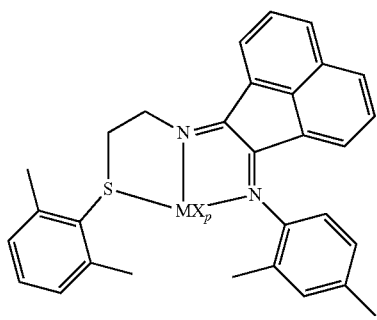
Structure XXVIII
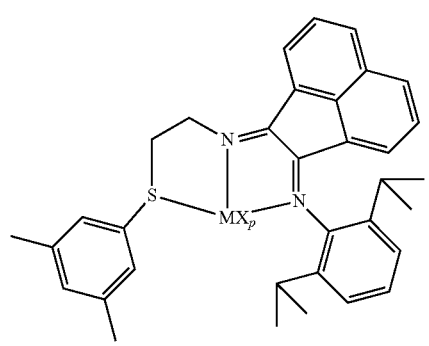
Structure XXIX
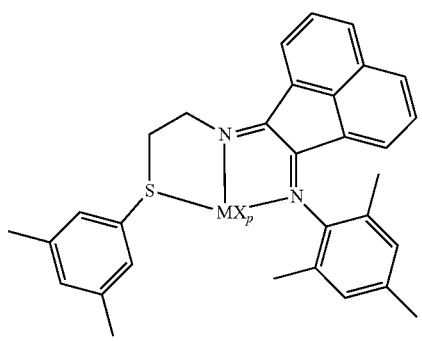
Structure XXX
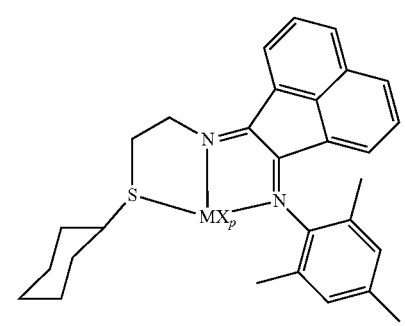
Structure XXXI
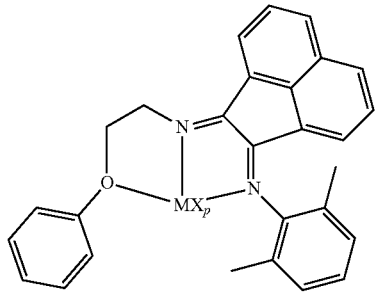
Structure XXXII
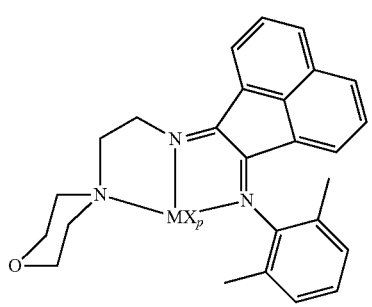
Structure XXXIII
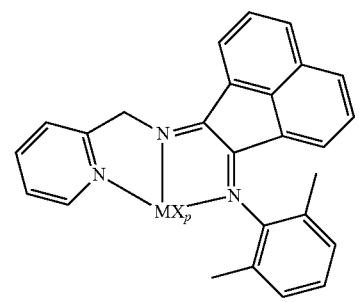
Structure XXXIV
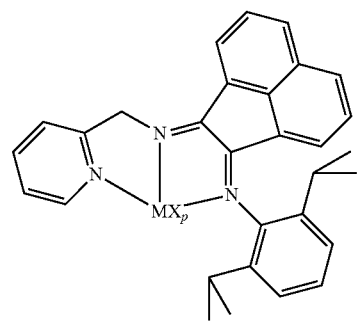
Structure XXXV
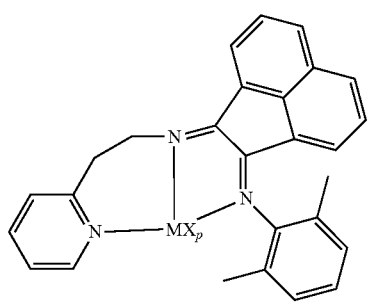

Structure XXXVI

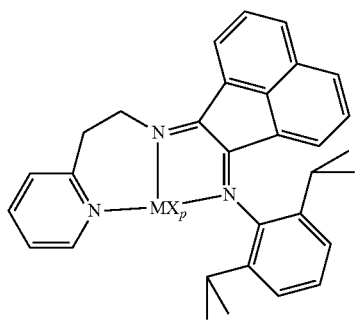

Structure XXXVII

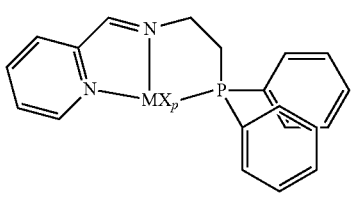

Structure XXXVIII

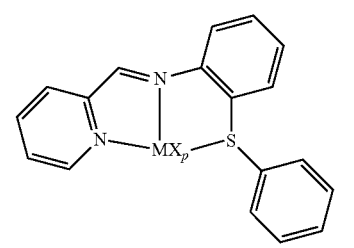

Structure XXXIX

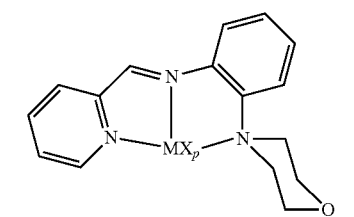

A wide range of olefins can be utilized in the process for the hydroboration of an olefin using a metal complex of the types disclosed herein. In some embodiments, the olefin can be an alkene. For example, the processes described herein can be applicable to olefins as small as propylene and as large as waxes having 70 or 75 carbon atoms per molecule. In any aspect and/or in any embodiment described herein, the olefin can comprise, or consist essentially of, or consist of, a $C_2$ to $C_{60}$, a $C_4$ to $C_{50}$, a $C_6$ to $C_{30}$, a $C_6$ to $C_{20}$ olefin; or a $C_6$ to $C_{14}$ olefin; alternatively, a $C_2$ to $C_{60}$, a $C_4$ to $C_{50}$, a $C_6$ to $C_{30}$, a $C_6$ to $C_{20}$, or a $C_6$ to $C_{14}$ alkene. In an embodiment, the olefin or alkene can comprise, consist essentially of, or consist of, a $C_6$, a $C_8$, a $C_{10}$, a $C_{12}$, a $C_{14}$, a $C_{16}$, a $C_{18}$ olefin (or alkene), or any combination thereof; alternatively, a $C_6$, a $C_8$, a $C_{10}$, a $C_{12}$, a $C_{14}$ olefin (or alkene), or any combination thereof; alternatively, a $C_6$ olefin (or alkene); alternatively, a $C_8$ olefin (or alkene); alternatively, a $C_{10}$ olefin (or alkene); alternatively, a $C_{12}$ olefin (or alkene); alternatively, a $C_{14}$ olefin (or alkene); alternatively, a $C_{16}$ olefin (or alkene); or alternatively, a $C_{18}$ olefin (or alkene).

In an embodiment, the olefin or alkene, regardless of carbon number, can be a terminal olefin (or alkene), an internal olefin (or alkene), or a combination thereof; alternatively, a terminal olefin (or alkene); or alternatively, an internal olefin (or alkene). Herein terminal olefin (e.g., terminal alkene) refers to an olefin in which the carbon-carbon pi bond is at the end of the carbon chain whereas an internal olefin (e.g., internal alkene) has the carbon-carbon pi bond disposed between carbons neither of which occurs at the end of the carbon chain. In some embodiments, the alkene (regardless of carbon number, and whether terminal and/or internal) can be a linear olefin (or alkene), a branched olefin (or alkene), or a combination thereof; alternatively, a linear olefin (or alkene); or alternatively, a branched olefin (or alkene). In other embodiments, the olefin (or alkene), regardless of carbon number and whether terminal or internal, and/or linear or branched, can be an acyclic olefin (or alkene), a cyclic olefin (or alkene), or any combination thereof; alternatively, an acyclic olefin (or alkene); or alternatively, a cyclic olefin (or alkene). In a particular embodiment, the olefin (or alkene), regardless of carbon number can comprise, consist essentially of, or consist of, a linear terminal alkene, a linear internal alkene, or any combination thereof; alternatively, a linear terminal alkene; or alternatively, a linear internal alkene.

In an embodiment, the olefin (or alkene) can comprise, consist essentially of, or consist of, an olefin (or alkene) having any carbon number described herein. In some embodiments, the alkene can comprise, consist essentially of, or consist of, a butene, a pentene, a hexene, a heptene, an octene, a nonene, a decene, an undecene, a dodecene, a tridecene, a tetradecene, a pentadecene, a hexadecene, a heptadecene, an octadecene, or a combination thereof; or alternatively, a hexene, an octene, a decene, a dodecene, a tetradecene, a hexadecene, an octadecene, or a combination thereof. In some embodiments, the alkene can comprise, consist essentially of, or consist of, 1-hexene, 1-octene, 1-decene, 1-dodecene, 1-tetradecene, 1-hexadecene, 1-octadecene, or a combination thereof; alternatively, 1-hexene, 1-octene, 1-decene, 1-dodecene, or a combination thereof; alternatively, 1-hexene; alternatively, 1-octene; alternatively, 1-decene; or alternatively, 1-dodecene. In other embodiments, the alkene can comprise, consist essentially of, or consist of, internal hexene(s), internal octene(s), internal decene(s), internal dodecene(s), internal tetradecene(s), internal hexadecene(s), internal octadecene(s), or a combination thereof; alternatively, internal hexene(s), internal octene(s), internal decene(s), internal dodecene(s), or a combination thereof; alternatively, internal hexene(s); alternatively, internal octene(s); alternatively, internal decene(s); or alternatively, internal dodecene(s). In yet other embodiments, the alkene can comprise, consist essentially of, or consist of, linear internal hexene(s), linear internal octene(s), linear internal decene(s), linear internal dodecene(s), linear internal tetradecene(s), linear internal hexadecene(s), linear internal octadecene(s), or a combination thereof; alternatively, linear internal hexene(s), linear internal octene(s), linear internal decene(s), linear internal dodecene(s), or a combination thereof; alternatively, linear internal hexene(s); alternatively, linear internal octene(s); alternatively, linear internal decene(s); or alternatively, linear internal dodecene(s). In some embodiments, any internal olefin (or alkene) describe herein can comprise, consist essentially of, of consist of, a cis-olefin (or alkene), a trans-olefin (or alkene), or any combination thereof; alternatively, a cis-olefin (or alkene); or alternatively, a trans-olefin (or alkene).

Generally, the hydrogen-boron bond containing compound can be any compound having a hydrogen-boron bond. In an aspect, the hydrogen-boron bond containing compound can comprise, consist essentially of, or consist of, borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborolidine, or any combination thereof. In some embodiments, the hydrogen-boron bond containing compound can comprise, consist essentially of, or consist of, borane, diborane, a borane-amine complex, a borane-phosphine complex, a borane-ether complex, a borane-sulfide complex, a hydrogen borinic acid ester, a hydrogen boronic acid ester, a hydrogen monoaminoborane, a hydrogen diaminoborane, or any combination thereof; alternatively, borane, diborane, a borane-amine complex, a borane-phosphine complex, a borane-ether complex, a borane-sulfide complex, a hydrogen borinic acid ester, a hydrogen boronic acid ester, or any combination thereof; alternatively, borane, diborane, a borane-amine complex, a borane-phosphine complex, a borane-ether complex, a borane-sulfide complex, or any combination thereof; alternatively, borane, diborane, or any combination thereof; alternatively, a borane-amine complex, a borane-phosphine complex, a borane-phosphite complex, a borane-ether complex, a borane-sulfide complex, or any combination thereof; a hydrogen borinic acid ester, a hydrogen boronic acid ester, a hydrogen monoaminoborane, a hydrogen diaminoborane, or any combination thereof; alternatively, a hydrogen borinic acid ester, a hydrogen boronic acid ester, or any combination thereof; or alternatively, a hydrogen monoaminoborane, a hydrogen diaminoborane, or any combination thereof. In other embodiments, the hydrogen-boron bond containing compound can comprise, consist essentially of, or consist of, borane; alternatively, diborane; alternatively, a borane-amine complex; alternatively, a borane-phosphine complex; alternatively, a borane-phosphite complex; alternatively, a borane-ether complex; alternatively, a borane-sulfide complex; alternatively, a hydrogen borinic acid ester; alternatively, a hydrogen boronic acid ester; alternatively, a hydrogen monoaminoborane; or alternatively, a hydrogen diaminoborane. In other embodiments, the hydrogen-boron bond containing compound can comprise, consist essentially of, or consist of, a hydrogen borinic thio acid ester or a hydrogen boronic thio acid ester; alternatively, a hydrogen borinic thio acid ester; or alternatively, a hydrogen boronic thio acid ester. In yet other embodiments, the hydrogen-boron bond containing compound can comprise, consist essentially of, or consist of, a borohydride compound salt. In some embodiments, the hydrogen-boron bond containing compound can comprise, consist essentially of, or consist of, a hydrogen borohalide, a hydroborohalide amine complex, a hydroborohalide phosphine complex, a hydroborohalide amine complex, a hydroborohalide ether complex, a hydroborohalide sulfide complex, or any combination thereof; alternatively, a hydroborohalide amine complex, a hydroborohalide phosphine complex, a hydroborohalide amine complex, a hydroborohalide ether complex, a hydroborohalide sulfide complex, or any combination thereof; alternatively, a hydrogen borohalide; alternatively, a hydroborohalide amine complex; alternatively, a hydroborohalide phosphine complex; alternatively, a hydroborohalide amine complex; alternatively, a hydroborohalide ether complex; or alternatively, a hydroborohalide sulfide complex.

In an embodiment, the borohydride compound salt can be represented by the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$; alternatively, $A^m[BH_4]^{-1}{}_n$; alternatively, $A^m[BH_3R^{b1}]^{-1}{}_n$; alternatively, $A^m[BH_2(R^{b1})_2]^{-1}{}_n$; or alternatively, $A^m[BH(R^{b1})_3]^{-1}{}_n$. Generally, A, $R^{b1}$ (when present), m, and n of the borohydride compound salt having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ are independent elements of the borohydride compound salt. These elements of the borohydride compound salt having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ are independently described herein and these independently described elements can be combined in any fashion to further describe borohydride compound salts contemplated by the present disclosure. Generally, A of the borohydride compound salts having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ can be any suitable cation having a charge, m, of +1 to +6; alternatively, +1 to +4; alternatively, +1 to +3, alternatively, +1 to +2; alternatively, +1; alternatively, +2, or alternatively, +3. In an embodiment of the borohydride compound salts having the formula $A^m[BH_3R^{b1}]^{-1}{}_n$, $A^m[BH_2(R^{b1})_2]^{-1}{}_n$, or $A^m[BH(R^{b1})_3]^{-1}{}_n$, the sum of m and n can be zero.

In an embodiment of the borohydride compound salts having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$, A can be a Group 1A element. In some embodiments, A can be lithium, sodium, or potassium; alternatively, lithium; alternatively sodium; or alternatively, potassium. In other borohydride compound salt embodiments, A can be beryllium, uranium, or aluminum; alternatively beryllium; alternatively, uranium; or alternatively, aluminum. In an aspect A can be a polyatomic cation. In yet other borohydride compound salt embodiments, A can be ammonium, phosphonium, fluoronium, tropylium, or guanidinium; alternatively, ammonium; alternatively, phosphonium; alternatively, fluoronium; alternatively, tropylium; or alternatively, guanidinum.

Generally, one or more, of each $R^{b1}$ of the borohydride compound salts having the $A^m[BH_3R^{b1}]^{-1}{}_n$, $A^m[BH_2(R^{b1})_2]^{-1}{}_n$, or $A^m[BH(R^{b1})_3]^{-1}{}_n$ independently can be an organyl group or organocarboxy group; alternatively, an organyl group; alternatively, a organocarboxy group; alternatively, a hydrocarbyl group or a hydrocarboxy group; alternatively, a hydrocarbyl group; or alternatively, a hydrocarboxy group. In an embodiment, each $R^{b1}$ of the borohydride compound salt independently can be a $C_1$ to $C_{30}$, a $C_1$ to $C_{20}$, a $C_1$ to $C_{15}$, a $C_1$ to $C_{10}$, or a $C_1$ to $C_6$ organyl group. In an embodiment, each $R^{b1}$ organocarboxy group of the borohydride compound salt independently can be a $C_1$ to $C_{30}$, a $C_1$ to $C_{20}$, a $C_1$ to $C_{15}$, a $C_1$ to $C_{10}$, or a $C_1$ to $C_6$ organocarboxy group. In an embodiment, each $R^{b1}$ hydrocarbyl group of the borohydride compound salt independently can be a $C_1$ to $C_{30}$, a $C_1$ to $C_{20}$, a $C_1$ to $C_{15}$, a $C_1$ to $C_{10}$, or a $C_1$ to $C_6$ hydrocarbyl group. In other embodiments each $R^{b1}$ hydrocarboxy group of the borohydride compound salt independently can be a $C_1$ to $C_{30}$, a $C_1$ to $C_{20}$, a $C_1$ to $C_{15}$, a $C_1$ to $C_{10}$, or a $C_1$ to $C_6$ hydrocarboxy group. In some embodiments, the $R^{b1}$ groups of $A^m[BH_2(R^{b1})_2]^{-1}{}_n$ can be the same; or alternatively, the $R^{b1}$ groups of $A^m[BH_2(R^{b1})_2]^{-1}{}_n$ can be different. In some embodiments of the borohydride compound salt having the formula $A^m[BH(R^{b1})_3]^{-1}{}_n$, all of the $R^{b1}$ groups of $A^m[BH(R^{b1})_3]_n$ can be the same; alternatively, two of the $R^{b1}$ groups of $A^m[BH(R^{b1})_3]^{-1}{}_n$ can be the same; or alternatively, all three of the $R^{b1}$ groups of $A^m[BH(R^{b1})_3]^{-1}{}_n$ can be different. In some embodiments of the borohydride compound salts having the formula $A^m[BH_2(R^{b1})_2]^{-1}{}_n$, the two $R^{b1}$ groups can be linked to form a ring or ring system (including bicyclic ring systems) containing the boron atom; in this instance, the joined $R^{b1}$ groups can be designated $R^{j1}$. In some embodiments of the borohydride compound salts having the A'''[BH(R$^{b1}$)$_3$]$^{-1}_n$, two (or alternatively three) of the R$^{b1}$ groups can be linked to form a ring or ring system (including bicyclic, tricyclic ring systems) containing the boron atom; in these instance two joined R$^{b1}$ groups can be designated R$^{j1}$, while three joined R$^{b1}$ groups can be designated R$^{j2}$.

In an embodiment, the hydrogen-boron bond containing compound can be represented by the formula H$_2$BR$^{b4}$ or HB(R$^{b4}$)$_2$; alternatively, H$_2$BR$^{b4}$; or alternatively, HB(R$^{b4}$)$_2$. Generally, one or more, or each R$^{b4}$ of the hydrogen-boron bond containing compound represented by the formula H$_2$BR$^{b4}$ or HB(R$^{b4}$)$_2$; alternatively, H$_2$BR$^{b4}$; or alternatively HB(R$^{b4}$)$_2$ independently can be an organyl group; or alternatively, a hydrocarbyl group. In an embodiment, one or more, or each organyl group R$^{b5}$ of the hydrogen-boron bond containing compound can be represented by the formula H$_2$BR$^{b4}$ or HB(R$^{b4}$)$_2$; alternatively, H$_2$BR$^{b4}$; or alternatively HB(R$^{b4}$)$_2$ independently can be a C$_1$ to C$_{15}$, a C$_1$ to C$_{10}$, or a C$_1$ to C$_6$ organyl group. In an embodiment, one or more, or each R$^{b4}$ hydrocarbyl group of the hydrogen-boron bond containing compound can be represented by the formula H$_2$BR$^{b4}$ or HB(R$^{b4}$)$_2$; alternatively, H$_2$BR$^{b4}$; or alternatively HB(R$^{b4}$)$_2$ independently can be a C$_1$ to C$_{15}$, a C$_1$ to C$_{10}$, or a C$_1$ to C$_6$ hydrocarbyl group. In some embodiments, the R$^{b4}$ groups of HB(R$^{b4}$)$_2$ can be the same; or alternatively, the R$^{b4}$ groups of HB(R$^{b4}$)$_2$ can be different. In an embodiment, the hydrogen-boron bond containing compound represented by the formula H$_2$BR$^{b4}$ can be a C$_1$ to C$_{15}$, a C$_1$ to C$_{10}$, or a C$_1$ to C$_6$ hydrogen-boron bond containing compound having the formula H$_2$BR$^{b4}$. In an embodiment, the hydrogen-boron bond containing compound represented by the formula HB(R$^{b4}$)$_2$ can be a C$_2$ to C$_{30}$, a C$_2$ to C$_{20}$, or a C$_2$ to C$_{12}$ hydrogen-boron bond containing compound having the formula HB(R$^{b4}$)$_2$. In some embodiments where the hydrogen-boron bond containing compound has the formula HB(R$^{b4}$)$_2$, the two R$^{b4}$ groups can be the same; or alternatively, the two R$^{b4}$ groups can be different. In some embodiments where the hydrogen-boron bond containing compound has the formula HB(R$^{b4}$)$_2$, the two R$^{b4}$ groups of HB(R$^{b4}$)$_2$ can be joined to form a ring or ring system containing the boron atom. In this instance, the two linked R$^{b4}$ groups can be designated R$^{j3}$.

In an embodiment, the hydroborohalide can be represented by the formula H$_2$BX or HBX$_2$; alternatively, H$_2$BX; or alternatively, HBX$_2$. In some embodiments, the hydroborohalide can be represented by the formula HB(R$^{b4}$)X. Generally, each X of the hydroborohalide having the formula H$_2$BX, HBX$_2$, and/or HB(R$^{b4}$)X independently can be any halide. In some embodiments, each X of the hydroborohalide having the formula H$_2$BX or HBX$_2$ independently can be fluoride, chloride, bromide, iodide; alternatively, chloride or bromide; alternatively, chloride; alternatively, bromide; or alternatively, iodide. Generally, the R$^{b4}$ group of the hydroborohalide having the formula HB(R$^{b4}$)X can be any appropriate R$^{b4}$ described herein (e.g., any R$^{b4}$ group described herein for the hydrogen-boron bond containing compound having the formula H$_2$BR$^{b4}$ and/or HB(R$^{b4}$)$_2$).

In an aspect, the hydrogen-boron bond containing compound can be a neutral ligand complexed hydrogen-boron bond containing compound. In an embodiment, the neutral ligand of the neutral ligand complexed hydrogen-boron bond containing compound can be an amine, a phosphine, an ether, a sulfide, or any combination thereof; alternatively, an amine; alternatively, a phosphine; alternatively, an ether; or alternatively, a sulfide. These neutral ligand complexed hydrogen-boron bond containing compounds can be designated by the formula NL-BH where NL can represent any neutral ligand or any neutral structure provide herein and BH can represent a hydrogen-boron bond containing compound described herein or any hydrogen-boron bond containing compound having the formula BH$_3$, H$_2$BR$^{b4}$, HB(R$^{b4}$)$_2$, H$_2$BX, and/or HBX$_2$ (e.g., a hydrogen-boron bond containing compound having the formula BH$_3$, H$_2$BR$^{b4}$, HB(R$^{b4}$)$_2$, H$_2$BX, or HBX$_2$; alternatively, H$_2$BR$^{b4}$ or HB(R$^{b4}$)$_2$; alternatively, H$_2$BX or HBX$_2$; alternatively, BH$_3$; alternatively, H$_2$BR$^{b4}$; alternatively, HB(R$^{b4}$)$_2$; alternatively, H$_2$BX; or alternatively, HBX$_2$. BH$_3$, H$_2$BR$^{b4}$, HB(R$^{b4}$)$_2$, H$_2$BX, or HBX$_2$; alternatively, H$_2$BR$^{b4}$ or HB(R$^{b4}$)$_2$; alternatively, H$_2$BX or HBX$_2$; alternatively, BH$_3$; alternatively, H$_2$BR$^{b4}$; alternatively, HB(R$^{b4}$)$_2$; alternatively, H$_2$BX; or alternatively, HBX$_2$). The neutral ligand complexed hydrogen-boron bond containing compound can be further represented by replacing NL with any general or specific neutral ligand provided herein or any general or specific ligand formula provided herein and/or replacing BH with any hydrogen-boron bond containing compound provided herein or general or specific hydrogen-boron bond containing compound formula provided herein. For example, one general amine-hydroborohalide complex can be designated as amine-BH$_3$, a tertiary amine-borane complex can be represented as [(R$^{b5}$)$_3$N]BH$_3$, and a trimethylamine-borane complex can be represented by the formula [(CH$_3$)$_3$N]BH$_3$. As a second example, one general sulfide-hydroborohalide complex can be designated as a sulfide-BH$_2$X, a less general sulfide-hydroborohalide complex can be represented as [(R$^{b8}$)$_2$S]BH$_2$X, and a dimethysulfide-monochloride borane complex can be represented by the formula [(CH$_3$)$_2$S]BH$_2$Cl. Other, general and specific neutral ligand complexed hydrogen-boron bond containing compounds designation can be readily envisioned and used.

In an embodiment, a hydrogen-boron bond containing compound-amine complex can be represented by the formula [(R$^{b5}$)$_q$NH$_{3-q}$]BH$_3$. In an embodiment, a hydrogen-boron bond containing compound-amine complex can be represented by the formula [(R$^{b5}$)$_q$NH$_{3-q}$]BH$_2$R$^{b4}$ or [(R$^{b5}$)$_q$NH$_{3-q}$]BH(R$^{b4}$)$_2$; alternatively, [(R$^{b5}$)$_q$NH$_{3-q}$]BH$_2$R$^{b4}$; or alternatively, [(R$^{b5}$)$_q$NH$_{3-q}$]BH(R$^{b4}$)$_2$. In the formulas [(R$^{b5}$)$_q$NH$_{3-q}$]BH$_2$R$^{b4}$ and [(R$^{b5}$)$_q$NH$_{3-q}$]BH(R$^{b4}$)$_2$, q can be an integer ranging from 0 to 3; alternatively, 0, alternatively 1; alternatively, 2; or alternatively, 3. In an embodiment, a borane-amine complex can be represented by the formula [(R$^{b5}$)$_q$NH$_{3-q}$]HB(R$^{b4}$)X. Generally, in the formulas [(R$^{b5}$)$_q$NH$_{3-q}$]BH$_2$R$^{b4}$ [(R$^{b5}$)$_q$NH$_{3-q}$]BH(R$^{b4}$)$_2$, and/or [(R$^{b5}$)$_q$NH$_{3-q}$]HB(R$^{b4}$)X, R$^{b4}$ can be any group described herein for the hydrogen-boron bond containing compound represented by the formulas H$_2$BR$^{b4}$ and/or HB(R$^{b4}$)$_2$. Further, the H$_2$BR$^{b4}$, HB(R$^{b4}$)$_2$, or HB(R$^{b4}$)X portion of the borane-amine complex can be any compound having the formula H$_2$BR$^{b4}$, HB(R$^{b4}$)$_2$, HB(R$^{b4}$)X described and/or provided herein. In an embodiment, a hydroborohalide-amine complex can be represented by the formula [(R$^{b5}$)$_r$NH$_{3-r}$]BH$_2$X or [(R$^{b5}$)$_r$NH$_{3-r}$]BHX$_2$; alternatively, [(R$^{b5}$)$_r$NH$_{3-r}$]BH$_2$X; alternatively, [(R$^{b5}$)$_r$NH$_{3-r}$]BHX$_2$; or alternatively, [(R$^{b5}$)$_q$NH$_{3-q}$]HB(R$^{b4}$)X. In the formulas [(R$^{b5}$)$_r$NH$_{3-r}$]BH$_2$X or [(R$^{b5}$)$_r$NH$_{3-r}$]BHX$_2$, r can be an integer ranging from 0 to 3; alternatively, 0, alternatively 1; alternatively, 2; or alternatively, 3. Additionally, in the formulas [(R$^{b5}$)$_r$NH$_{3-r}$]BH$_2$X, [(R$^{b5}$)$_r$NH$_{3-r}$]BHX$_2$, and [(R$^{b5}$)$_q$NH$_{3-q}$]HB(R$^{b4}$)X, X can be any halide described herein for the hydroborohalide compound represented by the formulas BH$_2$X and/or BHX$_2$, or BH$_2$X and/or BHX$_2$ can be any compound having the formula BH$_2$X or BHX$_2$ described and/or provided herein. In an embodiment, the amine of amine complexes can be NH$_3$ (i.e., [(R$^{b5}$)$_q$NH$_{3-q}$] or [(R$^{b5}$)$_r$NH$_{3-r}$] where q and r are 0. In an embodiment where the amine has the formula $R^{b5}NH_2$ (i.e., $[(R^{b5})_qNH_{3-q}]$ or $[(R^{b5})_rNH_{3-r}]$ where q and r are 1, the amine of the amine complexes can be a $C_1$ to $C_{15}$, a $C_1$ to $C_{10}$, or a $C_1$ to $C_6$ amine. In an embodiment where the amine has the formula $(R^{b5})_2NH$ (i.e., $[(R^{b5})_qNH_{3-q}]$ or $[(R^{b5})_rNH_{3-r}]$ where q and r are 2, the amine of the amine complexes can be a $C_2$ to $C_{30}$, a $C_2$ to $C_{20}$, or a $C_2$ to $C_{12}$ amine. In an embodiment where the amine has the formula $(R^{b5})_3N$ (i.e., $[(R^{b5})_qNH_{3-q}]$ or $[(R^{b5})_rNH_{3-r}]$ where q and r are 3, the amine of the amine complexes can be a $C_3$ to $C_{45}$, a $C_3$ to $C_{30}$, or a $C_3$ to $C_{18}$ amine. Generally, each $R^{b5}$ of the amine complexes independently can be an organyl group; or alternatively, a hydrocarbyl group. In an embodiment, each $R^{b5}$ organyl group of the amine complexes independently can be a $C_1$ to $C_{15}$, a $C_1$ to $C_{10}$, or a $C_1$ to $C_6$ organyl group. In an embodiment, each $R^{b5}$ hydrocarbyl group of the amine complexes independently can be a $C_1$ to $C_{15}$, a $C_1$ to $C_{10}$, or a $C_1$ to $C_6$ hydrocarbyl group. In some amine complex embodiments where the amine has the formula $(R^{b5})_2NH$ (i.e., $[(R^{b5})_qNH_{3-q}]$ or $[(R^{b5})_rNH_{3-r}]$ where q and r are 2, the two $R^{b5}$ groups can be the same; or alternatively, the two $R^{b5}$ groups can be different. In some amine complex embodiments where the amine has the formula $(R^{b5})_3N$ (i.e., $[(R^{b5})_qNH_{3-q}]$ or $[(R^{b5})_rNH_{3-r}]$ where q and r are 3, all of the $R^{b5}$ groups can be the same; alternatively, two of the $R^{b5}$ groups can be the same and the third $R^{b5}$ different; or alternatively, all three of the $R^{b5}$ groups can be different. In some amine complex embodiments where the amine has the formula $(R^{b5})_2NH$ (i.e., $[(R^{b5})_qNH_{3-q}]$ or $[(R^{b5})_rNH_{3-r}]$ where q and r are 2, the two $R^{b5}$ groups can be linked to form a ring or ring system (including bicyclic ring systems) containing the amine nitrogen atom; in this instance the two linked $R^{b5}$ groups can be designated $R^{j2}$. In some amine complex embodiments where the amine has the formula $(R^{b5})_3N$ (i.e., $[(R^{b5})_qNH_{3-q}]$ or $[(R^{b5})_rNH_{3-r}]$ where q and r are 3, two or three $R^{b5}$ groups can be linked to form a ring or ring system (including bicyclic, tricyclic ring systems) containing the amine nitrogen atom; in these instances two linked $R^{b5}$ groups can be designated $R^{j4}$ while three linked $R^{b5}$ groups can be designated $R^{j5}$. In an embodiment, three joined $R^{b5}$ groups can be joined to form a pyridine compound.

In an embodiment, a hydrogen-boron bond containing compound-phosphine complex can be represented by the formula $[(R^{b6})_qPH_{3-q}]BH_3$. In an embodiment, a hydrogen-boron bond containing compound-phosphine complex can be represented by the formula $[(R^{b6})_qPH_{3-q}]BH_2R^{b4}$ or $[(R^{b6})_qPH_{3-q}]BH(R^{b4})_2$; alternatively, $[(R^{b6})_qPH_{3-q}]BH_2R^{b4}$; or alternatively, $[(R^{b6})_qPH_{3-q}]BH(R^{b4})_2$. In the formulas $[(R^{b6})_qPH_{3-q}]BH_2R^{b4}$ and $[(R^{b6})_qPH_{3-q}]BH(R^{b4})_2$, q can be an integer ranging from 0 to 3; alternatively, 0, alternatively 1; alternatively, 2; or alternatively, 3. In an embodiment, a borane-phosphine complex can be represented by the formula $[(R^{b6})_qPH_{3-q}]HB(R^{b4})X$. Generally, in the formulas $[(R^{b6})_qPH_{3-q}]BH_2R^{b4}$, $[(R^{b6})_qPH_{3-q}]BH(R^{b4})_2$, and/or $[(R^{b6})_qPH_{3-q}]HB(R^{b4})X$, $R^{b4}$ can be any group described herein for the hydrogen-boron bond containing compound represented by the formulas $H_2BR^{b4}$ and/or $HB(R^{b4})_2$. Further, the $H_2BR^{b4}$, $HB(R^{b4})_2$, or $HB(R^{b4})X$ portion of the borane-phosphine complex can be any compound having the formula $H_2BR^{b4}$, $HB(R^{b4})_2$, or $HB(R^{b4})X$ described and/or provided herein. In an embodiment, a hydroborohalide-phosphine complex can be represented by the formula $[(R^{b6})_rPH_{3-r}]BH_2X$ or $[(R^{b6})_rPH_{3-r}]BHX_2$; alternatively, $[(R^{b6})_rPH_{3-r}]BH_2X$; alternatively, $[(R^{b6})_rPH_{3-r}]BHX_2$; or alternatively, $[(R^{b6})_qPH_{3-q}]HB(R^{b4})X$. In the formulas $[(R^{b6})_rPH_{3-r}]BH_2X$ or $[(R^{b6})_rPH_{3-r}]BHX_2$, r can be an integer ranging from 0 to 3; alternatively, 0, alternatively 1; alternatively, 2; or alternatively, 3. Additionally, in the formulas $[(R^{b6})_rPH_{3-r}]BH_2X$, $[(R^{b6})_rPH_{3-r}]BHX_2$, and $[(R^{b6})_qPH_{3-q}]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the phosphine of the phosphine complexes can be $PH_3$ (i.e., $[(R^{b6})_qPH_{3-q}]$ or $[(R^{b6})_rPH_{3-r}]$ where q and r are 0. In an embodiment where the phosphine has the formula $R^{b6}PH_2$ (i.e., $[(R^{b6})_qPH_{3-q}]$ or $[(R^{b6})_rPH_{3-r}]$ where q and r are 1, the phosphine of the phosphine complexes can be a $C_1$ to $C_{15}$, a $C_1$ to $C_{10}$, or a $C_1$ to $C_6$ phosphine. In an embodiment where the phosphine has the formula $(R^{b6})_2PH$ (i.e., $[(R^{b6})_qPH_{3-q}]$ or $[(R^{b6})_rPH_{3-r}]$ where q and r are 2, the phosphine of the phosphine complexes can be a $C_2$ to $C_{30}$, a $C_2$ to $C_{20}$, or a $C_2$ to $C_{12}$ phosphine. In an embodiment where the phosphine has the formula $(R^{b6})_3P$ (i.e., $[(R^{b6})_qPH_{3-q}]$ or $[(R^{b6})_rPH_{3-r}]$ where q and r are 3, the phosphine of the phosphine complexes can be a $C_3$ to $C_{45}$, a $C_3$ to $C_{30}$, or a $C_3$ to $C_{18}$ phosphine. Generally, each $R^{b6}$ of the phosphine complexes independently can be an organyl group; or alternatively, a hydrocarbyl group. In an embodiment, each $R^{b6}$ organyl group of the phosphine complexes independently can be a $C_1$ to $C_{15}$, a $C_1$ to $C_{10}$, or a $C_1$ to $C_6$ organyl group. In an embodiment, each $R^{b6}$ hydrocarbyl group of the phosphine complexes independently can be a $C_1$ to $C_{15}$, a $C_1$ to $C_{10}$, or a $C_1$ to $C_6$ hydrocarbyl group. In some phosphine complex embodiments where the phosphine has the formula $(R^{b6})_2PH$ (i.e., $[(R^{b6})_qPH_{3-q}]$ or $[(R^{b6})_rPH_{3-r}]$ where q and r are 2, the two $R^{b6}$ groups can be the same; or alternatively, the two $R^{b6}$ groups can be different. In some phosphine complex embodiments where the phosphine has the formula $(R^{b6})_3P$ (i.e., $[(R^{b6})_qPH_{3-q}]$ or $[(R^{b6})_rPH_{3-r}]$ where q and r are 3, all of the $R^{b6}$ groups can be the same; alternatively, two of the $R^{b6}$ groups can be the same and the third $R^{b6}$ group different; or alternatively, all three of the $R^{b6}$ groups of can be different. In some phosphine complex embodiments where the phosphine has the formula $(R^{b6})_2PH$ (i.e., $[(R^{b6})_qPH_{3-q}]$ or $[(R^{b6})_rPH_{3-r}]$ where q and r are 2, the two $R^{b6}$ groups can be linked to form a ring or ring system (including bicyclic ring systems) containing the phosphine phosphorous atom; in this instance the two linked $R^{b6}$ groups can be designated $R^{j4}$. In some phosphine complex embodiments where the phosphine has the formula $(R^{b6})_3P$ (i.e., $[(R^{b6})_qPH_{3-q}]$ or $[(R^{b6})_rPH_{3-r}]$ where q and r are 3), two or three $R^{b6}$ groups can be linked to form a ring or ring system (including bicyclic, tricyclic ring systems) containing the phosphine phosphorous atom; in these instances the two linked $R^{b6}$ groups can be designated $R^{j6}$ while three linked $R^{b6}$ groups can be designated $R^{j7}$.

In an aspect, the hydrogen-boron bond containing compound can be a hydrogen-boron bond containing compound-trihalophosphine complex. In an embodiment, a borane-trihalophosphine complex can be represented by the formula $[(X^1)_3P]BH_3$. In an embodiment, a hydrogen-boron bond containing compound-trihalophosphine complex can be represented by the formula $[(X^1)_3P]BH_2R^{b4}$ or $[(X^1)_3P]BH(R^{b4})_2$; alternatively, $[(X^1)_3P]BH_2R^{b4}$; or alternatively, $[(X^1)_3P]BH(R^{b4})_2$. In the formulas $[(X^1)_3P]BH_2R^{b4}$ and $[(X^1)_3P]BH(R^{b4})_2$, $R^{b4}$ can be any group described herein for the hydrogen-boron bond containing compound represented by the formulas $H_2BR^{b4}$ and/or $HB(R^{b4})_2$, or $H_2BR^{b4}$ and/or $HB(R^{b4})_2$ can be any compound having the formula $H_2BR^{b4}$ or $HB(R^{b4})_2$ described and/or provided herein. In an embodiment, a hydroborohalide-trihalophosphine complex can be represented by the formula $[(X^1)_3P]BH_2X$ or $[(X^1)_3P]BHX_2$; alternatively, $[(X^1)_3P]BH_2X$; or alternatively, $[(X^1)_3P]BHX_2$. In the formulas $[(X^1)_3P]BH_2X$ or $[(X^1)_3P]BHX_2$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, each $X^1$ of the hydrogen-boron bond containing compound-trihalophosphine complexes independently can be any halo group. In some embodiments, each $X^1$ of the hydrogen-boron bond containing compound-trihalophoshine complexes independently can be fluoro, chloro, bromo, or iodo; or alternatively, fluoro.

In an embodiment, a hydrogen-boron bond containing compound-phosphite complex can be represented by the formula $[(R^{b7}O)_3P]BH_3$. In an embodiment, a hydrogen-boron bond containing compound-phosphite complex can be represented by the formula $[(R^{b7}O)_3P]BH_2R^{b4}$ or $[(R^{b7}O)_3P]BH(R^{b4})_2$; alternatively, $[(R^{b7}O)_3P]BH_2R^{b4}$; or alternatively, $[(R^{b7}O)_3P]BH(R^{b4})_2$. In the formulas $[(R^{b7}O)_3P]BH_2R^{b4}$ and $[(R^{b7}O)_3P]BH(R^{b4})_2$, $R^{b4}$ can be any group described herein for the hydrogen-boron bond containing compound represented by the formulas $H_2BR^{b4}$ and/or $HB(R^{b4})_2$, or $H_2BR^{b4}$ and/or $HB(R^{b4})_2$ can be any compound having the formula $H_2BR^{b4}$ or $HB(R^{b4})_2$ described and/or provided herein. In an embodiment, a hydroborohalide-phosphite complex can be represented by the formula $[(R^{b7}O)_3P]BH_2X$ or $[(R^{b7}O)_3P]BHX_2$; alternatively, $[(R^{b7}O)_3P]BH_2X$; or alternatively, $[(R^{b7}O)_3P]BHX_2$. In the formulas $[(R^{b7}O)_3P]BH_2X$ or $[(R^{b7}O)_3P]BHX_2$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the phosphite of the phosphite complexes can be a $C_3$ to $C_{45}$, a $C_3$ to $C_{30}$, or a $C_3$ to $C_{18}$ phosphite. Generally, each $R^{b7}$ of the phosphite complexes independently can be an organyl group; or alternatively, a hydrocarbyl group. In an embodiment, each $R^{b7}$ organyl group of the phosphite complexes independently can be a $C_1$ to $C_{15}$, a $C_1$ to $C_{10}$, or a $C_1$ to $C_6$ organyl group. In an embodiment, each $R^{b7}$ hydrocarbyl group of the phosphite complexes independently can be a $C_1$ to $C_{15}$, a $C_1$ to $C_{10}$, or a $C_1$ to $C_6$ hydrocarbyl group. In some phosphite complex embodiments all of the $R^{b7}$ groups can be the same; alternatively, two of the $R^{b7}$ groups can be the same and the third different; or alternatively, all three of the $R^{b7}$ groups of can be different. In some phosphite complex embodiments, two $R^{b7}$ groups can be linked to form a ring or ring system (including bicyclic, tricyclic ring systems) containing the phosphite phosphorous atom; in this instance the two linked $R^{b6}$ groups can be designated $R^{j8}$.

In an embodiment, a hydrogen-boron bond containing compound-ether complex can be represented by the formula $[(R^{b8})_2O]BH_3$. In an embodiment, a hydrogen-boron bond containing compound-ether complex can be represented by the formula $[(R^{b8})_2O]BH_2R^{b4}$ or $[(R^{b8})_2O]BH(R^{b4})_2$; alternatively, $[(R^{b8})_2O]BH_2R^{b4}$; or alternatively, $[(R^{b8})_2O]BH(R^{b4})_2$. In an embodiment, a borane-ether complex can be represented by the formula $[(R^{b8})_2O]HB(R^{b4})X$. Generally, in the formulas $[(R^{b8})_2O]BH_2R^{b4}$, $[(R^{b8})_2O]BH(R^{b4})_2$, and/or $[(R^{b8})_2O]HB(R^{b4})X$, $R^{b4}$ can be any group described herein for the hydrogen-boron bond containing compound represented by the formulas $H_2BR^{b4}$ and/or $HB(R^{b4})_2$. Further, $H_2BR^{b4}$, $HB(R^{b4})_2$, or $[(R^{b8})_2O]HB(R^{b4})X$ portion of the borane-ether complex can be any compound having the formula $H_2BR^{b4}$, $HB(R^{b4})_2$, or $[(R^{b81})_2O]HB(R^{b4})X$ described and/or provided herein. In an embodiment, a hydroborohalide-ether complex can be represented by the formula $[(R^{b8})_2O]BH_2X$ or $[(R^{b8})_2O]BHX_2$; alternatively, $[(R^{b8})_2O]BH_2X$; alternatively, $[(R^{b8})_2O]BHX_2$; or alternatively, $[(R^{b8})_2O]HB(R^{b4})X$. In the formulas $[(R^{b8})_2O]BH_2X$, $[(R^{b8})_2O]BHX_2$, or $[(R^{b8})_2O]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the ether of the ether complexes can be a $C_2$ to $C_{30}$, a $C_2$ to $C_{20}$, or a $C_2$ to $C_{12}$ ether. Generally, each $R^{b8}$ of the ether complexes independently can be an organyl group; or alternatively, a hydrocarbyl group. In an embodiment, each $R^{b8}$ organyl group of the ether complexes independently can be a $C_1$ to $C_{15}$, a $C_1$ to $C_{10}$, or a $C_1$ to $C_6$ organyl group. In an embodiment, each $R^{b8}$ hydrocarbyl group of the ether complexes independently can be a $C_1$ to $C_{15}$, a $C_1$ to $C_{10}$, or a $C_1$ to $C_6$ hydrocarbyl group. In some ether complex embodiments, the two $R^{b8}$ groups can be the same; or alternatively, the two $R^{b8}$ groups can be different. In some ether complex embodiments, the two $R^{b8}$ groups can be linked to form a ring or ring system (including bicyclic ring systems) containing the ether oxygen atom; in this instance the two linked $R^{b8}$ groups can be designated $R^{j10}$.

In an embodiment, a hydrogen-boron bond containing compound-sulfide complex can be represented by the formula $[(R^{b9})_2S]BH_3$. In an embodiment, a hydrogen-boron bond containing compound-sulfide complex can be represented by the formula $[(R^{b9})_2S]BH_2R^{b4}$ or $[(R^{b9})_2S]BH(R^{b4})_2$; alternatively, $[(R^{b9})_2S]BH_2R^{b4}$; or alternatively, $[(R^{b9})_2S]BH(R^{b4})_2$. In an embodiment, a borane-amine complex can be represented by the formula $[(R^{b9})_2S]HB(R^{b4})X$. Generally, in the formulas $[(R^{b9})_2S]BH_2R^{b4}$, $[(R^{b9})_2S]BH(R^{b4})_2$, or $[(R^{b9})_2S]HB(R^{b4})X$, $R^{b4}$ can be any group described herein for the hydrogen-boron bond containing compound represented by the formulas $H_2BR^{b4}$ and/or $HB(R^{b4})_2$. Further, the $H_2BR^{b4}$, $HB(R^{b4})_2$, $HB(R^{b4})X$ portion of the borane-sulfide complex can be any compound having the formula $H_2BR^{b4}$, $HB(R^{b4})_2$, $HB(R^{b4})X$ described and/or provided herein. In an embodiment, a hydroborohalide-sulfide complex can be represented by the formula $[(R^{b9})_2S]BH_2X$ or $[(R^{b9})_2S]BHX_2$; alternatively, $[(R^{b9})_2S]BH_2X$; alternatively, $[(R^{b9})_2S]BHX_2$; or alternatively, $[(R^{b9})_2S]HB(R^{b4})X$. In the formulas $[(R^{b9})_2S]BH_2X$, $[(R^{b9})_2]BHX_2$, or $[(R^{b9})_2S]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the sulfide of the sulfide complexes can be a $C_2$ to $C_{30}$, a $C_2$ to $C_{20}$, or a $C_2$ to $C_{12}$ sulfide. Generally, each $R^{b9}$ of the sulfide complexes independently can be an organyl group; or alternatively, a hydrocarbyl group. In an embodiment, each $R^{b9}$ organyl group of the sulfide complexes independently can be a $C_1$ to $C_{15}$, a $C_1$ to $C_{10}$, or a $C_1$ to $C_6$ organyl group. In an embodiment, each $R^{b9}$ hydrocarbyl group of the sulfide complexes independently can be a $C_1$ to $C_{15}$, a $C_1$ to $C_{10}$, or a $C_1$ to $C_6$ hydrocarbyl group. In some sulfide complex embodiments, the two $R^{b9}$ groups can be the same; or alternatively, the two $R^{b9}$ groups can be different. In some sulfide complex embodiments, the two $R^{b9}$ groups can be linked to form a ring or ring system (including bicyclic ring systems) containing the sulfide sulfur atom; in this instance the two linked $R^{b9}$ groups can be designated $R^{11}$.

In an embodiment, the hydrogen borinic acid ester can be represented by the formula $H_2BOR^{b10}$. In an embodiment, hydrogen borinic acid ester can be a $C_1$ to $C_{15}$, a $C_1$ to $C_{10}$, or a $C_1$ to $C_6$ hydrogen borinic acid ester. In an embodiment, the hydrogen boronic acid ester can be represented by the formula $HB(OR^{b11})_2$. In an embodiment, the hydrogen boronic acid ester can be a $C_2$ to $C_{30}$, a $C_2$ to $C_{20}$, or a $C_1$ to $C_{12}$ hydrogen boronic acid ester. Generally, the $R^{b10}$ of the hydrogen borinic acid ester or each $R^{b11}$ of the hydrogen boronic acid ester independently can be an organyl group; or alternatively, a hydrocarbyl group. In an embodiment, the $R^{b10}$ organyl group of the hydrogen borinic acid ester or each $R^{b11}$ organyl group of the hydrogen boronic acid ester independently can be a $C_1$ to $C_{15}$, a $C_1$ to $C_{10}$, or a $C_1$ to $C_6$ organyl group. In an embodiment, the $R^{b10}$ hydrocarbyl group of the hydrogen borinic acid ester or each $R^{b11}$ hydrocarbyl group of the hydrogen boronic acid ester independently can be a $C_1$ to $C_{15}$, a $C_1$ to $C_{10}$, or a $C_1$ to $C_6$ hydrocarbyl group. In some embodiments, the $R^{b11}$ groups of $HB(OR^{b11})_2$ can be the same; or alternatively, the $R^{b11}$ groups of $HB(OR^{b11})_2$ can be different. In some embodiments, the two $R^{b11}$ groups of $HB(OR^{b11})_2$ can be joined to form a ring or ring system containing the two oxygen atoms and the boron atom of the hydrogen boronic acid ester; in this instance the two linked $R^{b11}$ groups can be designated $R^{j12}$. In some embodiments, any hydrogen borinic acid ester described herein can be complexed to any neutral ligand described herein to form a hydrogen borinic acid ester-neutral ligand complex.

In an embodiment, the hydrogen borinic thio acid ester can be represented by the formula $H_2BSR^{b12}$. In an embodiment, the hydrogen borinic thio acid ester can be a $C_1$ to $C_{15}$, a $C_1$ to $C_{10}$, or a $C_1$ to $C_6$ hydrogen borinic acid ester. In an embodiment, the hydrogen boronic thio acid ester can be represented by the formula $HB(SR^{b13})_2$. In an embodiment, the hydrogen boronic thio acid ester can be a $C_2$ to $C_{30}$, a $C_2$ to $C_{20}$, or a $C_1$ to $C_{12}$ hydrogen boronic thio acid ester. Generally, the $R^{b12}$ of the hydrogen borinic thio acid ester or each $R^{b13}$ of the hydrogen boronic thio acid ester independently can be an organyl group; or alternatively, a hydrocarbyl group. In an embodiment, the $R^{b12}$ organyl group of the hydrogen borinic thio acid ester or each $R^{b13}$ organyl group of the hydrogen boronic thio acid ester independently can be a $C_1$ to $C_{15}$, a $C_1$ to $C_{10}$, or a $C_1$ to $C_6$ organyl group. In an embodiment, the $R^{b12}$ hydrocarbyl group of the hydrogen borinic thio acid ester or each $R^{b13}$ hydrocarbyl group of the hydrogen boronic thio acid ester independently can be a $C_1$ to $C_{15}$, a $C_1$ to $C_{10}$, or a $C_1$ to $C_6$ hydrocarbyl group. In some embodiments, the $R^{b13}$ groups of $HB(OR^{b13})_2$ can be the same; or alternatively, the $R^{b13}$ groups of $HB(OR^{b13})_2$ can be different. In some embodiments, the two $R^{b13}$ groups of $HB(OR^{b13})_2$ can be joined to form a ring or ring system containing the two sulfur atoms and the boron atom of the hydrogen boronic thio acid ester; in this instance the two linked $R^{b13}$ groups can be designated $R^{j13}$. In some embodiments, any hydrogen borinic thio acid ester described herein can be complexed to any neutral ligand described herein to form a hydrogen borinic thio acid ester-neutral ligand complex.

In an embodiment, the hydrogen monoaminoborane can be represented by the formula $H_2BNHR^{b14}$ or $H_2BN(R^{b14})_2$; alternatively, $H_2BNHR^{b14}$; or alternatively, $H_2BN(R^{b14})_2$. In an embodiment, the hydrogen monoaminoborane having the formula $H_2BNHR^{b14}$ can be a $C_1$ to $C_{15}$, a $C_1$ to $C_{10}$, or a $C_1$ to $C_6$ hydrogen monoaminoborane. In an embodiment, the hydrogen monoaminoborane having the formula $H_2BN(R^{b14})_2$ can be a $C_2$ to $C_{30}$, a $C_2$ to $C_{20}$, or a $C_2$ to $C_{12}$ hydrogen monoaminoborane. In an embodiment, the hydrogen diaminoborane can be represented by the formula $HB(NHR^{b15})_2$ or $HB(N(R^{b15})_2)_2$; alternatively, $HB(NHR^{b15})_2$; or alternatively, $HB(N(R^{b15})_2)_2$. In an embodiment, the hydrogen diaminoborane having the formula $HB(NHR^{b15})_2$ can be a $C_2$ to $C_{30}$, a $C_2$ to $C_{20}$, or a $C_2$ to $C_{12}$ hydrogen diaminoborane. In an embodiment, the hydrogen diaminoborane having the formula $HB(N(R^{b15})_2)_2$ can be a $C_4$ to $C_{60}$, a $C_4$ to $C_{40}$, or a $C_4$ to $C_{24}$ hydrogen diaminoborane. Generally, each $R^{b14}$ of the hydrogen monoaminoborane or each $R^{b15}$ of the hydrogen diaminoborane independently can be an organyl group; or alternatively, a hydrocarbyl group. In an embodiment, each $R^{b14}$ of the hydrogen monoaminoborane or each $R^{b15}$ of the hydrogen diaminoborane independently can be a $C_1$ to $C_{15}$, a $C_1$ to $C_{10}$, or a $C_1$ to $C_6$ organyl group. In an embodiment, each $R^{b14}$ of the hydrogen monoaminoborane or each $R^{b15}$ of the hydrogen diaminoborane independently can be a $C_1$ to $C_{15}$, a $C_1$ to $C_{10}$, or a $C_1$ to $C_6$ hydrocarbyl group. In an embodiment, the two $R^{b14}$ groups of the hydrogen monoaminoborane having the formula $H_2BN(R^{b14})_2$ can be the same; or alternatively, two $R^{b14}$ groups of the hydrogen monoaminoborane having the formula $H_2BN(R^{b14})_2$ can be different. In some embodiments, the two $R^{b14}$ groups of the hydrogen monoaminoborane having the formula $H_2BN(R^{b14})_2$ can be joined to form a ring or ring system containing the nitrogen atoms of the amino group; in this instance the two linked $R^{b14}$ groups can be designated $R^{j14}$. In an embodiment, the two $R^{b15}$ groups of the hydrogen monoaminoborane having the formula $HB(N(R^{b15})_2)_2$ can be the same; or alternatively, two $R^{b15}$ groups of the hydrogen monoaminoborane having the formula $HB(N(R^{b15})_2)_2$ can be different. In some embodiments, the $R^{b15}$ groups connected to the same nitrogen atom in a hydrogen diamino borane having the formula $HB(N(R^{b15})_2)_2$ can be joined to form a ring or ring system containing the nitrogen atom of the amino group; in this instance the two linked $R^{b15}$ groups can be designated $R^{j14}$. In other embodiments, one $R^{b15}$ group from each of the amino group of the hydrogen diamino borane having the formula $HB(NHR^{b5})_2$ or $HB(N(R^{b15})_2)_2$ can be joined to form ring or ring system containing the two nitrogen atoms and the boron atom of the hydrogen diaminoborane; in this instance the two linked $R^{b15}$ groups can be designated $R^{b15}$.

In an embodiment, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be a $C_1$ to $C_{15}$ alkyl group, a $C_4$ to $C_{15}$ cycloalkyl group, a $C_4$ to $C_{15}$ substituted cycloalkyl group, a $C_6$ to $C_{15}$ aryl group, or a $C_7$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_7$ to $C_{15}$ substituted aryl group; alternatively, a $C_1$ to $C_{15}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_7$ to $C_{15}$ substituted aryl group. In other embodiments, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein and each $R^{b15}$ of a hydrogen diaminoborane described herein, independently can be $C_1$ to $C_{10}$ alkyl group, a $C_4$ to $C_{10}$ cycloalkyl group, a $C_4$ to $C_{10}$ substituted cycloalkyl group, a $C_6$ to $C_{10}$ aryl group, or a $C_7$ to $C_{10}$ substituted aryl group; alternatively, a $C_4$ to $C_{10}$ cycloalkyl group or a $C_4$ to $C_{10}$ substituted cycloalkyl group; alternatively, a $C_6$ to $C_{10}$ aryl group or a $C_7$ to $C_{10}$ substituted aryl group; alternatively, a $C_1$ to $C_{10}$ alkyl group; alternatively, a $C_4$ to $C_{10}$ cycloalkyl group; alternatively, a $C_4$ to $C_{10}$ substituted cycloalkyl group; alternatively, a $C_6$ to $C_{10}$ aryl group; alternatively, a $C_7$ to $C_{10}$ substituted aryl group; or alternatively, a $C_1$ to $C_6$ alkyl group. In the substituted cycloalkyl group and the substituted aryl group embodiments, the substituent(s) can be alkyl groups. Substituents groups (general and specific including alkyl group substituents) are independently disclosed herein and can be utilized without limitation to further describe substituted cycloalkyl groups and/or the substituted aryl groups which can be utilized as a $R^{b1}$ of a hydrogen-boron bond containing compound described herein, a $R^{b4}$ of a hydrogen-boron bond containing compound having the formula $H_2BR^{b4}$ or $HB(R^{b4})_2$ (and any neutral ligand complex thereof) described herein, a $R^{b5}$ Of a borane-amine complex described herein, a $R^{b6}$ Of a borane-phosphine complex described herein, a $R^{b7}$ of a borane-phosphite complex described herein, a $R^{b8}$ of a borane-ether complex described herein, a $R^{b9}$ of a borane-sulfide complex described herein, a $R^{b10}$ a hydrogen borinic acid ester described herein, a $R^{b11}$ of a hydrogen boronic acid ester described herein, a $R^{b12}$ of a hydrogen borinic thio acid ester described herein, a $R^{b13}$ of a hydrogen boronic thio acid ester described herein, each $R^{b14}$ a hydrogen monoaminoborane described herein, and a $R^{b15}$ of a hydrogen diaminoborane described herein.

In an embodiment, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be a methyl group, an ethyl group, a propyl group, a butyl group, a pentyl group, or a hexyl group; or alternatively, a methyl group; alternatively, an ethyl group, alternatively, a propyl group; alternatively, a butyl group; alternatively, a pentyl group; or alternatively, a hexyl group. In other embodiments, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be a methyl group, an ethyl group, a prop-1-yl group, a but-1-yl group, an but-2-yl group, a 2-methyprop-2-yl group, a pent-1-yl group, a 2-methylbut-1-yl group, a 3-methylbut-2-yl group, a neopentyl group, or a 2,3-dimethylbutyl group; alternatively, a prop-1-yl group; alternatively, a but-1-yl group; alternatively, an but-2-yl group; alternatively, a 2-methyprop-2-yl group; alternatively, a pent-1-yl group; alternatively, a 2-methylbut-1-yl group; alternatively, a 3-methylbut-2-yl group; alternatively, a neopentyl group; or alternatively, a 2,3-dimethylbutyl group.

In an embodiment, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be a cyclobutyl group, a cyclopentyl group, a 2-substituted cyclopentyl group, a cyclohexyl group, a 2-substituted cyclohexyl group, a cycloheptyl group, a norborn-2-yl group, a cyclooctyl group, a bicyclo(3.3.0)octan-1-yl group, an adamant-1-yl group, an adamant-2-yl group, or a 2,6,6-trimethylbicyclo (3.1.1)heptan-3-yl group; alternatively, a cyclopentyl group, a 2-substituted cyclopentyl group, a cyclohexyl group, or a 2-substituted cyclohexyl group; alternatively, a cyclopentyl group; alternatively, a 2-substituted cyclopentyl group; alternatively, a cyclohexyl group; or alternatively, a 2-substituted cyclohexyl group. In some embodiments, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ Of a borane-phosphine complex described herein, each $R^{b7}$ Of a borane-phosphite complex described herein, each $R^{b8}$ Of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be, a cyclobutyl group, a cyclopentyl group, a 2-methylcyclopentyl group, a cyclohexyl group, a 2-methylcyclohexyl group, a cycloheptyl group, a norborn-2-yl group, a cyclooctyl group, a bicyclo(3.3.0)octan-1-yl group, an adamant-1-yl group, an adamant-2-yl group, or a 2,6,6-trimethylbicyclo(3.1.1)heptan-3-yl group; alternatively, a cyclopentyl group, a 2-methylcyclopentyl group, a cyclohexyl group, or a 2-methylcyclohexyl group; alternatively, a cyclobutyl group; alternatively, a cyclopentyl group; alternatively, a 2-methylcyclopentyl group; alternatively, a cyclohexyl group; alternatively, a 2-methylcyclohexyl group; alternatively, a cycloheptyl group; alternatively, a norborn-2-yl group; alternatively, a cyclooctyl group; alternatively, a bicyclo(3.3.0)octan-1-yl group; alternatively, an adamant-1-yl group; alternatively, an adamant-2-yl group; or alternatively, a 2,6,6-trimethylbicyclo(3.1.1) heptan-3-yl group.

In an embodiment, each $R^{b1}$ of a hydrogen-boron bond containing compound described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, and each $R^{b15}$ of a hydrogen diaminoborane described herein, independently can be a phenyl group or a substituted phenyl group; alternatively, a phenyl group or a methylphenyl group; alternatively, a phenyl group, a 2-methylphenyl group, or a 4-methylphenyl group; alternatively, a phenyl group; alternatively, a substituted phenyl group; alternatively, a methylphenyl group; alternatively, a 2-methylphenyl group; or alternatively, a 4-methylphenyl group.

In an embodiment, each $R^{b1}$ of a hydrogen-boron bond containing compound described herein independently can be an alkoxy group, a cycloalkoxy group, or an aroxy group; alternatively, an alkoxy group; alternatively, an cycloalkoxy group; or alternatively, an aroxy group. In some embodiments, each $R^{b1}$ of a hydrogen-boron bond containing compound described herein independently can be an $C_1$ to $C_{15}$ alkoxy group, a $C_4$ to $C_{15}$ cycloalkoxy group, a $C_4$ to $C_{15}$ substituted cycloalkoxy group, a $C_6$ to $C_{15}$ aroxy group, or a $C_7$ to $C_{15}$ substituted aroxy group; alternatively, a $C_4$ to $C_{15}$ cycloalkoxy group or a $C_4$ to $C_{15}$ substituted cycloalkoxy group; alternatively, a $C_6$ to $C_{15}$ aroxy group or a $C_7$ to $C_{15}$ substituted aroxy group; alternatively, a $C_1$ to $C_{15}$ alkoxy group; alternatively, a $C_4$ to $C_{15}$ cycloalkoxy group; alternatively, a $C_4$ to $C_{15}$ substituted cycloalkoxy group; alternatively, a $C_6$ to $C_{15}$ aroxy group; or alternatively, a $C_7$ to $C_{15}$ substituted aroxyl group. In an embodiment, each $R^{b1}$ of a hydrogen-boron bond containing compound described herein independently can be $C_1$ to $C_{10}$ alkoxy group, a $C_4$ to $C_{10}$ cycloalkoxy group, a $C_4$ to $C_{10}$ substituted cycloalkoxy group, a $C_6$ to $C_{10}$ aroxy group, or a $C_7$ to $C_{10}$ substituted aroxy group; alternatively, a $C_4$ to $C_{10}$ cycloalkoxy group or a $C_4$ to $C_{10}$ substituted cycloalkoxy group; alternatively, a $C_6$ to $C_{10}$ aroxy group or a $C_7$ to $C_{10}$ substituted aroxy group; alternatively, a $C_1$ to $C_{10}$ alkoxy group; alternatively, a $C_4$ to $C_{10}$ cycloalkoxy group; alternatively, a $C_4$ to $C_{10}$ substituted cycloalkoxy group; alternatively, a $C_6$ to $C_{10}$ aroxy group; alternatively, a $C_7$ to $C_{10}$ substituted aroxy group; or alternatively, a $C_1$ to $C_6$ alkoxy group. In the substituted cycloalkoxy group and the substituted aroxyl group embodiments, the substituent(s) can be alkyl groups. Substituents groups (general and specific including alkyl group substituents) are independently disclosed herein and can be utilized without limitation to further describe substituted cycloalkoxy groups and/or the substituted aroxy groups which can be utilized as an $R^{b1}$ of a hydrogen-boron bond containing compound described herein.

In an embodiment, each $R^{b1}$ of a hydrogen-boron bond containing compound described herein independently can be a methoxy group, an ethoxy group, a propoxy group, a butoxy group, or a pentoxy group; alternatively, a propoxy group; alternatively, a butoxy group; or alternatively, a pentoxy group. In an embodiment, each $R^{b1}$ of a hydrogen-boron bond containing compound described herein independently can be a methoxy group, an ethoxy group, an n-propoxy group, an isopropoxy group, an n-butoxy group, an isobutoxy group, a tert-butoxy group, an n-pentoxy group, or a neo-pentoxy group; alternatively, a methoxy group; alternatively, an ethoxy group; alternatively, an n-propoxy group; alternatively, an isopropoxy group; alternatively, an n-butoxy group; alternatively, an isobutoxy group; alternatively, a tert-butoxy group; alternatively, an n-pentoxy group; or alternatively, a neo-pentoxy group.

In an embodiment, each $R^{b1}$ of a hydrogen-boron bond containing compound described herein independently can be a cyclobutoxy group, a cyclopentoxy group, a substituted cyclopentoxy group, a cyclohexoxy group, a substituted cyclohexoxy group, a cycloheptoxy group, or a cyclooctoxy group; alternatively, a cyclopentoxy group, a substituted cyclopentoxy group, a cyclohexoxy group, or a substituted cyclohexoxy group; alternatively, a substituted cyclopentoxy group; or alternatively, a substituted cyclohexoxy group. In some embodiments, each $R^{b1}$ of a hydrogen-boron bond containing compound described herein independently can be a cyclobutoxy group, a cyclopentoxy group, a cyclohexoxy group, a cycloheptoxy group, or a cyclooctoxy group; alternatively, a cyclopentoxy group, or a cyclohexoxy group; alternatively, a cyclobutoxy group; alternatively, a cyclopentoxy group; alternatively, a cyclohexoxy group; alternatively, a cycloheptoxy group; or alternatively, cyclooctoxy group. In an embodiment, each $R^{b1}$ of a hydrogen-boron bond containing compound described herein independently can be a phenoxy group or a substituted phenoxy group; alternatively, a phenoxy group or a methylphenoxy group; alternatively, a phenoxy group, a 2-methylphenoxy group, or a 4-methylphenoxy group; alternatively, a phenoxy group; alternatively, a substituted phenoxy group; alternatively, a methylphenoxy group; alternatively, a 2-methylphenoxy group; or alternatively, a 4-methylphenoxy group As described herein two $R^{b1}$ groups can be joined as a $R^{j1}$ group (to form a ring or ring system containing the boron atom of the hydrogen-boron bond containing salt), two $R^{b4}$ groups can be joined as a $R^{j3}$ group (to form a ring or ring system containing the boron atom of a hydrogen-boron bond containing compound), two $R^{b5}$ groups can be joined as a $R^{j4}$ group (to form a cyclic amine neutral ligand), two $R^{b6}$ groups can be joined as a $R^{j6}$ group (to form a cyclic phosphine neutral ligand), two $R^{b8}$ groups can be joined as a $R^{j10}$ group (to form a cyclic ether neutral ligand), two $R^{b9}$ groups can be joined as a $R^{j11}$ group (to form a cyclic sulfide neutral ligand), two $R^{b14}$ groups can be joined as a $R^{j14}$ group (to form a cyclic amino group), or two $R^{b15}$ groups can be joined as a $R^{j14}$ (to form a cyclic amino group). In an embodiment, the $R^{j1}$ group, the $R^{j3}$ group, the $R^{j4}$ group, the $R^{j6}$ group, the $R^{j10}$ group, the $R^{j14}$ group, the $R^{j14}$ group, or the $R^{j14}$ group can be a $C_4$ to $C_{20}$, a $C_4$ to $C_{15}$, or a $C_4$ to $C_{10}$ hydrocarbylene group. In other embodiments, the $R^{j1}$ group, the $R^{j3}$ group, the $R^{j4}$ group, the $R^{j6}$ group, the $R^{j10}$ group, the $R^{j11}$ group, the $R^{j14}$ group, or the $R^{j14}$ group can be represented -$(CR^{d1}R^{d2})_5$—, —$CR^{d1}R^{d2}(CH_2)_3CR^{d1}R^{d2}$—, or —$CR^{d3}$=$CR^{d4}CR^{d5}$=$CR^{d6}$—; alternatively, —$(CR^{d1}R^{d2})_4$—; alternatively, $CR^{d1}R^{d2}(CH_2)_2CR^{d1}R^{d2}$—, alternatively, —$(CR^{d1}R^{d2})_5$—; alternatively, —$CR^{d1}R^{d2}(CH_2)_3CR^{d1}R^{d2}$—; or alternatively, —$CR^{d3}$=$CR^{d4}CR^{d5}$=$CR^{d6}$—. In these $R^{j1}$ groups, $R^{j3}$ groups, $R^{j4}$ groups, $R^{j6}$ groups, $R^{j10}$ groups, $R^{j11}$ groups, $R^{j14}$ groups, and/or $R^{j14}$ groups, each $R^{d1}$, $R^{d2}$, $R^{d3}$, $R^{d4}$, $R^{d5}$, or $R^{d6}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{d1}$, $R^{d2}$, $R^{d3}$, $R^{d4}$, $R^{d5}$, or $R^{d6}$ of the $R^{j1}$ group, $R^{j3}$ group, $R^{j4}$ group, $R^{j6}$ group, $R^{j10}$ group, $R^{j11}$ group, $R^{j14}$ group, and/or $R^{j14}$ group. In other embodiments, the $R^{j1}$ group, the $R^{j3}$ group, the $R^{j4}$ group, the $R^{j6}$ group, the $R^{j10}$ group, the $R^{j11}$ group, the $R^{j14}$ group, or the $R^{j14}$ group can be represented by —$(CH_2)_4$—, —$(CH_2)_5$—, —CH=CHCH=CH—; alternatively, —$(CH_2)_4$; alternatively, —$(CH_2)_5$—; or alternatively, or —CH=CHCH=CH—. In some embodiments, the two $R^{b1}$ groups joined as a $R^{j1}$ group (to form a ring or ring system containing the boron atom of the hydrogen-boron bond containing salt), the two $R^{b4}$ groups joined as a $R^{j3}$ group (to form a ring or ring system containing the boron atom of a hydrogen-boron bond containing compound) can be a cycloocta-1,5-diyl group.

As described herein two $R^{b1}$ groups can be joined as a $R^{j1}$ group (to form a cyclic boronic acid ester of the containing the boron atom and two oxygen atoms of the boronic acid ester of a hydrogen-boron bond containing salt), two $R^{b7}$ groups can be joined as a $R^{j8}$ group (to form a cyclic phosphite neutral ligand), two $R^{b11}$ groups can be joined as a $R^{j12}$ group (to form a cyclic boronic acid ester of the containing the boron atom and two oxygen atoms of the boronic acid ester), two $R^{b13}$ groups can be joined as a $R^{j13}$ group (to form a cyclic boronic thio acid ester of the containing the boron atom and two sulfur atoms of the boronic thio acid ester), or two $R^{b15}$ groups can be joined as $R^{j15}$ group (to form a cyclic hydrogen diamino borane containing the boron atom and two nitrogen atoms of the hydrogen diamino borane). In some embodiments, the $R^{j1}$ group, the $R^{j8}$ group, the $R^{j12}$ group, the $R^{j13}$ group, or the $R^{j15}$ group can be a $C_2$ to $C_{20}$, a $C_2$ to $C_{15}$, or a $C_2$ to $C_{10}$ hydrocarbylene group. In other embodiments, the $R^{j1}$ group, the $R^{j8}$ group, the $R^{j12}$ group, the $R^{j13}$ group, or the $R^{j15}$ group can be represented by —$(CR^{e1}R^{32})_2$—, —$(CR^{e1}R^{e2})_3$—, —$CR^{e1}R^{e2}(CH_2)CR^{e1}R^{e2}$—, or —$CR^{e3}$=$CR^{e4}$—; alternatively, —$(CR^{e1}R^{32})_2$—; alternatively, —$(CR^{e1}R^{e2})_3$—; alternatively, —$CR^{e1}R^{e2}(CH_2)CR^{e1}R^{e2}$—; or alternatively, —$CR^{e3}$=$CR^{e4}$—. In these $R^{j1}$ groups, $R^{j8}$ groups, $R^{j12}$ groups, $R^{j13}$ groups, and/or $R^{j15}$ groups, each $R^{e1}R^{e2}$, $R^{e3}$, or $R^{e4}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{e1}$, $R^{e2}$, $R^{e3}$, or $R^{e4}$ of the $R^{j1}$ group, $R^{j8}$ group, $R^{j12}$ group, $R^{j13}$ group, and/or $R^{j15}$ group. In other embodiments, the $R^{j1}$ group, the $R^{j8}$ group, the $R^{j12}$ group, the $R^{j13}$ group, or the $R^{j15}$ group can be represented by —$(CH_2)_2$—, —$(CH_2)_3$—, —CH=CH—; alternatively, —$(CH_2)_2$—; alternatively, —$(CH_2)_3$—; or alternatively, or —CH=CH—.

As described herein three $R^{b1}$ groups can be joined as an $R^{j2}$ group (to form a ring or ring system containing the boron atom), three $R^{b5}$ groups can be joined as an $R^{j5}$ group (to form a cyclic amine neutral ligand), or three $R^{b6}$ groups can be joined as an $R^{j7}$ group (to form a cyclic phosphine neutral ligand). In an embodiment, the $R^{j2}$ group, the $R^{j5}$ group, the $R^{j7}$ group, or the $R^{j9}$ group can be a $C_8$ to $C_{20}$ hydrocarbon group, or alternatively, a $C_8$ to $C_{15}$ hydrocarbon group. In other embodiments, the $R^{j2}$ group, the $R^{j5}$ group, or the $R^{j7}$ group can be represented by —$CR^{g1}((CR^{g2}R^{g3})_2CR^{g4g5}-)_2$, —$CR^{g1}((CH_2)_2CR^{g4g5}—)_2$—$CR^{g1}(CR^{g2}R^{g3})_2CR^{g4g5}—)(CR^{g2}R^{g3})_3CR^{g4g5}—)$, —$CR^{g1}(CH_2)_2CR^{g4g5}—)(CH_2)_3CR^{g4g5}—)$, or —$CR^{g1}((CH)_3CR^{g4g5}-)_2$; alternatively, —$CR^{g1}((CR^{g2}R^{g3})_2CR^{g4g5}-)_2$; alternatively, —$CR^{g1}((CH_2)_2CR^{g4g5}-)_2$; alternatively, —$CR^{g1}(CR^{g2}R^{g3})_2CR^{g4g5}—)(CR^{g2}R^{g3})_3CR^{g4g5}—)$; alternatively, —$CR^{g1}(CH_2)_2CR^{g4g5}—)(CH_2)_3CR^{g4g5}—)$; or alternatively, —$CR^{g1}((CH)_3CR^{g4g5}-)_2$. In other embodiments, the $R^{j5}$ group can be represented by =$CR^{g6}$=$CR^{g7}CR^{g8}$=$CR^{g9}$—. In these $R^{j2}$ groups, $R^{j5}$ groups, and/or $R^{j7}$ groups, each $R^{g1}$, $R^{g2}$, $R^{g3}$, $R^{g4}$, $R^{g5}$, $R^{g6}$, $R^{g7}$, $R^{g8}$, $R^{g9}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{g1}$, $R^{g2}$, $R^{g3}$, $R^{g4}$, $R^{g5}$, $R^{g6}$, $R^{g7}$, $R^{g8}$, $R^{g9}$ of the $R^{j2}$ group, $R^{j5}$ group, and/or $R^{j7}$ group. In other embodiments, the $R^{j2}$ group, the $R^{j5}$ group, or the $R^{j7}$ group can be represented by —CH$((CH_2)_2CH—)_2$, —CH$(CH_2)_2CH—)(CH_2)_3CH—)$, or —CH$((CH)_3CH—)_2$; alternatively, —CH$((CH_2)_2CH—)_2$; alternatively, —CH$(CH_2)_2$CH—)$(CH_2)_3$CH—); or alternatively, —CH$((CH)_3CH—)_2$. In other embodiments, the $R^{j5}$ group can be represented by =CH=CHCN=CH—.

In an embodiment, the borohydride compound portion of the borohydride compound salt, which can be utilized as the hydrogen-boron bond containing compound in the processes described herein, can be borohydride (i.e., $BH_4^-$), cyanoborohydride (i.e., $(CN)BH_3^-$), trimethylboron hydride, triethylboron hydride, tripropylboron hydride, tri-n-butylboron hydride, tricyclopentylboron hydride, tri(2-methylcyclopentyl)boron hydride, tricyclohexylboron hydride, tri(2-methylcyclohexyl)boron hydride, triphenylboron hydride, 9-borabicyclo[3.3.1]nonane hydride (9-BBN hydride), methyl 9-borabicyclo[3.3.1]nonane hydride, ethyl 9-borabicyclo[3.3.1]nonane hydride, propyl 9-borabicyclo[3.3.1]-nonane hydride, isopropyl 9-borabicyclo[3.3.1]nonane hydride, n-butyl 9-borabicyclo[3.3.1]nonane hydride, tert-butyl 9-borabicyclo[3.3.1]nonane hydride, 2,3-but-2-yl 9-borabicyclo[3.3.1]nonane hydride, cyclobutyl 9-borabicyclo[3.3.1]nonane hydride, cyclopentyl 9-borabicyclo[3.3.1]nonane hydride, 2-methylclopentyl 9-borabicyclo[3.3.1]nonane hydride, cyclohexyl 9-borabicyclo[3.3.1]nonane hydride, 2-methylcyclohexyl 9-borabicyclo[3.3.1]nonane hydride, 2-norbornyl 9-borabicyclo[3.3.1]nonane hydride, phenyl 9-borabicyclo[3.3.1]nonane hydride, or benzyl 9-borabicyclo[3.3.1]nonane hydride; alternatively, trimethylboron hydride, triethylboron hydride, tripropylboron hydride, tri-n-butylboron hydride, tricyclopentylboron hydride, tri(2-methylcyclopentyl)boron hydride, tricyclohexylboron hydride, tri(2-methylcyclohexyl)boron hydride, or triphenylboron hydride; or alternatively, 9-borabicyclo[3.3.1]nonane hydride (9-BBN hydride), methyl 9-borabicyclo[3.3.1]nonane hydride, ethyl 9-borabicyclo[3.3.1]nonane hydride, propyl 9-borabicyclo[3.3.1]nonane hydride, isopropyl 9-borabicyclo[3.3.1]nonane hydride, n-butyl 9-borabicyclo[3.3.1]nonane hydride, tert-butyl 9-borabicyclo[3.3.1]nonane hydride, 2,3-but-2-yl 9-borabicyclo[3.3.1]nonane hydride, cyclobutyl 9-borabicyclo[3.3.1]nonane hydride, cyclopentyl 9-borabicyclo[3.3.1]nonane hydride, 2-methylcyclopentyl 9-borabicyclo[3.3.1]nonane hydride, cyclohexyl 9-borabicyclo[3.3.1]nonane hydride, 2-methylcyclohexyl 9-borabicyclo[3.3.1]nonane hydride, 2-norbornyl 9-borabicyclo[3.3.1]nonane hydride, phenyl 9-borabicyclo[3.3.1]nonane hydride, or benzyl 9-borabicyclo[3.3.1]nonane hydride. In some embodiments, the borohydride compound portion of the borohydride compound salt, which can be utilized as the hydrogen-boron bond containing compound in the processes described herein, can be borohydride (i.e., $BH_4^-$); alternatively, cyanoborohydride (i.e., $(CN)BH_3^-$); alternatively, trimethylboron hydride; alternatively, triethylboron hydride; alternatively, tripropylboron hydride; alternatively, tri-n-butylboron hydride; alternatively, tricyclopentylboron hydride; alternatively, tri(2-methylcyclopentyl)boron hydride; alternatively, tricyclohexylboron hydride; alternatively, tri(2-methylcyclohexyl)boron hydride; alternatively, triphenylboron hydride; alternatively, 9-borabicyclo[3.3.1]nonane hydride; alternatively, methyl 9-borabicyclo[3.3.1]nonane hydride; alternatively, ethyl 9-borabicyclo[3.3.1]nonane hydride; alternatively, propyl 9-borabicyclo[3.3.1]nonane hydride; alternatively, isopropyl 9-borabicyclo[3.3.1]nonane hydride; alternatively, n-butyl 9-borabicyclo[3.3.1]nonane hydride; alternatively, tert-butyl 9-borabicyclo[3.3.1]nonane hydride; alternatively, 2,3-but-2-yl 9-borabicyclo[3.3.1]nonane hydride; alternatively, cyclobutyl 9-borabicyclo[3.3.1]nonane hydride; alternatively, cyclopentyl 9-borabicyclo[3.3.1]nonane hydride; alternatively, 2-methylcyclopentyl 9-borabicyclo[3.3.1]nonane hydride; alternatively, cyclohexyl 9-borabicyclo[3.3.1]nonane hydride; alternatively, 2-methylcyclohexyl 9-borabicyclo[3.3.1]nonane hydride; alternatively, 2-norbornyl 9-borabicyclo[3.3.1]nonane hydride; alternatively, phenyl 9-borabicyclo[3.3.1]nonane hydride; or alternatively, benzyl 9-borabicyclo[3.3.1]nonane hydride. Other borohydride compound portions of the borohydride compound salts can be readily envisioned and contemplated from the present disclosure. Additionally, any borohydride compound portion of the borohydride compound salt disclosed herein can be combined with any cation, $A'''$, of the borohydride compound salts described herein to describe hydrogen-boron bond containing compound (e.g., borohydride compound salts) which can be utilized in processes described herein.

In an embodiment, the hydroborohalide, which can be utilized in the processes described herein, or can be the hydroborohalide portion of a hydroborohalide-neutral ligand complex, which can be utilized in the processes described herein, can be chloroborane, bromoborane, dichloroborane, dibromoborane, or bromochloroborane; alternatively, chloroborane, or bromoborane; alternatively, dichloroborane, dibromoborane, or bromochloroborane; alternatively, chloroborane; alternatively, bromoborane; alternatively, dichloroborane; alternatively, dibromoborane; or alternatively, bromochloroborane. Other hydroborohalides can be readily envisioned and contemplated from the present disclosure. Additionally, any hydroborohalide disclosed herein can be combined with any neutral ligand described herein to describe hydroborohalide-neutral ligand complexes which can be utilized in processes described herein.

In an embodiment, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be borane, diborane, methylborane, ethylborane, n-propylborane, isopropylborane, n-butylborane, tert-butylborane, n-pentylborane, 2-methylbut-1-ylborane, n-hexylborane, 2-methylpent-2-ylborane, 2,3-dimethylbut-2-ylborane, cyclopentylborane, 2-methylcyclopentylborane, cyclohexylborane, 2-methylcyclohexylborane, norboran-2-ylborane, 2,6,6-trimethylbicyclo-(3.1.1)heptan-3-ylborane, phenylborane, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, di-2,3-dimethylbut-2-ylborane, dicyclopentylborane, di-2-methylcyclopentylborane, dicyclohexylborane, di-2-methylcyclohexylborane, di-2,6,6-trimethylbicyclo-(3.1.1)heptan-3-ylborane, diphenylborane, tert-butyl(2-methyl-but-2-yl)borane, tert-butyl(cyclopentyl)borane, tert-butyl(2-methylcyclopentyl)borane, tert-butyl(cyclohexyl)borane, tert-butyl(2-methylcyclo-hexyl)borane, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, 2,3-dimethylbut-2-yl(2-methylcyclohexyl)borane, or 9-borabicyclo[3.3.1]nonane; alternatively, methylborane, ethylborane, n-propylborane, isopropylborane, n-butylborane, tert-butylborane, n-pentylborane, 2-methylbut-1-ylborane, n-hexylborane, 2-methylpent-2-ylborane, or 2,3-dimethylbut-2-ylborane, cyclopentylborane, 2-methylcyclopentylborane, cyclohexylborane, 2-methylcyclohexylborane, norboran-2-ylborane, 2,6,6-trimethylbicyclo(3.1.1)heptan-3-ylborane, or phenylborane; alternatively, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, di-2,3-dimethylbut-2-ylborane, dicyclopentylborane, di-2-methylcyclopentylborane, dicyclohexylborane, di-2-methylcyclohexylborane, di-2,6,6-trimethylbicyclo(3.1.1)heptan-3-ylborane, or diphenylborane; or alternatively, tert-butyl(2-methyl-but-2-yl)borane, tert-butyl(cyclopentyl)borane, tert-butyl(2-methylcyclopentyl)borane, tert-butyl(cyclohexyl)borane, tert-butyl(2-methylcyclohexyl)borane, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, 2,3-dimethylbut-2-yl(2-methylcyclohexyl)borane, or 9-borabicyclo[3.3.1]nonane. In some embodiments, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylborane, ethylborane, n-propylborane, isopropylborane, n-butylborane, tert-butylborane, n-pentylborane, 2-methylbut-1-ylborane, n-hexylborane, 2-methylpent-2-ylborane, or 2,3-dimethylbut-2-ylborane; alternatively, cyclopentylborane, 2-methylcyclopentylborane, cyclohexylborane, 2-methylcyclohexylborane, norboran-2-ylborane, 2,6,6-trimethylbicyclo(3.1.1)heptan-3-ylborane, or phenylborane; alternatively, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, or di-2,3-dimethylbut-2-ylborane; alternatively, dicyclopentylborane, di-2-methylcyclopentylborane, dicyclohexylborane, di-2-methylcyclohexylborane, di-2,6,6-trimethylbicyclo(3.1.1) heptan-3-ylborane, or diphenylborane; alternatively, tert-butyl(2-methyl-but-2-yl)borane, tert-butyl(cyclopentyl) borane, tert-butyl(2-methylcyclopentyl)borane, tert-butyl (cyclohexyl)borane, or tert-butyl(2-methylcyclohexyl) borane; alternatively, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, or 2,3-dimethylbut-2-yl(2-methylcyclohexyl)borane; alternatively, borane; alternatively, diborane; alternatively, methylborane, alternatively, ethylborane; alternatively, n-propylborane; alternatively, isopropylborane; alternatively, n-butylborane; alternatively, tert-butylborane; alternatively, n-pentylborane; alternatively, 2-methylbut-1-ylborane; alternatively, n-hexylborane; alternatively, 2-methylpent-2-ylborane; alternatively, 2,3-dimethylbut-2-ylborane; alternatively, cyclopentylborane; alternatively, 2-methylcyclopentylborane; alternatively, cyclohexylborane; alternatively, 2-methylcyclohexylborane; alternatively, norboran-2-ylborane; alternatively, 2,6,6-trimethylbicyclo(3.1.1)heptan-3-ylborane; alternatively, phenylborane; alternatively, dimethylborane; alternatively, diethylborane; alternatively, di-n-propylborane; alternatively, diisopropylborane; alternatively, di-n-butylborane; alternatively, di-tert-butylborane; alternatively, di-n-pentylborane; alternatively, di-2-methylbut-1-ylborane; alternatively, di-n-hexylborane; alternatively, di-2-methylpent-2-ylborane; alternatively, di-2,3-dimethylbut-2-ylborane; alternatively, dicyclopentylborane, di-2-methylcyclopentylborane; alternatively, dicyclohexylborane; alternatively, di-2-methylcyclohexylborane; alternatively, di-2,6,6-trimethylbicyclo(3.1.1)heptan-3-ylborane; alternatively, diphenylborane; alternatively, tert-butyl(2-methyl-but-2-yl)borane; alternatively, tert-butyl(cyclo-pentyl)borane; alternatively, tert-butyl(2-methylcyclopentyl)borane; alternatively, tert-butyl(cyclohexyl)borane; alternatively, tert-butyl(2-methylcyclohexyl)borane; alternatively, 2,3-dimethylbut-2-yl(2-methyl-but-2-yl)borane; alternatively, 2,3-dimethylbut-2-yl(cyclopentyl)borane; alternatively, 2,3-dimethylbut-2-yl(2-methylcyclopentyl)borane; alternatively, 2,3-dimethylbut-2-yl(cyclohexyl)borane; alternatively, 2,3-dimethylbut-2-yl(2-methylcyclohexyl)borane; or alternatively, 9-borabicyclo[3.3.1]nonane. Other hydrocarbylboranes can be readily envisioned and contemplated from the present disclosure. Additionally, any hydrocarbylborane disclosed herein can be combined with any neutral ligand described herein to describe neutral ligand complexes which can be utilized in processes described herein.

In an embodiment, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylchlororborane, ethylchloroborane, n-propylchloroborane, isopropylchloroborane, n-butylchloroborane, tert-butylchloroborane, n-pentylchloroborane, 2-methylbut-1-ylchloroborane, n-hexylchloroborane, 2-methylchloropent-2-ylborane, 2,3-dimethylchlorobut-2-ylborane, cyclopentychlorolborane, cyclohexylchloroborane, 2,6,6-trimethylbicyclo(3.1.1)heptan-3-ylchloroborane, or phenylchloroborane; alternatively, methylchlororborane, ethylchloroborane, n-propyl-chloroboranechloride, isopropylchloroborane, n-butylchlorobo-rane, tert-butylchloroborane, n-pentylchloroborane, 2-methylbut-1-ylchloroborane, n-hexylchloroborane, 2-methylchloropent-2-ylborane, or 2,3-dimethylchlorobut-2-ylborane; alternatively, cyclopentychlorolborane, cyclohexylchloroborane, 2,6,6-trimethylbicyclo(3.1.1)heptan-3-ylchloroborane, or phenylchloroborane. In some embodiments, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylchlororborane; alternatively, ethylchloroborane; alternatively, n-propylchloroborane; alternatively, isopropylchloroborane; alternatively, n-butylchloroborane; alternatively, tert-butylchloroborane; alternatively, n-pentylchloroborane; alternatively, 2-methylbut-1-ylchloroborane; alternatively, n-hexylchloroborane; alternatively, 2-methylchloropent-2-ylborane; alternatively, 2,3-dimethylchlorobut-2-ylborane; alternatively, cyclopentychlorolborane; alternatively, cyclohexylchloroborane; alternatively, 2,6,6-trimethylbicyclo(3.1.1)heptan-3-ylchloroborane; or alternatively, phenylchloroborane. Other alkylhaloborane can be readily envisioned and contemplated from the present disclosure. Additionally, any alkylhaloborane disclosed herein can be combined with any neutral ligand described herein to describe alkylhaloborane-neutral ligand complexes which can be utilized in processes described herein.

In an embodiment, the amine which can be complexed with any hydrogen-boron bond containing compound described herein to form the hydrogen-boron bond containing compound-amine complex which can be utilized in the processes described herein can be ammonia, methylamine, ethylamine, isopropylamine, n-butylamine, tert-butylamine, cyclopentylamine, cyclohexylamine, phenylamine, dimethylamine, diethylamine, diisopropylamine, di-n-butylamine, di-tert-butylamine, dicyclopentylamine, dicyclohexylamine, diphenylamine, pyrrolidine, piperdine, pyrrole, trimethylamine, triethylamine, triisopropylamine, tri-n-butylamine, tri-tert-butylamine, tricyclopentylamine, tricyclohexylamine, triphenylamine, tetramethylamineethylenediamine, pyridine, or any combinations thereof; alternatively, methylamine, ethylamine, isopropylamine, n-butylamine, tert-butylamine, cyclopentylamine, cyclohexylamine, phenylamine, or any combination thereof; alternatively, dimethylamine, diethylamine, diisopropylamine, di-n-butylamine, di-tert-butylamine, dicyclopentylamine, dicyclohexylamine, diphenylamine, pyrrolidine, piperdine, pyrrole, or any combination thereof; alternatively, trimethylamine, triethylamine, triisopropylamine, tri-n-butylamine, tri-tert-butylamine, tricyclopentylamine, tricyclohexylamine, triphenylamine, tetramethylamineethylenediamine, pyridine, or any combinations thereof. In some embodiments, the amine which can be complexed with any hydrogen-boron bond containing compound described herein to form the hydrogen-boron bond containing compound-amine complex which can be utilized in the processes described herein can be methylamine, ethylamine, isopropylamine, n-butylamine, tert-butylamine, cyclopentylamine, cyclohexylamine, or any combinations thereof; alternatively, dimethylamine, diethylamine, diisopropylamine, di-n-butylamine, di-tert-butylamine, dicyclopentylamine, dicyclohexylamine, diphenylamine, pyrrolidine, piperdine, or any combinations thereof; alternatively, trimethylamine, triethylamine, triisopropylamine, tri-n-butylamine, tri-tert-butylamine, tricyclopentylamine, tricyclohexylamine, tetramethylamineethylenediamine, or any combinations thereof; alternatively, ammonia; alternatively; methylamine; alternatively, ethylamine; alternatively, isopropylamine; alternatively, n-butylamine; alternatively, tert-butylamine; alternatively, cyclopentylamine; alternatively, cyclohexylamine; alternatively, phenylamine; alternatively, dimethylamine; alternatively, diethylamine; alternatively, diisopropylamine; alternatively, di-n-butylamine; alternatively, di-tert-butylamine; alternatively, dicyclopentylamine; alternatively, dicyclohexylamine; alternatively, diphenylamine; alternatively, pyrrolidine; alternatively, piperdine; alternatively, pyrrole; alternatively, trimethylamine; alternatively, triethylamine; alternatively, triisopropylamine; alternatively, tri-n-butylamine; alternatively, tri-tert-butylamine; alternatively, tricyclopentylamine; alternatively, tricyclohexylamine; alternatively, triphenylamine; alternatively, tetramethylamineethylenediamine; or alternatively, pyridine.

In an embodiment, the phosphine which can be complexed with any hydrogen-boron bond containing compound described herein to form the hydrogen-boron bond containing compound-phosphine complex which can be utilized in the processes described herein can be phosphine, methylphosphine, ethylphosphine, isopropylphosphine, tert-butylphosphine, phenylphosphine, dimethylphosphine, diethylphosphine, diisopropylphosphine, di-tert-butylphosphine, diphenylphosphine, trimethylphosphine, triethylphosphine, triisopropylphosphine, tri-tert-butylphosphine, triphenylphosphine, or any combination thereof; alternatively, methylphosphine, ethylphosphine, isopropylphosphine, tert-butylphosphine, phenylphosphine, or any combination thereof; alternatively, dimethylphosphine, diethylphosphine, diisopropylphosphine, di-tert-butylphosphine, diphenylphosphine, or any combination thereof; alternatively, trimethylphosphine, triethylphosphine, triisopropylphosphine, tri-tert-butylphosphine, triphenylphosphine, or any combination thereof; alternatively, phosphine; alternatively, methylphosphine; alternatively, ethylphosphine; alternatively, isopropylphosphine; alternatively, tert-butylphosphine; alternatively, phenylphosphine; alternatively, dimethylphosphine; alternatively, diethylphosphine; alternatively, diisopropylphosphine; alternatively, di-tert-butylphosphine; alternatively, diphenylphosphine; alternatively, trimethylphosphine; alternatively, triethylphosphine; alternatively, triisopropylphosphine; alternatively, tri-tert-butylphosphine; or alternatively, triphenylphosphine. In other embodiments, the phosphine which can be complexed with any hydrogen-boron bond containing compound described herein to form the hydrogen-boron bond containing compound-phosphine complex which can be utilized in the processes described herein can be trifluorophosphine. In an embodiment, the phosphite which can be complexed with any hydrogen-boron bond containing compound described herein to form the hydrogen-boron bond containing compound-phosphite complex which can be utilized in the processes described herein can be trimethylphosphite, triethylphosphite, triisopropyl phosphite, or triphenylphosphite; alternatively, trimethylphosphite; alternatively, triethylphosphite; alternatively, triisopropylphosphite; or alternatively, triphenylphosphite.

In an embodiment, the ether which can be complexed with any hydrogen-boron bond containing compound described herein to form the hydrogen-boron bond containing compound-ether complex which can be utilized in the processes described herein can be dimethylether, diethylether, diisopropylether, diphenylether, furan, tetrahydrofuran, pyran, dihydropyran, tetrahydropyran, 1,3-dioxane, 1,4-dioxane, or any combination thereof; alternatively, dimethylether, diethylether, diisopropylether, tetrahydrofuran, tetrahydropyran, or any combination thereof; alternatively, dimethylether; alternatively, diethylether; alternatively, diisopropylether; alternatively, diphenylether; alternatively, furan; alternatively, tetrahydrofuran; alternatively, pyran; alternatively, dihydropyran; alternatively, tetrahydropyran; alternatively, 1,3-dioxane; or alternatively, 1,4-dioxane. In an embodiment, the sulfide which can be complexed with any hydrogen-boron bond containing compound described herein to form the hydrogen-boron bond containing compound-sulfide complex which can be utilized in the processes described herein can be dimethylsulfide, diethylsulfide, diisopropylsulfide, diphenylsulfide, thiophene, thiophane, thiane, or any combination thereof; alternatively, dimethylsulfide, diethylsulfide, diphenylsulfide, thiolane, thiane, or any combination thereof; alternatively, dimethylsulfide; alternatively, diethylsulfide; alternatively, diisopropylsulfide; alternatively, diphenylsulfide; alternatively, thiophene; alternatively, thiophane; or alternatively, thiane.

In an embodiment, the hydrogen borinic acid ester, which can be utilized in the processes described herein, or can be the hydrogen borinic acid ester of a hydrogen borinic acid ester-neutral ligand complex, which can be utilized in the processes described herein, can be methyl borinate, ethyl borinate, n-propyl borinate, isopropyl borinate, n-butyl borinate, tert-butyl borinate, phenyl borinate, or any combination thereof; alternatively, methyl borinate; alternatively, ethyl borinate; alternatively, n-propyl borinate; alternatively, isopropyl borinate; alternatively, n-butyl borinate; alternatively, tert-butyl borinate; or alternatively, phenyl borinate. Other hydrogen borinic acid esters can be readily envisioned and contemplated from the present disclosure. Additionally, any hydrogen borinic acid ester disclosed herein can be combined with any neutral ligand described herein to describe hydrogen borinic acid ester-neutral ligand complex which can be utilized in processes described herein.

In an embodiment, the hydrogen borinic thio acid ester, which can be utilized in the processes described herein, or can be the hydrogen borinic thio acid ester of a hydrogen borinic thio acid ester-neutral ligand complex, which can be utilized in the processes described hereinor methyl thioborinate, ethyl thioborinate, n-propyl thioborinate, isopropyl thioborinate, n-butyl thioborinate, tert-butyl thioborinate, phenyl thioborinate, or any combination thereof; alternatively, methyl thioborinate; alternatively, ethyl thioborinate; alternatively, n-propyl thioborinate; alternatively, isopropyl thioborinate; alternatively, n-butyl thioborinate; alternatively, tert-butyl thioborinate; phenyl thioborinate. Other hydrogen borinic thio acid esters can be readily envisioned and contemplated from the present disclosure. Additionally, any hydrogen borinic thio acid ester disclosed herein can be combined with any neutral ligand described herein to describe hydrogen borinic thio acid ester-neutral ligand complex which can be utilized in processes described herein.

In an embodiment, the hydrogen monoaminoborane, which can be utilized in the processes described herein, or can be the hydrogen monoaminoborane of a hydrogen monoaminoborane-neutral ligand complex, which can be utilized in the processes described herein, can be dimethylaminylborane, diethylaminylborane, di-n-propyaminylborane, diisopropylaminylborane, di-n-butylaminylborane, di-tert-butylaminylborane, dicyclopentylaminylborane, dicyclohexylaminylborane, pyrrolidinylborane, or piperdinylborane; alternatively, dimethylaminylborane; alternatively, diethylaminylborane; alternatively, di-n-propyaminylborane; alternatively, diisopropylaminylborane; alternatively, di-n-butylaminylborane; alternatively, di-tertbutylaminylborane; alternatively, dicyclopentylaminylborane; alternatively, dicyclohexylaminylborane; alternatively, pyrrolidinylborane; or alternatively, piperdinylborane. In some embodiments, the hydrogen monoaminoborane, which can be utilized in the processes described herein, or can be the hydrogen monoaminoborane of a hydrogen monoaminoborane-neutral ligand complex, which can be utilized in the processes described herein, can be methyl(dimethylaminyl) borane, methyl(diethylaminyl)borane, methyl(di-n-propyaminyl)borane, methyl(diisopropylaminyl)borane, methyl(di-n-butylaminyl)borane, methyl(dicyclopentylaminyl) borane, methyl(dicyclohexylaminyl)borane, methyl (pyrrolidinyl)borane, methyl(piperidinyl)borane, tert-butyl (dimethylaminyl)borane, tert-butyl(diethylaminyl)borane, tert-butyl(di-n-propyaminyl)borane, tert-butyl(diisopropylaminyl)borane, tert-butyl(di-n-butylaminyl)borane, tert-butyl(dicyclopentylaminyl)borane, tert-butyl(dicyclohexylaminyl)borane, tert-butyl(pyrrolidinyl)borane, tert-butyl (piperidinyl)borane, 2,3-dimethylbut-2-yl(dimethylaminyl) borane, 2,3-dimethylbut-2-yl(diethylaminyl)borane, 2,3-dimethylbut-2-yl(di-n-propyl-aminyl)borane, 2,3-dimethylbut-2-yl(diisopropylaminyl)borane, 2,3-dimethylbut-2-yl(di-n-butylaminyl)borane, 2,3-dimethylbut-2-yl(dicyclopentylaminyl)borane, 2,3-dimethylbut-2-yl(dicyclohexylaminyl)borane, 2,3-dimethylbut-2-yl(pyrrolidinyl)borane, or 2,3-dimethylbut-2-yl(piperidinyl)borane; alternatively, methyl (dimethylaminyl)borane, methyl(diethylaminyl)borane, methyl(di-n-propyaminyl)-borane, methyl(diisopropylaminyl)borane, methyl(di-n-butylaminyl)borane, methyl(dicyclopentyl-aminyl)borane, methyl(dicyclohexylaminyl)borane, methyl(pyrrolidinyl)borane, or methyl(piperidinyl)-borane; alternatively, tert-butyl(dimethylaminyl)borane, tert-butyl(diethylaminyl)borane, tert-butyl(di-n-propyaminyl)borane, tert-butyl(diisopropylaminyl)borane, tert-butyl (di-n-butylaminyl)borane, tert-butyl-(dicyclopentylaminyl) borane, tert-butyl(dicyclohexylaminyl)borane, tert-butyl (pyrrolidinyl)borane, or tert-butyl(piperidinyl)borane; alternatively, 2,3-dimethylbut-2-yl(dimethylaminyl)borane, 2,3-dimethylbut-2-yl(diethylaminyl)borane, 2,3-dimethylbut-2-yl(di-n-propyaminyl)borane, 2,3-dimethylbut-2-yl(diisopropylaminyl)borane, 2,3-dimethylbut-2-yl(di-n-butylaminyl)borane, 2,3-dimethylbut-2-yl(dicyclopentylaminyl)borane, 2,3-dimethylbut-2-yl (dicyclohexylaminyl)borane, 2,3-dimethylbut-2-yl(pyrrolidinyl)borane, or 2,3-dimethylbut-2-yl(piperidinyl)borane; alternatively, methyl(dimethylaminyl)borane; alternatively, methyl(diethylaminyl)borane; alternatively, methyl(di-n-propyaminyl)borane; alternatively, methyl(diisopropylaminyl)borane; alternatively, methyl(di-n-butylaminyl)borane; alternatively, methyl-(dicyclopentylaminyl)borane; alternatively, methyl(dicyclohexylaminyl)borane; alternatively, methyl-(pyrrolidinyl)borane; alternatively, methyl(piperidinyl)borane; alternatively, tert-butyl(dimethylaminyl)-borane; alternatively, tert-butyl(diethylaminyl)borane; alternatively, tert-butyl(di-n-propyaminyl)borane; alternatively, tert-butyl(diisopropylaminyl)borane; alternatively, tert-butyl(di-n-butylaminyl)borane; alternatively, tert-butyl(dicyclopentylaminyl)borane; alternatively, tert-butyl(dicyclohexylaminyl)borane; alternatively, tert-butyl(pyrrolidinyl) borane; alternatively, tert-butyl(piperidinyl)borane; alternatively, 2,3-dimethylbut-2-yl(dimethylaminyl)borane; alternatively, 2,3-dimethylbut-2-yl(diethylaminyl)borane; alternatively, 2,3-dimethylbut-2-yl(di-n-propyaminyl)borane; alternatively, 2,3-dimethylbut-2-yl(diiso-propylaminyl)borane; alternatively, 2,3-dimethylbut-2-yl(di-n-butylaminyl)borane; alternatively, 2,3-dimethylbut-2-yl (dicyclopentylaminyl)borane; alternatively, 2,3-dimethylbut-2-yl(dicyclohexyl-aminyl)borane; alternatively, 2,3-dimethylbut-2-yl(pyrrolidinyl)borane; or alternatively, 2,3-dimethylbut-2-yl(piperidinyl)borane. Other hydrogen monoaminoboranes can be readily envisioned and contemplated from the present disclosure. Additionally, any hydrogen monoaminoborane disclosed herein can be combined with any neutral ligand described herein to describe hydrogen monoaminoborane-neutral ligand complex which can be utilized in processes described herein.

In an embodiment, the hydrogen boronic acid ester, which can be utilized in the processes described herein, or can be the hydrogen boronic acid ester of a hydrogen boronic acid ester-neutral ligand complex, which can be utilized in the processes described herein, can be dimethyl boronate, diethyl boronate, di-n-propyl boronate, diisopropyl boronate, di-n-butyl boronate, di-tert-butyl boronate, diphenyl boronate, 1,3,2-dioxa borolane, 4,4,5,5-tetramethyl-1,3,2-dioxaborolane (pinacolborane), 1,3,2-benzodioxaborole (catecholborane), or any combination thereof; alternatively, dimethyl boronate; alternatively, diethyl boronate; alternatively, di-n-propyl boronate; alternatively, diisopropyl boronate; alternatively, di-n-butyl boronate; alternatively, di-tert-butyl boronate; alternatively, diphenyl boronate; alternatively, 1,3,2-dioxaborolane; alternatively, 4,4,5,5-tetramethyl-1,3,2-dioxaborolane (pinacolborane); or alternatively, 1,3,2-benzodioxaborole (catecholborane). Other hydrogen boronic acid esters can be readily envisioned and contemplated from the present disclosure. Additionally, any hydrogen boronic acid ester disclosed herein can be combined with any neutral ligand described herein to describe hydrogen boronic acid ester-neutral ligand complex which can be utilized in processes described herein.

In an embodiment, the hydrogen boronic dithio acid ester, which can be utilized in the processes described herein, or can be the hydrogen boronic thio acid ester of a hydrogen boronic dithio acid ester-neutral ligand complex, which can be utilized in the processes described herein, can be dimethyl dithioboronate, diethyl dithioboronate, di-n-propyl dithioboronate, diisopropyl dithioboronate, di-n-butyl dithioboronate, di-tert-butyl dithioboronate, diphenyl dithioboronate, or any combination thereof; alternatively, dimethyl dithioboronate; alternatively, diethyl dithioboronate; alternatively, di-n-propyl dithioboronate; alternatively, diisopropyl dithioboronate; alternatively, di-n-butyl dithioboronate; alternatively, di-tert-butyl dithioboronate; or diphenyl dithioboronate. Other hydrogen boronic dithio acid esters can be readily envisioned and contemplated from the present disclosure. Additionally, any hydrogen boronic dithio acid ester disclosed herein can be combined with any neutral ligand described herein to describe hydrogen boronic dithio acid ester-neutral ligand complex which can be utilized in processes described herein.

In an embodiment, the hydrogen diaminoborane, which can be utilized in the processes described herein, or can be the hydrogen diaminoborane of a hydrogen diaminoborane-neutral ligand complex, which can be utilized in the processes described herein, can be bis(dimethylaminyl)borane, bis(diethylaminyl)borane, bis(di-n-propyaminyl)borane, bis (diisopropylaminyl)borane, bis(di-n-butyl-aminyl)borane, bis(di-tert-butylaminyl)borane, bis(dicyclopentylaminyl)borane, or bis(dicyclohexyl-aminyl)borane; alternatively, bis (dimethylaminyl)borane; alternatively, bis(diethylaminyl) borane; alternatively, bis(di-n-propyaminyl)borane; alternatively, bis(diisopropylaminyl)borane; alternatively, bis(di-n-butylaminyl)borane; alternatively, bis(di-tert-butylaminyl)borane; alternatively, bis(dicyclo-pentylaminyl)borane; or alternatively, bis(dicyclohexylaminyl)borane. Other hydrogen monoaminoboranes can be readily envisioned and contemplated from the present disclosure. Additionally, any hydrogen monoaminoborane disclosed herein can be combined with any neutral ligand described herein to describe hydrogen monoaminoborane-neutral ligand complex which can be utilized in processes described herein.

In a non-limiting embodiment, the hydrogen-boron bond containing compound can be a hydrogen azaborolidine, a hydrogen diazaborlidine; alternatively, a hydrogen azaborolidine or alternatively, a hydrogen diazaborolidine. In an embodiment, the hydrogen-boron bond containing compound can be a hydrogen azaborolidine represented by the formula

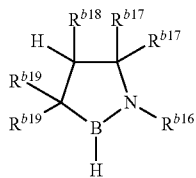

where $R^{b16}$, each $R^{b17}$, $R^{b18}$, each $R^{b19}$ independently can be hydrogen, a halogen, or an organyl group; alternatively, hydrogen, a halogen, or a hydrocarbyl group; alternatively, hydrogen; or alternatively, a halogen. In an embodiment, each $R^{b17}$, $R^{b18}$, each $R^{b19}$ can be the same; or alternatively, one or more of $R^{17}$, $R^{18}$, each $R^{19}$ can be different. In some embodiments, the organyl group which can be utilized as $R^{b6}$, each $R^{b17}$, $R^{b18}$, each $R^{b19}$ (when $R^{b16}$, $R^{b17}$, $R^{b18}$, $R^{b19}$ are not hydrogen or a halogen) independently can be a $C_1$ to $C_{15}$, a $C_1$ to $C_{10}$, or a $C_1$ to $C_6$ organyl group; alternatively, $C_1$ to $C_{15}$, a $C_1$ to $C_{10}$, or a $C_1$ to $C_6$ hydrocarbyl group. In an embodiment, the hydrocarbyl group which can be utilized as a $R^{16}$, each $R^{17}$, $R^{18}$, each $R^{19}$ (when $R^{b16}$, $R^{b17}$, $R^{b18}$, $R^{b19}$ are not hydrogen or a halogen) independently can be $C_1$ to $C_{15}$ alkyl group, a $C_4$ to $C_{15}$ cycloalkyl group, a $C_4$ to $C_{15}$ substituted cycloalkyl group, a $C_6$ to $C_{15}$ aryl group, or a $C_7$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_7$ to $C_{15}$ substituted aryl group; alternatively, a $C_1$ to $C_{15}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_7$ to $C_{15}$ substituted aryl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a methyl group, an ethyl group, a propyl group, a butyl group; or alternatively, a methyl group, an ethyl group, a propyl group, a butyl group, or a pentyl group; alternatively, a methyl group, an ethyl group, an n-propyl group, an isopropyl group, an n-butyl group, a tert-butyl group, or a neopentyl group; alternatively, a methyl group; alternatively, an ethyl group; independently, a propyl group; alternatively, an n-propyl group; independently, an isopropyl group; alternatively, a butyl group; alternatively, an n-butyl group; alternatively, a tert-butyl group; alternatively, a pentyl group; or alternatively, a neopentyl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a cyclobutyl group, a cyclopentyl group, a cyclohexyl group, a cycloheptyl group, or cyclooctyl group; alternatively, a cyclopentyl group, or a cyclohexyl group; alternatively, a cyclopentyl group; or alternatively, a cyclohexyl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a phenyl group, or a substituted phenyl group; alternatively, a phenyl group or a methylphenyl group; alternatively, a phenyl group, a 2-methylphenyl group, or a 4-methylphenyl group; alternatively, a phenyl group; alternatively, a substituted phenyl group; alternatively, a methylphenyl group; alternatively, a 2-methylphenyl group; or alternatively, a 4-methylphenyl group. In some embodiments, $R^{b16}$ can be any hydrocarbyl group disclosed herein (e.g. alkyl group, a cycloalkyl group, or a substituted cycloalkyl group, aryl group, or substituted aryl group) while each $R^{17}$, $R^{18}$, each $R^{19}$ can be any group disclosed herein. In an embodiment, the hydrogen-boron bond containing compound can be 4S,5R-4-methyl-5-phenyl-oxazaborolidine, 1-cyclohexyl-2-ethyl-1,2,azaborolidine, or 9,10-azaborabicyclo[3.3.2]decane; alternatively, 4S,5R-4-methyl-5-phenyl-oxazaborolidine alternatively, 1-cyclohexyl-2-ethyl-1,2,azaborolidine; or alternatively, 9,10-azaborahbicyclo[3.3.2]decane.

In an aspect, the hydrogen-boron bond containing compound can be any one or more of the compounds represented by Formulas I through CXXXVII of Table 8.

TABLE 8

| | |
|---|---|
| HBCl$_2$•OEt$_2$ | (I) |
| HBCl$_2$•NMe$_3$ | (II) |
| HBCl$_2$•SMe$_2$ | (III) |
| HBBr$_2$•SMe$_2$ | (IV) |
| HBI$_2$•SMe$_2$ | (V) |
| H$_2$BCl | (VI) |
| H$_2$BCl•TMEDA | (VII) |
| H$_2$BCl•NEt$_3$ | (VIII) |
| H$_2$BCl•SMe$_2$ | (IX) |
| H$_2$BBr•NEt$_3$ | (X) |
| H$_2$BBr•SMe$_2$ | (XI) |
| BH$_3$ | (XII) |
| BH$_3$•OMe$_2$ | (XIII) |
| BH$_3$•THF | (XIV) |
| BH$_3$•NH$_3$ | (XV) |
| BH$_3$•HN$_2$Me | (XVI) |
| BH$_3$•NH2tBu | (XVII) |
| BH$_3$•NHMe$_2$ | (XVIII) |
| BH$_3$•NMe$_3$ | (XIX) |
| BH$_3$•NEt$_3$ | (XX) |
| BH$_3$•Py | (XXI) |
| BH$_3$•TMEDA | (XXII) |
| BH$_3$•SMe$_2$ | (XXIII) |
| BH$_3$•Thiolane | (XXIV) |
| BH$_3$•PF$_3$ | (XXV) |
| BH$_3$•PH$_3$ | (XXVI) |
| BH$_3$•PPh$_3$ | (XXVII) |
| BH$_3$•P(OMe)$_3$ | (XXVIII) |
| BH$_3$•P(Oi-Pr)$_3$ | (XXIX) |
| Al(BH$_4$)$_3$ | (XXX) |
| LiBH$_4$ | (XXXI) |
| NaBH$_4$ | (XXXII) |
| Hf(BH$_4$)$_4$ | (XXXIII) |
| NaCNBH$_3$ | (XXXIV) |
| K(Oi-Pr)$_3$BH | (XXXV) |
| K(s-BuO)$_3$BH) | (XXXVI) |
| 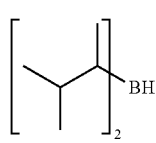 | (XXXVII) |
| 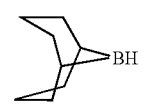 | (XXXVIII) |

TABLE 8-continued
| | |
|---|---|
| 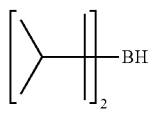 | (XXXIX) |
| 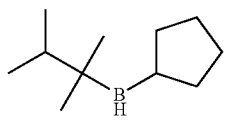 | (XL) |
| 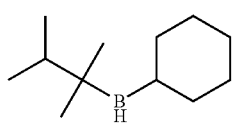 | (XLI) |
| 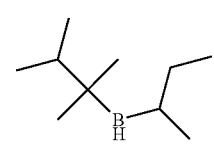 | (XLII) |
| 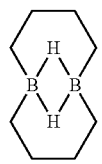 | (XLIII) |
| 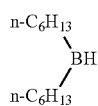 n-C$_6$H$_{13}$<br>n-C$_6$H$_{13}$ | (XLIV) |
| 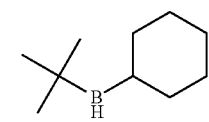 | (XLV) |
| 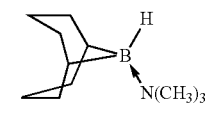 | (XLVI) |
| 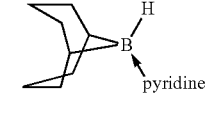 | (XLVII) |
| 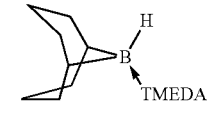 | (XLVIII) |
| 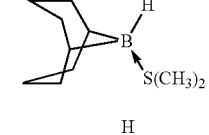 | (XLIX) |
| 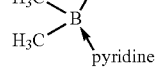 | (L) |
| 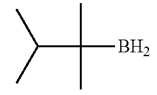 | (LI) |
TABLE 8-continued
| | |
|---|---|
| H$_3$C—BH$_2$ | (LII) |
| n-C$_6$H$_{13}$—BH$_2$ | (LIII) |
| 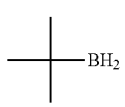 | (LIV) |
|  | (LV) |
| 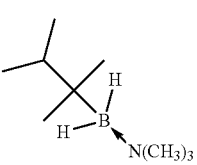 | (LVI) |
| 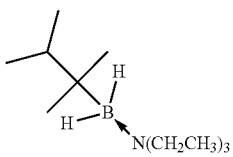 | (LVII) |
| 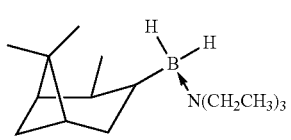 | (LVIII) |
| 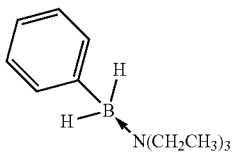 | (LIX) |
| 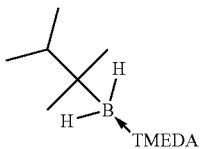 | (LX) |
| 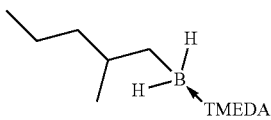 | (LXI) |
| 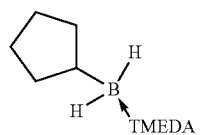 | (LXII) |
| 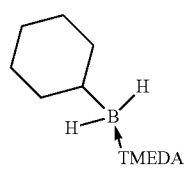 | (LXIII) |

TABLE 8-continued
| | |
|---|---|
| 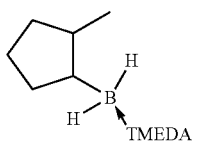 | (LXIV) |
| 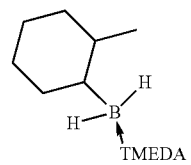 | (LXV) |
| 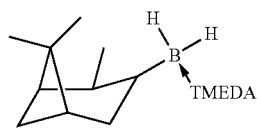 | (LXVI) |
| 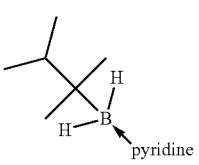 | (LXVII) |
| 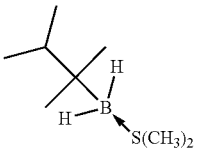 | (LXVIII) |
| 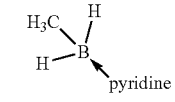 | (LXIX) |
| 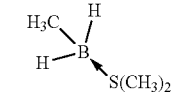 | (LXX) |
| 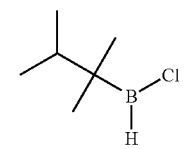 | (LXXI) |
| 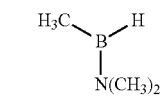 | (LXXII) |
| 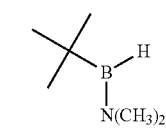 | (LXXIII) |
| 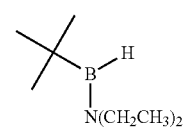 | (LXXIV) |
| 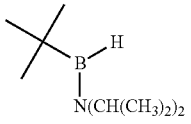 | (LXXV) |
| 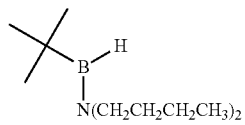 | (LXXVI) |
| 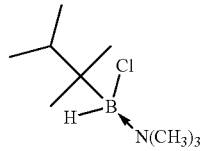 | (LXXVII) |
| 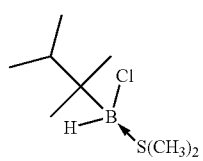 | (LXXIX) |
| 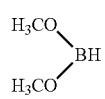 | (LXXX) |
| 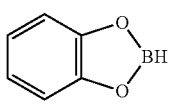 | (LXXXI) |
| 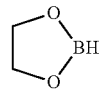 | (LXXXII) |
| 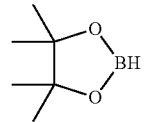 | (LXXXIII) |
| 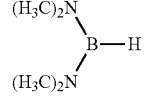 | (LXXXIV) |
| 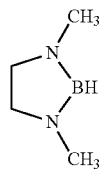 | (LXXXV) |
| 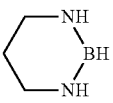 | (LXXXVI) |
| 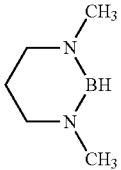 | (LXXXVII) |

TABLE 8-continued

| Structure | Label |
|---|---|
| 1,3-dimethyl-2,3-dihydro-1H-1,3,2-diazaborole | (LXXXVIII) |
| 1,3-dimethyl-2,3-dihydro-1H-benzo[d][1,3,2]diazaborole | (LXXXIX) |
| 1,3,2-dithiaborolane | (XC) |
| bis(phenylthio)borane | (XCI) |
| 1,3,2-dioxaborolane·N(CH$_3$)$_3$ | (XCII) |
| 1,3,2-dithiaborolane·P(CH$_3$)$_3$ | (XCIII) |
| (H$_3$C)$_2$N—BH$_2$ | (XCIV) |
| (H$_3$CH$_2$C)$_2$N—BH$_2$ | (XCV) |
| n-C$_4$H$_9$—BH$_2$ | (XCVI) |
| piperidinyl-BH$_2$ | (XCVII) |
| PhS—BH$_2$ | (XCVIII) |
| H$_2$BCl·TMEDA | (XCIX) |
| H$_2$BI·TMEDA | (C) |
| pivaloyloxy-BH$_2$ | (CI) |
| bis(pivaloyloxy)BH | (CII) |
| benzoyloxy-BH$_2$ | (CIII) |
| bis(benzoyloxy)BH | (CIV) |
| bis(benzoyloxy)BH·THF | (CV) |
| Li$^{\oplus}$ [(cyclohexyl)$_3$BH]$^{\ominus}$ | (CVI) |
| Li$^{\oplus}$ [9-BBN-isopinocampheyl-H]$^{\ominus}$ | (CVII) |
| Li$^{\oplus}$ [(phenyl)$_3$BH]$^{\ominus}$ | (CVIII) |
| Li$^{\oplus}$ [9-BBN-tBu-H]$^{\ominus}$ | (CIX) |
| Li$^{\oplus}$ [bicyclic-B(tBu)(CH$_3$)H]$^{\ominus}$ | (CX) |
| Li$^{\oplus}$ [9-BBN-iPr-H]$^{\ominus}$ | (CXI) |

TABLE 8-continued (CXII) Li⊕ [9-BBN-cyclobutyl-H]⊖

(CXIII) Li⊕ [9-BBN-(2-methylcyclobutyl)-H]⊖

(CXIV) Li⊕ [9-BBN-cyclopentyl-H]⊖

(CXV) Li⊕ [9-BBN-cyclohexyl-H]⊖

(CXVI) Li⊕ [bicyclic-B(n-C₄H₉)₂]⊖

(CXVII) Li⊕ [bicyclic-B(i-C₃H₇)(CH₃)]⊖

(CXVIII) Li⊕ [(cyclopentyl)₃BH]⊖

(CXIX) Li⊕ [(cyclohexyl)₃BH]⊖

(CXX) Li⊕ [9-BBN-(2-methylcyclohexyl)-H]⊖

(CXXI) Li⊕ [9-BBN-phenyl-H]⊖

(CXXII) Li⊕ [9-BBN-benzyl-H]⊖

(CXXIII) Li⊕ [9-BBN-norbornyl-H]⊖

(CXXIV) Li⊕ [9-BBN-(thexyl)-H]⊖

(CXXV) Li⊕ [9-BBN-(n-C₄H₉)-H]⊖

(CXXVI) Li⊕ [9-BBN-(n-C₈H₁₇)-H]⊖

(CXXVII) Li⊕ [9-BBN-(n-C₃H₇)-H]⊖

(CXXVIII) Li⊕ [9-BBN-CH₃-H]⊖

(CXXIX) Li⊕ [bicyclic-B(C₂H₅)(CH₃)]⊖

(CXXX) Li⊕ [bicyclic-B(n-C₄H₉)(CH₃)]⁻

TABLE 8-continued

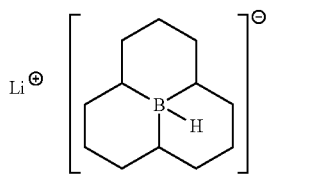 (CXXXI)

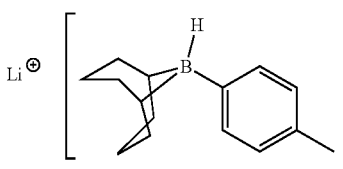 (CXXXII)

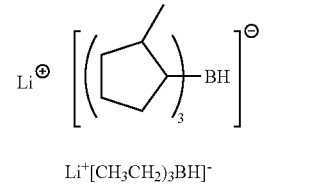 (CXXXIII)

Li$^+$[CH$_3$CH$_2$)$_3$BH]$^-$ (CXXXIV)

Li$^+$[n-C$_4$H$_9$)$_3$BH]$^-$ (CXXXV)

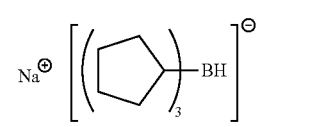 (CXXXVI)

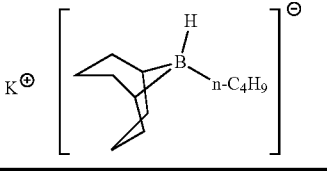 (CXXXVII)

In an aspect, the present disclosure relates to processes for hydroborating olefins (or alkenes). In an embodiment, the processes described herein can comprise contacting an olefin (or alkene), a hydrogen-boron bond containing compound, and an α-diimine metal complex comprising an α-diimine iron methylenetrihydrocarbylsilyl complex or an α-diimine cobalt methylenetrihydrocarbylsilyl complex to form an alkylboron compound under conditions suitable to form an alkylboron compound. In some embodiments, the processes described herein can comprise contacting an olefin (or alkene), a hydrogen-boron bond containing compound, an α-diimine metal complex comprising an α-diimine iron salt complex or an α-diimine cobalt salt complex, and a group 1 metal borohydride to form an alkyl-boron compound under conditions suitable to form an alkylboron compound. In an embodiment, the processes can further comprise recovering the alkylboron compound, for example from a reactor effluent. In an embodiment, when the olefin (or alkene) is an internal olefin (or alkene); or alternatively, a linear internal olefin (or linear internal alkene) the processes can further comprise forming a terminal olefin (or terminal alkene); or alternatively, a linear terminal olefin (or linear terminal alkene) under conditions suitable to form a terminal boron compound (or a terminal alkylboron compound, or a terminal linear alkylboron compound). In an embodiment, the processes can further comprise recovering the terminal boron compound (or the terminal alkylboron compound, or the terminal linear alkylboron compound) from a reactor effluent.

In an alternative aspect, the processes described herein can comprise contacting an internal alkene, a hydrogen-boron bond containing compound, and an α-diimine metal complex comprising an α-diimine iron methylenetrihydrocarbylsilyl complex or an α-diimine cobalt methylenetrihydrocarbylsilyl complex to form a terminal alkylboron compound; or alternatively, the processes described herein can comprise contacting a linear internal alkene, a hydrogen-boron bond containing compound, and an α-diimine metal complex comprising an α-diimine iron methylenetrihydrocarbylsilyl complex or an α-diimine cobalt methylenetrihydrocarbylsilyl complex to form a terminal alkylboron compound. In yet another alternative aspect, the processes described herein can comprise contacting an internal alkene, a hydrogen-boron bond containing compound, an α-diimine metal complex comprising an α-diimine iron salt complex or an α-diimine cobalt salt complex, and a group 1 metal borohydride to form a terminal alkylboron compound; or alternatively, the processes described herein can comprise contacting a linear internal alkene, a hydrogen-boron bond containing compound, an α-diimine metal complex comprising an α-diimine iron salt complex or an α-diimine cobalt salt complex, and a group 1 metal borohydride to form a terminal alkylboron compound. In an embodiment, the processes can further comprise recovering the terminal boron compound (or the terminal alkylboron compound, or the terminal linear alkylboron compound).

For the processes described herein, the olefins and/or alkenes, the hydrogen-boron bond containing compounds, the metal complexes, the group 1 metal borohydrides the alkylboron compounds terminal alkylboron compounds or linear terminal alkylboron compounds), the conditions capable of forming alkylboron compounds, the conditions capable of forming terminal alkylboron compounds, and other process features of the appropriate processes are independently described herein. These independently described features can be utilized, in any combination and without limitation to further describe the processes described herein. It should be noted that while these features can be disclosed under headings within this application, a heading does not limit the disclosure found therein. Additionally, the various aspects and embodiments disclosed herein can be combined in any manner. It is to be understood the term alkylboron compound is meant to encompass the terms terminal alkylboron compound, branched terminal alkylboron compound, linear terminal alkylboron compound, internal alkylboron compound, branched internal alkylboron compound and linear internal alkylboron compound.

In an aspect, the contacting of one or more of the metal complexes, hydrogen-boron bond containing compound, olefin (or alkene), and in some process described herein the group 1 metal borohydride can occur in a solvent or diluent. Alternatively, the contacting of the metal complex, hydrogen-boron bond containing compound, and olefin (or alkene) can occur in the substantial absence of a solvent or diluent. Within the present disclosure, the substantial absence of a solvent or diluent can be less than 5 wt. %, 3, wt. %, 2 wt. %, or 1 wt. % components which are not olefins (or alternatively, alkenes) based upon the amount of olefins charged to the process.

In an aspect, conditions suitable to form the alkylboron compound can include a temperature to form the alkylboron compound. In some embodiments, the temperature to form the alkylboron compound can range from −50° C. to 200° C., from −20° C. to 150° C., from 0° C. to 120° C., from 10° C. to 100° C., from 15° C. to 80° C., from 15° C. to 50° C., or from 15° C. to 30° C. In an aspect, conditions suitable to form a terminal alkylboron compound (or linear terminal alkylboron compound) can include a temperature to form the terminal alkylboron compound. In some embodiments, the temperature to form the terminal alkylboron compound (or the linear terminal alkylboron compound) can range from −50° C. to 200° C., from −20° C. to 150° C., from 0° C. to 120° C., from 10° C. to 100° C., from 15° C. to 80° C., from 15° C. to 50° C., or from 15° C. to 30° C. In an embodiment, the temperature suitable to form the alkylboron compound can be the same as the temperature suitable to form the terminal alkylboron compound (or the linear terminal alkylboron compound); or alternatively, the temperature to form the alkylboron compound can be different from the temperature suitable to form the terminal alkylboron compound (or the linear terminal alkylboron compound).

In an aspect, conditions suitable to form the alkylboron compound and/or the conditions suitable to form a terminal alkylboron compound (e.g., a linear terminal alkylboron compound) can include a molar ratio of the α-diimine metal complex to the hydrogen-boron bond containing compound. The molar ratio of the α-diimine metal complex to hydrogen-boron bond containing compound can be any molar ratio which can catalyze hydroboration of the olefin (e.g., alkene, among others). In an embodiment, molar ratio of the α-diimine metal complex to the hydrogen-boron bond containing compound can range from 10:1 to $10^6$:1, from $10^2$:1 to $10^6$:1, or from $10^3$:1 to $10^6$:1. In an embodiment, the molar ratio of the α-diimine metal complex to the hydrogen-boron bond containing compound suitable to form an alkylboron compound can be the same as the molar ratio of the α-diimine metal complex to the hydrogen-boron bond containing compound to form a terminal alkylboron compound (e.g., the linear terminal alkylboron compound); or alternatively, the molar ratio of the α-diimine metal complex to the hydrogen-boron bond containing compound suitable to form an alkylboron compound can be the different from the molar ratio of the α-diimine metal complex to the hydrogen-boron bond containing compound to form a terminal alkylboron compound (e.g., the linear terminal alkylboron compound).

In an aspect, conditions suitable to form the alkylboron compound can include a contact time to form the desired quantity of alkylboron compound, a contact time to obtain a desired catalyst productivity, and/or a contact time to obtain a desired yield of alkylboron compound. In an embodiment, the contact time to form the desired quantity of alkylboron compound, a contact time to obtain a desired catalyst productivity, and/or a contact time to obtain a desired yield of alkylboron compound can be any contact time necessary to form the desired quantity of alkylboron compound, to obtain a desired catalyst productivity, and/or to obtain a desired yield of alkylboron compound. In some embodiments, the contact time to form the desired quantity of alkylboron compound, to obtain a desired catalyst productivity, and/or to obtain a desired yield of alkylboron compound can range from 1 minute to 48 hours, from 30 minutes to 36 hours, from 1 hour to 12 hours, or from 1 hour to 8 hours. In an aspect, conditions suitable to form the terminal alkylboron compound (or linear terminal alkylboron compound) can include a contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound). In an embodiment, the contact time to form the desired quantity of terminal alkylboron compound (or linear terminal alkylboron compound), a contact time to obtain a desired catalyst productivity, and/or a contact time to obtain a desired yield of terminal alkylboron compound or linear terminal alkylboron compound) can be any contact time necessary to form the desired quantity of terminal alkylboron compound (or linear terminal alkylboron compound), to obtain a desired catalyst productivity, and/or to obtain a desired yield of terminal alkylboron compound (or linear terminal alkylboron compound). In some embodiments, the contact time to form the desired quantity of terminal alkylboron compound (or linear terminal alkylboron compound), to obtain a desired catalyst productivity, and/or to obtain a desired yield terminal alkylboron compound (or linear terminal alkylboron compound) can range from 1 minute to 48 hours, from 30 minutes to 36 hours, from 1 hour to 12 hours, or from 1 hour to 8 hours.

In an embodiment the contact time to form the alkylboron compound can include a contact time to form the desired quantity of alkylboron compound, a contact time to obtain a desired catalyst productivity, and/or a contact time to obtain a desired yield of alkylboron compound. In some embodiments, the contact time to form the terminal alkylboron compound (or linear terminal alkylboron compound) can include a contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound). In some embodiments, the contact time to form the alkylboron compound can be the same as the contact time to form the terminal alkylboron compound; or alternatively, the contact time to form the alkylboron compound can be different from the contact time to the terminal alkylboron compound (or linear terminal alkylboron compound).

In an embodiment, the molar yield of alkylboron compound can be greater than or equal to 70 wt., greater than or equal to 75 wt. %, 80 wt. %, 85 wt. %, or 90 wt. %. In other embodiments, the molar yield of alkylboron compound can be from 60 to 99.5 wt. %, from 70 wt. % to 99 wt. %, from 75 wt. % to 97.5 wt. %, or from 80 wt. % to 95 wt. % of the alkene is converted to the alkylboron compound. In an embodiment, the molar yield of terminal alkylboron compound (or linear terminal alkylboron compound) can be greater than about 70 wt. %, 75 wt. %, 80 wt. %, 85 wt. %, or 90 wt. %. In other embodiments, the molar yield of terminal alkylboron compound (or linear terminal alkylboron compound) from 60 wt. % to 99.5 wt. %, from 70 wt. % to 99 wt. %, from 75 wt. % to 97.5 wt. %, or from 80 wt. % to 95 wt. % based upon the alkylboron compound. As one having ordinary skill in the art would recognize, the molar yield of alkylboron compound or terminal alkylboron compound (or linear terminal alkylboron compound) is based upon the limiting reagent (the hydrogen-boron bond containing compound or the olefin or alkene (or linear alkene, terminal alkene, linear terminal alkene, internal alkene, or linear internal alkene, among others)) of the process.

In an embodiment, the alkylboron compound (e.g., linear or branched, or terminal or otherwise) can be utilized in further processes without isolating the alkylboron compound. In an embodiment, one or more alkylboron compounds (e.g., linear or branched, or terminal or otherwise) can be recovered from the mixture formed by contacting the alkene, hydrogen-boron bond containing compound, and the metal complex, to form the alkylboron compound. The alkylboron compound can be recovered from the mixture using any suitable procedure such as filtration, distillation, washing, or any combination thereof. In an embodiment, the recovered alkylboron compound can be utilized without any further processing. Alternatively, the recovered alkylboron compound can be subjected to additional processing steps (e.g., crystallization) as consistent with a user and/or process goal.

In an embodiment of the processes disclosed herein, the alkene can be an internal alkene (or linear internal alkene) and the alkylboron compound can be a terminal alkylboron compound (or linear terminal alkylboron compound). In an embodiment, the alkylboron compound (or terminal alkylboron compound, or linear terminal alkylboron compound) can be subjected to thermal dehydroboration to form an alkene (or terminal alkene, or linear internal alkene). Thermal dehydroboration of the alkylboron (or terminal alkylboron compound, or linear terminal alkylboron compound) can be carried out using any suitable thermal conditions to effect cleavage of the boron-carbon bond to form the alkene. In an embodiment, the thermal dehydroboration of the alkylboron compound (or terminal alkylboron compound, or linear terminal alkylboron compound) can be carried out at a temperature ranging from 100° C. to 250° C.; alternatively, 120° C. to 230° C.; or alternatively, 140° C. to 220° C.

Various aspects and embodiments described herein refer to general substituents and/or non-hydrogen substituents such as halogen (or halo, halide), hydrocarbyl, hydrocarboxy, alkyl, and/or alkoxy substituents. In an embodiment, each general substituent and/or non-hydrogen substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent of any aspect or embodiment calling for a substituent can be a $C_1$ to $C_{10}$ hydrocarbyl group; or alternatively, a $C_1$ to $C_5$ hydrocarbyl group. In an embodiment, each hydrocarboxy substituent of any aspect or embodiment calling for a substituent can be a $C_1$ to $C_{10}$ hydrocarboxy group; or alternatively, a $C_1$ to $C_5$ hydrocarboxy group. In an embodiment, any halide substituent of any aspect or embodiment calling for a substituent can be a fluoride, chloride, bromide, or iodide; alternatively, a fluoride or chloride; alternatively, fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

The methods described herein can utilize one or more solvents or diluents. Solvents or diluents which can be utilized in aspects of the present disclosure can include without limitation water, hydrocarbons, halogenated hydrocarbons, ethers, carbonates, esters, ketones, aldehydes, alcohols, nitriles and combinations thereof. In some embodiments, an aspect of the present disclosure can call for a polar solvent or diluent. Polar solvents or diluents which can be utilized can include without limitation water, ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. In some embodiments, an aspect of the present disclosure can call for an aprotic polar solvent or diluent. Aprotic polar solvents or diluents which can be utilized can include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. In other embodiments, an aspect of the disclosure can call for a non-polar solvent or diluent. Non-polar solvents or diluents can include without limitation hydrocarbons, halogenated hydrocarbons, or mixtures thereof; alternatively, a hydrocarbon; or alternatively, a halogenated hydrocarbon.

Hydrocarbons and halogenated hydrocarbons can include, for example, aliphatic hydrocarbons, aromatic hydrocarbons, petroleum distillates, halogenated aliphatic hydrocarbons, halogenated aromatic hydrocarbons, or combinations thereof; alternatively aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent or diluent can include $C_3$ to $C_{20}$, $C_4$ to $C_{15}$, or $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents or diluents that can be utilized singly or in any combination can include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents or diluents can include cyclohexane, methyl cyclohexane; alternatively cyclohexane; or alternatively, methylcyclohexane. Aromatic hydrocarbons which can be useful as a solvent or diluent can include $C_6$ to $C_{20}$, or $C_6$ to $C_{10}$ aromatic hydrocarbons. Non-limiting examples of suitable aromatic hydrocarbons that can be utilized singly or in any combination can include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent or diluent can include $C_1$ to $C_{15}$, $C_1$ to $C_{10}$, or $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized can include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent or diluent can include $C_6$ to $C_{20}$, or $C_6$ to $C_{10}$ halogenated aromatic hydrocarbons. Non-limiting examples of suitable halogenated aromatic hydrocarbons can include chlorobenzene, dichlorobenzene, and combinations thereof; alternatively chlorobenzene and dichlorobenzene.

Ethers, carbonates, esters, ketones, aldehydes, or alcohols which can be useful as a solvent or diluent can include $C_2$ to $C_{20}$, $C_2$ to $C_{10}$, or $C_2$ to $C_5$ ethers, carbonates, esters, ketones, aldehydes, or alcohols. Suitable ether solvents or diluents can be cyclic or acyclic. Non-limiting examples of suitable ethers which can be useful as a solvent or diluent can include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent group are disclosed herein and can be utilized without limitation of further describe the substituted tetrahydrofuran, dihydrofuran, furan, 1,3-dioxane, or 1,4 dioxane solvents or diluents. Non-limiting examples of suitable carbonates which can be utilized as a solvent or diluent can include ethylene carbonate, propylene carbonate, diethyl carbonate, diethyl carbonate, glycerol carbonate, and combinations thereof. Non-limiting examples of suitable esters which can be utilized as a solvent or diluent can include ethyl acetate, propyl acetate, butyl acetate, isobutyl isobutyrate, methyl lactate, ethyl lactate, and combinations thereof. Non-limiting examples of suitable ketones which can be utilized as a solvent or diluent can include acetone, ethyl methyl ketone, methyl isobutyl ketone, and combinations thereof. Non-limiting examples of suitable alcohols which can be utilized as a solvent diluent can include methanol, ethanol, propanol, isopropanol, n-butanol, isobutanol, pentanol, hexanol, heptanol, octanol, benzyl alcohol, phenol, cyclohexanol, and the like, or combinations thereof.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure."

Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The data and descriptions provided in the following examples are given to show particular aspects and embodiments of the compounds, catalyst systems, and oligomerization and/or polymerization methods disclosed, and to demonstrate a number of the practices and advantages thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

EXAMPLES

General Procedures

The following general procedures were followed for the experimental investigations of this disclosure. Unless otherwise noted, all experiments were conducted under nitrogen in an MBraun glovebox or using standard Schlenk techniques. Dry, deoxygenated solvents were used unless otherwise indicated. Pentane was deoxygenated and dried by sparging with nitrogen and subsequent passage through a double-column solvent purification system purchased from MBraun Inc. with one column packed with activated alumina and one column packed with activated Q5. Diethyl ether (Et$_2$O) and tetrahydrofuran (THF) were dried over Na/benzophenone and distilled under nitrogen. CDCl$_3$ (Cambridge Isotopes) was used as received. All alkenes were degassed via three repeated freeze-pump-thaw cycles and were stored over activated 4 Å molecular sieves for a minimum of 12 hours prior to use. Pinacolborane (HBPin, Alfa) was used as received and stored under nitrogen. $^1$H and $^{13}$C NMR characterization data were collected at 300K on a Bruker AV-300 spectrometer operating at 300.1 and 75.5 MHz (respectively) with chemical shifts reported in parts per million downfield of SiMe$_4$. For boron-containing products, a $^{13}$C NMR resonance for the carbon attached to the quadrupolar boron center was not observed. $^{11}$B NMR characterization data were collected at 300K on a Bruker AV-300 spectrometer operating at 96.3 MHz with chemical shifts reported in parts per million downfield of BF$_3$.OEt$_2$. Structures for cobalt complexes utilized in various examples described herein are provided below.

Cobalt Salt Complex A

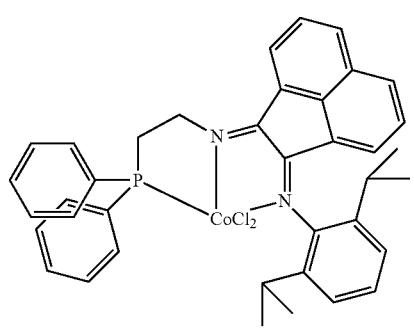

Cobalt Salt Complex B

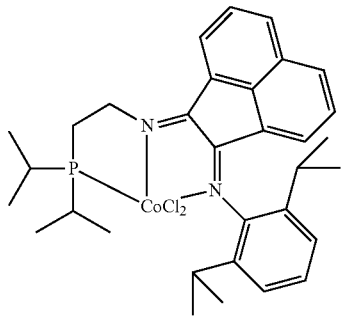

Cobalt Salt Complex C

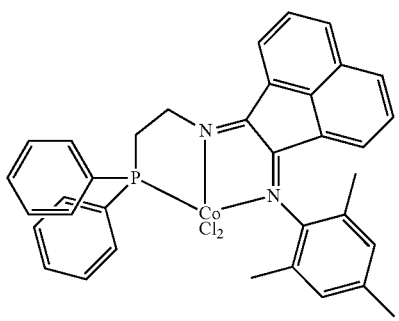

Cobalt Salt Complex D

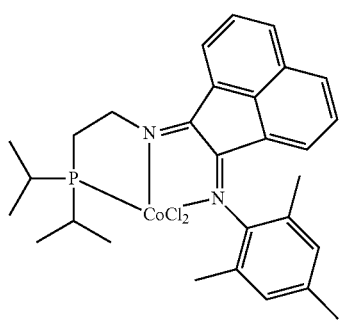

Cobalt Salt Complex E

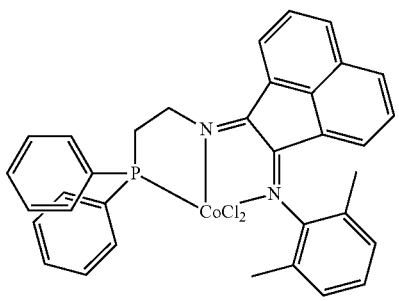

Cobalt Salt Complex F

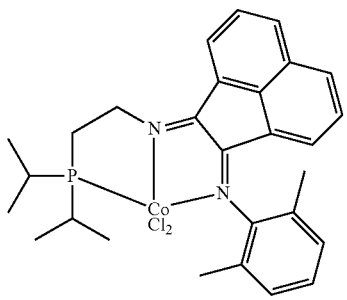

Cobalt Salt Complex G

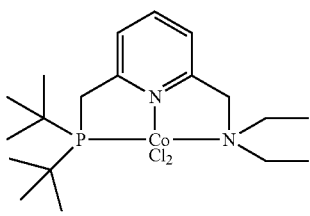

Cobalt Salt Complex H

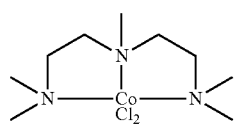

Cobalt Salt Complex I

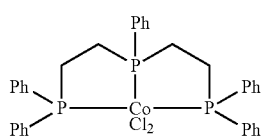

Cobalt Salt Complex J

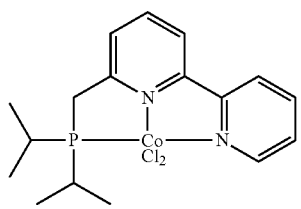

Cobalt Salt Complex K

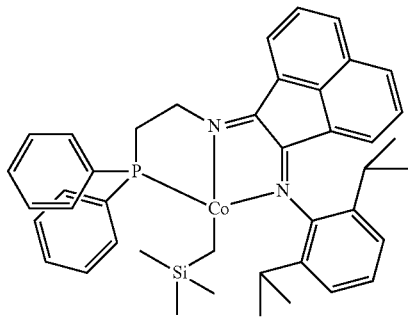

Cobalt Salt Complex L

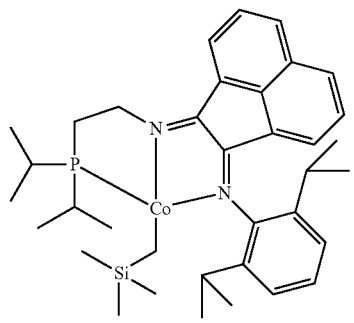

Cobalt Salt Complex M

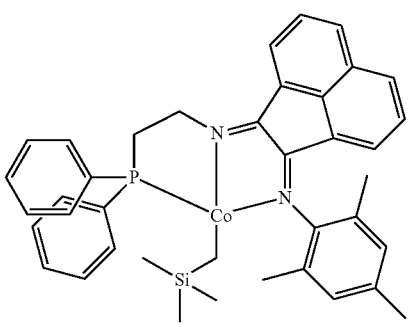

Cobalt Salt Complex N

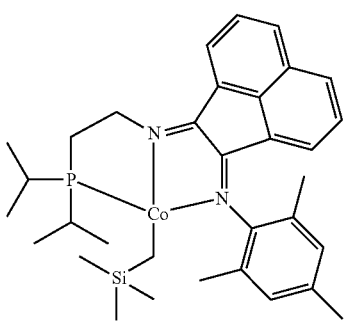

Cobalt Salt Complex P

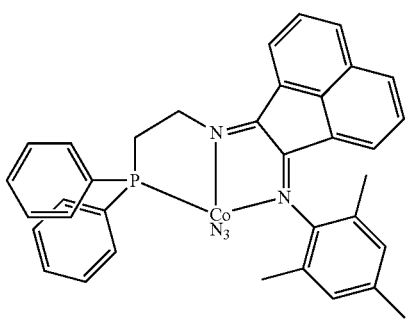

General Procedure for In Situ Activated Hydroboration

The hydroboration of trans-4-octene as depicted in Reaction Scheme A.

Reaction Scheme A

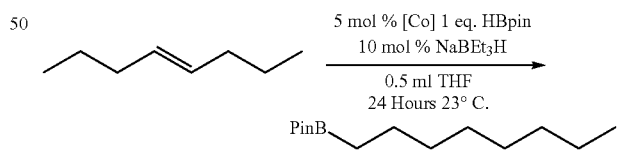

A scintillation vial was charged with 0.100 g (0.78 mmol, 1 equivalent) of pinacol borane (HBPin), 0.088 g (0.78 mmol, 1 equivalent) of trans-4-octene, 0.088 g (0.78 mmol, 1 equivalent) of cyclooctane, 0.5 mL of tetrahydrofuran, 00.039 mmol (0.05 equivalent) of the cobalt complex and 0.11 mL (0.78 mmol, 0.10 equivalent) of a 1 M solution of NaBEt$_3$H in toluene. The vial was then capped and its contents were stirred at 23° C. for 24 h. The reaction mixture was quenched by exposing the mixture to air, and the solvent removed in vacuo. The resulting residue was purified by extraction into hexane and passage through a silica plug. The isolated compound was analyzed by $^1$H and $^{13}$C NMR spectroscopy. The results of the hydroborations are provided in Table 9.

TABLE 9

| Cobalt Salt Complex | Hydroborated Product (mol %) |
|---|---|
| Cobalt Salt Complex A | 45 |
| Cobalt Salt Complex B | 25 |
| Cobalt Salt Complex C | 55 |
| Cobalt Salt Complex D | 63 |
| Cobalt Salt Complex E | 17 |
| Cobalt Salt Complex F | 16 |
| Cobalt Salt Complex G | 51 |
| Cobalt Salt Complex H | 32 |
| Cobalt Salt Complex I | 42 |
| Cobalt Salt Complex J | 58 |

General Procedure for Catalytic Olefin Hydroboration

A scintillation vial was charged with 0.100 g (0.78 mmol, 1 equivalent) of pinacol borane (HBPin), 0.088 g (0.78 mmol, 1 equivalent) of trans-4-octene, 0.088 g (0.78 mmol, 1 equivalent) of cyclooctane, and 0.04 mmol, 0.05 equivalent) of the cobalt complex. The vial was then capped and its contents were stirred at 23° C. The reaction mixture was quenched by exposing the mixture to air, and the solvent removed in vacuo. The resulting residue was purified by extraction into hexane and passage through a silica plug. The isolated compound was analyzed by $^1$H and $^{13}$C NMR spectroscopy. The hydroborations were performed according to this procedure to determine the time required to achieve at least 70% conversion of the trans-4-octene to the terminal octyl pinacolborane. The information for the hydroborations for the four cobalt complexes is provided in Table 10.

TABLE 10

| Cobalt Salt Complex | Time (hours) | Hydroborated Product (mol %) |
|---|---|---|
| Cobalt Salt Complex K | ≈36 hours | >95 |
| Cobalt Salt Complex L | 36 hours | 70 |
| Cobalt Salt Complex M | ≈30 minutes | >95 |
| Cobalt Salt Complex N | 1 hour | ≈45 |
| | 16 hours | >95 |

Order of Addition

The effect of the order of addition of reagents on the hydroboration reaction was investigated. The reaction of trans-4-octene with 2.5 mol % cobalt Salt Complex A with 5 mol % NaBEt$_3$H at 23° C. for 90 min was carried out under the following sets of conditions:

Condition 1: Cobalt Salt Complex A and NaBEt$_3$H were contacted and stirred for one hour prior to the addition of trans-4-octene and HBPin. The reaction provided a 25% conversion of the trans-4-octene.

Condition 2: Cobalt Salt Complex A NaBEt$_3$H and trans-4-octene were contacted and stirred for one hour prior to the addition HBPin. The reaction provided a 30% conversion of the trans-4-octene.

Condition 3: Cobalt Salt Complex A, NaBEt$_3$H, and HBPin were contacted and stirred for one hour prior to the addition of trans-4-octene. The reaction provided a 20% conversion of the trans-4-octene. The results demonstrated that the conversion of the trans-4-octene to an alkylborane is not significantly impacted by the order of addition of the reaction components.

Catalytic Hydroboration

The hydroboration reaction was investigated using an α-diimine metal complex of the type disclosed herein. The reaction of trans-4-octene with 1 equivalent of pinacolborane using 1 mol % Cobalt Complex P in 1 mL tetrahydrofuran at 23° C. Table 11 provides the percentage product distribution as a function of time while FIG. 1 depicts the concentration of products as a function of time.

TABLE 11

| Time (min.) | Conversion to Product (%) | Total Olefin left (%) | Isomerized Olefin (%) |
|---|---|---|---|
| 10 | 3 | 97 | 4 |
| 20 | 6 | 94 | 7 |
| 30 | 9 | 91 | 11 |
| 40 | 11 | 89 | 14 |
| 50 | 13 | 87 | 14 |
| 60 | 15 | 85 | 15 |
| 90 | 19 | 81 | 18 |
| 120 | 23 | 77 | 20 |
| 240 | 33 | 67 | 15 |
| 960 | 56 | 44 | 27 |

While preferred embodiments of the invention have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Background is not an admission that it is prior art to the present invention, especially any reference that can have a publication date after the priority date of this application. The disclosures of all patents, patent applications, and publications cited herein are hereby incorporated by reference, to the extent that they provide exemplary, procedural or other details supplementary to those set forth herein.

The following are enumerated embodiments are provided as non-limiting examples.

A first embodiment is a process comprising contacting a) an alkene, b) a hydrogen-boron bond containing compound, c) an α-diimine metal salt complex comprising an α-diimine iron salt complex or an α-diimine cobalt salt complex, and d) a group 1 metal borohydride under conditions suitable to form an alkylboron compound A second embodiment which is the process of the first embodiment, wherein the α-diimine metal salt complex is an α-diimine iron halide complex or an α-diimine cobalt halide complex.

A third embodiment which is the process of any of the first through second embodiments, wherein the α-diimine comprises; 1) an α-diimine group, ii) a first imine nitrogen group comprising a $C_1$ to $C_{30}$ hydrocarbyl group attached to a first imine nitrogen atom of the α-diimine group, and iii) a second imine nitrogen group, and (1) a metal complexing group, and (2) a linking group linking the metal complexing group to a second imine nitrogen atom of the α-diimine group.

A fourth embodiment which is the process of any of the first through third embodiments, wherein the α-diimine metal salt complex has the structure

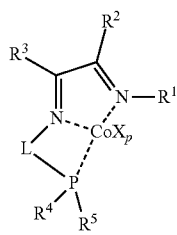

wherein $R^1$ is a $C_1$ to $C_{30}$ hydrocarbyl group, $R^2$ and $R^3$ independently are $C_1$ to $C_{30}$ hydrocarbyl groups and optionally $R^2$ and $R^3$ can be joined to form a ring or ring system, L is a $C_1$ to $C_{10}$ hydrocarbylene group, $R^4$ and $R^5$ independently are $C_6$ to $C_{30}$ aryl groups, each X is a halide, and p is 2 or 3.

A fifth embodiment which is the process of any of the first through fourth embodiments, where the alkene is a linear internal alkene.

A sixth embodiment which is the process of any of the first through fifth embodiments, wherein a cobalt to boron molar ratio ranges from 0.001:1 to 0.05:1.

A seventh embodiment which is the process of any of the first through sixth embodiments, wherein the alkylboron compound is formed at a temperature of from 15° C. to 30° C.

An eighth embodiment which is the process of any of the first through seventh embodiments, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

A ninth embodiment which is the process of any of the first through eighth embodiments, wherein the hydrogen-boron bond containing compound comprises a hydrogen borinic acid ester, a hydrogen boronic acid ester, or combinations thereof.

A tenth embodiment which is a process comprising contacting a) an alkene, b) a hydrogen-boron bond containing compound, and c) an α-diimine metal salt complex comprising an α-diimine iron methylenetrihydrocarbylsilyl complex or an α-diimine cobalt methylenetrihydrocarbylsilyl complex, to form an alkyl-boron compound under conditions suitable to form an alkylboron compound to form an alkyl-boron compound under conditions suitable to form an alkylboron compound.

An eleventh embodiment which is the process of the tenth embodiment, wherein the α-diimine comprises i) an α-diimine group, ii) a first imine nitrogen group comprising a $C_1$ to $C_{30}$ hydrocarbyl group attached to a first imine nitrogen atom of the α-diimine group, iii) a second imine nitrogen group comprising (1) a metal complexing group, and (2) a linking group linking the metal complexing group to a second imine nitrogen atom of the α-diimine group.

A twelfth embodiment which is the process of any of the tenth embodiment through eleventh embodiments, wherein the α-diimine cobalt methylenetrihydrocarbylsilyl complex has the structure:

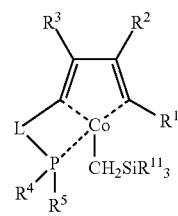

wherein $R^1$ is a $C_1$ to $C_{30}$ hydrocarbyl group, $R^2$ and $R^3$ independently are $C_1$ to $C_{30}$ hydrocarbyl groups and optionally $R^2$ and $R^3$ can be joined to form a ring or ring system, L is a $C_1$ to $C_{10}$ hydrocarbylene group, $R^4$ and $R^5$ independently are $C_6$ to $C_{30}$ aryl groups, and each $R^{11}$ independently is a $C_1$ to $C_5$ hydrocarbyl group.

A thirteenth embodiment which is the process of any of the tenth through thirteenth embodiments, where the alkene is a linear internal alkene.

A fourteenth embodiment which is the process of any of the tenth through thirteenth embodiments, wherein a cobalt to boron molar ratio ranges from 0.001:1 to 0.05:1.

A fifteenth embodiment which is the process of any of the tenth through fourteenth embodiments, wherein the alkylboron compound is formed at a temperature of from 15° C. to 30° C.

A sixteenth embodiment which is the process of any of the tenth through fifteenth embodiments, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

A seventeenth embodiment which is the process of any of the tenth through sixteenth embodiments, wherein the hydrogen-boron bond containing compound comprises a hydrogen borinic acid ester, a hydrogen boronic acid ester, or combinations thereof.

An eighteenth embodiment which is a process comprising contacting an alkene, a hydrogen-boron bond containing compound, and an α-diimine metal salt complex to form an alkyl-boron compound under conditions suitable to form an alkylboron compound.

A nineteenth embodiment which is the process of the eighteenth embodiment, wherein the α-diimine metal complex comprises iron, cobalt, or mixtures thereof.

A twentieth embodiment which is the process of any of the eighteenth through nineteenth embodiments, wherein the α-diimine metal complex comprises cobalt.

A twenty-first embodiment which is the process of any of the eighteenth through twentieth embodiments, wherein the alkene is a linear internal alkene and the process further comprises forming a terminal alkylboron compound.

A twenty-second embodiment which is the process of any of the eighteenth through twenty-first embodiments, wherein the terminal alkylboron compound is formed at a temperature from 15° C. to 30° C.

A twenty-third embodiment which is the process of any of the eighteenth through twenty-second embodiments, further comprising dehydroboration of the alkylboron compound to form a terminal olefin.

What is claimed:

1. A process comprising contacting:
   a) a linear internal alkene,
   b) a hydrogen-boron bond containing compound,
   c) an α-diimine metal salt complex comprising an α-diimine iron salt complex or an α-diimine cobalt salt complex, and
   d) a group 1 metal borohydride to form a linear terminal alkylboron compound under conditions suitable to form the linear terminal alkylboron compound.

2. The process of claim 1, wherein the α-diimine metal salt complex is an α-diimine iron halide complex or an α-diimine cobalt halide complex.

3. The process of claim 1, wherein the α-diimine comprises:
   i) an α-diimine group,
   ii) a first imine nitrogen group comprising a $C_1$ to $C_{30}$ hydrocarbyl group attached to a first imine nitrogen atom of the α-diimine group, and
   iii) a second imine nitrogen group comprising:
      (1) a metal complexing group, and
      (2) a linking group linking the metal complexing group to a second imine nitrogen atom of the α-diimine group.

4. The process of claim 1, wherein the α-diimine metal salt complex has the structure

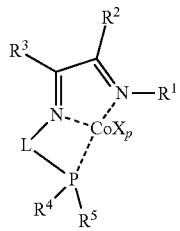

wherein
$R^1$ is a $C_1$ to $C_{30}$ hydrocarbyl group,
$R^2$ and $R^3$ independently are $C_1$ to $C_{30}$ hydrocarbyl groups and optionally $R^2$ and $R^3$ can be joined to form a ring or ring system,
L is a $C_1$ to $C_{10}$ hydrocarbylene group,
$R^4$ and $R^5$ independently are $C_6$ to $C_{30}$ aryl groups,
each X is a halide, and
p is 2 or 3.

5. The process of claim 1, wherein a cobalt to boron molar ratio ranges from 0.001:1 to 0.05:1.

6. The process of claim 1, wherein the linear terminal alkylboron compound is formed at a temperature of from 15° C. to 30° C.

7. The process of claim 1, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

8. The process of claim 1, wherein the hydrogen-boron bond containing compound comprises a hydrogen borinic acid ester, a hydrogen boronic acid ester, or combinations thereof.

9. The process of claim 1, wherein the α-diimine metal salt complex comprises an α-diimine iron methylenetrihydrocarbylsilyl complex or an α-diimine cobalt methylenetrihydrocarbylsilyl complex.

10. The process of claim 9, wherein the α-diimine comprises:
    i) an α-diimine group,
    ii) a first imine nitrogen group comprising a $C_1$ to $C_{30}$ hydrocarbyl group attached to a first imine nitrogen atom of the α-diimine group, and
    iii) a second imine nitrogen group comprising:
       (1) a metal complexing group, and
       (2) a linking group linking the metal complexing group to a second imine nitrogen atom of the α-diimine group.

11. The process of claim 9, wherein the α-diimine cobalt methylenetrihydrocarbylsilyl complex has the structure:

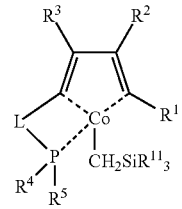

wherein
$R^1$ is a $C_1$ to $C_{30}$ hydrocarbyl group,
$R^2$ and $R^3$ independently are $C_1$ to $C_{30}$ hydrocarbyl groups and optionally $R^2$ and $R^3$ can be joined to form a ring or ring system,
L is a $C_1$ to $C_{10}$ hydrocarbylene group,
$R^4$ and $R^5$ independently are $C_6$ to $C_{30}$ aryl groups, and
each $R^{11}$ independently is a $C_1$ to $C_5$ hydrocarbyl group.

12. The process of claim 9 wherein a cobalt to boron molar ratio ranges from 0.001:1 to 0.05:1.

13. The process of claim 9, wherein the linear terminal alkylboron compound is formed at a temperature of from 15° C. to 30° C.

14. The process of claim 9, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

15. The process of claim 9, wherein the hydrogen-boron bond containing compound comprises a hydrogen borinic acid ester, a hydrogen boronic acid ester, or combinations thereof.

16. The process of claim 1, wherein the α-diimine comprises:
    i) an α-diimine group derived from a $C_4$ to $C_{60}$ α-dione,
    ii) a first imine nitrogen group comprising a $C_1$ to $C_{30}$ hydrocarbyl group attached to a first imine nitrogen atom of the α-diimine group, and
    iii) a second imine nitrogen group comprising:
       (1) a metal complexing group, and
       (2) a linking group linking the metal complexing group to a second imine nitrogen atom of the α-diimine group.

17. The process of claim 9, wherein the α-diimine comprises:
- i) an α-diimine group derived from a $C_4$ to $C_{60}$ α-dione,
- ii) a first imine nitrogen group comprising a $C_1$ to $C_{30}$ hydrocarbyl group attached to a first imine nitrogen atom of the α-diimine group, and
- iii) a second imine nitrogen group comprising:
    - (1) a metal complexing group, and
    - (2) a linking group linking the metal complexing group to a second imine nitrogen atom of the α-diimine group.

* * * * *